United States Patent
Randloev et al.

(10) Patent No.: US 10,307,109 B2
(45) Date of Patent: Jun. 4, 2019

(54) GLUCOSE PREDICTOR BASED ON REGULARIZATION NETWORKS WITH ADAPTIVELY CHOSEN KERNELS AND REGULARIZATION PARAMETERS

(75) Inventors: Jette Randloev, Vaerloese (DK);
Samuel McKennoch, Bagsvaerd (DK);
Sergei Pereverzyev, Linz (AT);
Sivananthan Sampath, Linz (AT)

(73) Assignee: Novo Nordisk A/S, Bagsvaerd (DK)

( * ) Notice: Subject to any disclaimer, the term of this patent is extended or adjusted under 35 U.S.C. 154(b) by 972 days.

(21) Appl. No.: 14/112,311

(22) PCT Filed: Apr. 20, 2012

(86) PCT No.: PCT/EP2012/057260
§ 371 (c)(1),
(2), (4) Date: Oct. 17, 2013

(87) PCT Pub. No.: WO2012/143505
PCT Pub. Date: Oct. 26, 2012

(65) Prior Publication Data
US 2014/0073892 A1   Mar. 13, 2014

Related U.S. Application Data

(60) Provisional application No. 61/481,315, filed on May 2, 2011.

(30) Foreign Application Priority Data

Apr. 20, 2011   (EP) .................................... 11163219

(51) Int. Cl.
*G01N 33/48* (2006.01)
*A61B 5/00* (2006.01)
(Continued)

(52) U.S. Cl.
CPC ........ *A61B 5/7275* (2013.01); *A61B 5/14532* (2013.01); *A61B 5/4848* (2013.01);
(Continued)

(58) Field of Classification Search
None
See application file for complete search history.

(56) References Cited

U.S. PATENT DOCUMENTS

| | | |
|---|---|---|
| 2003/0212317 A1 | 11/2003 | Kovatchev et al. |
| 2004/0249254 A1 | 12/2004 | Racchini et al. |
| 2005/0240356 A1 | 10/2005 | Staib et al. |

FOREIGN PATENT DOCUMENTS

| | | |
|---|---|---|
| JP | 2005-308742 A | 11/2005 |
| WO | 2005/041103 A2 | 5/2005 |

OTHER PUBLICATIONS

Eren-Oruklu M et al., Diabetes Technology & Therapeutics., "Estimation of Future Glucose Concentrations With Subject-Specific Recursive Linear Models", 2009, vol. 11, No. 4, pp. 243-253.
(Continued)

*Primary Examiner* — Larry D Riggs, II
(74) *Attorney, Agent, or Firm* — Leon Y. Lum

(57) ABSTRACT

The invention relates to a method and a device for predicting a glycaemic profile of a subject. A multistage algorithm is employed comprising a prediction setting stage specifying a functional space for the prediction and a prediction execution stage specifying a predicted future glycaemic state of the subject in the functional space as a continuous function of time.

41 Claims, 24 Drawing Sheets

(51) Int. Cl.
    A61B 5/145    (2006.01)
    G16H 50/50    (2018.01)
    G06F 19/00    (2018.01)
(52) U.S. Cl.
    CPC .......... *A61B 5/4866* (2013.01); *A61B 5/7264* (2013.01); *G06F 19/00* (2013.01); *G16H 50/50* (2018.01)

(56) References Cited

OTHER PUBLICATIONS

Kovatchev B et al., Journal of Diabetes Science and Technology, "Peculiarities of the Continuous Glucose Monitoring Data Stream and Their Impact on Developing Closed-Loop Control Technology", 2008, vol. 2, No. 1, pp. 158-163.
Reifman J et al., Journal of Diabetes Science and Technology, "Predictive Monitoring for Improved Management of Glucose Levels", 2007, vol. 1, No. 4, pp. 478-486.
Sparacino G et al., IEEE Transactions on Biomedical Engineering, "Glucose Concentration Can Be Predicted Ahead in Time From Continuous Glucose Monitoring Sensor Time-Series", 2007, vol. 54, No. 5, pp. 931-937.
Zanderigo F et al., Journal of Diabetes Science and Technology, "Glucose Prediction Algorithms From Continuous Monitoring Data: Assessment of Accuracy Via Continuous Glucose Error-Grid Analysis", 2007, vol. 1, No. 5, pp. 645-651.
V. Naumova, et al., Extrapolation in variable RKHSs with application to the blood glucose reading, RICAM Report Apr. 2011, Johan Radon Institute for Computational and Applied Mathematics (RICAM), Austrian Academy of Sciences (OAW), Mar. 2011, [online], [retrieved on Feb. 22, 2016], [retrieved from the internet: <URL:http://www.ricam.oeaw.ac.at/files/reports/11/rep11-04.pdf>.
Sergei V. Pereverzev, et al., Adaptive Regularization Algorithms in Learning Theory-Case Study: Prediction of Blood Glucose Level, [online] Johan Radon Institute for Computational and Applied Mathematcis (RICAM), Austrian Academy of Sciences (OAW), 2008, Workshop on Inverse and Partial Information Problems: Methodology and Applications, [retrieved on Feb. 22, 2016] Retrieved from the internet: <URL:https://www.ricam.oeaw.ac.at/specsem/sef/events/program/slides/pereverzyev_ipip.pdf>.
F. Bauer et al., On regularization algorithms in learning theory, Journal of Complexity, 2007, vol. 23, Issue 1, pp. 52-72.
Zhu Xiaotang et al "Model-Based IDDM Blood Glucose Prediction Control" Paper Collection of the 10th Annual Meeting of Youth of Chinese Institutes of Electronics. 2005 pp. 1-6.
Wang Long "Research on Prediction Model for Detection of Glucose Solution Concentration" Wanfang Dissertation 2008. Full Text.
Wu Huifei et al "Modeling and Prediction for Noninvasive Blood Glucose Concentration" Electronic Test No. 1, 2010 pp. 16-18 and 67.
Hein M et al. Mathematical and Computational Foundations of Learning Theory, Year 2011, vol. 1, No. 7, pp. 53-69 XP055086269.
Naumova V et al. "A Meta-Learning approach to the regularised learning-Case study:Blood glucose Prediction" Neural Networks, Year 2012, vol. 33, pp. 181-193 XP028426777.
Naumova V et al. A meta-learning approach to the regularized learning-Case study: Blood glucose prediction, RICAM Report 2011-31, John Radon Institute for computational and Applied Mathematics(RICAM), Austrian Academy of Sciences (OAW), XP055086246. Retrieved from the Internet:URL://http://www.ricam.oeaw.ac.at/publications/reports/11/rep11-31.pdf.
Naumova V et al. Blood Glucose Predictors: an Overview on How Recent Developments Help to Unlock the Problem of Glucose Regulation, "Recent Patents on Computer Science" Year 2012, vol. 5, No. 3, pp. 177-187, XP055085502.
Naumova V et al. Extrapolation in Variable RKHSs With Application to the Blood Glucose Reading, RICAM Report Apr. 2011, John Radon Institute for Computational and Applied Mathematics, Austrian Academy of Sciences (OAW), XP055084009, Retrieved from the Internet:URL:http://www.ricam.oeaw.ac.at/publications/reports/11/rep11-04.pdf.
Naumova V et al. Extrapolation in variable RKHSs with application to the blood glucose reading, "Inverse Problems" Year 2011, vol. 27, No. 7, pp. 75010, XP020206514.
Naumova V et al. Reading blood glucose from subcutaneous electric current by means of a regularization in variable Reproducing Kernel Hilbert Spaces, 2011 50th IEEE Conference on Decision and Control and European Control Conference (CDC-ECC) Orlando, FL, USA, Year 2011, pp. 5158-5163, XP032122533.
Pereverzev S et al. Regularized Learning Algorithm for Prediction of Blood Glucose Concentration in "No Action Period", "1st International Conference on Mathematical and Computational Biomedical Engineering" Year 2009, pp. 395-398, XP055083998.
Huajun Wang: "Adaptive Regularization Algorithms in Learning Theory-Case study:Prediction of Blood Glucose Level" Aug. 2008, Masters thesis, XP055085492.
Naumova V et al. Extrapolation in Variable RKHSs With Application to the Blood Glucose Reading, RICAM Report Apr. 2011, John Radon Institute for Computational and Applied Mathematics, Austrian Academy of Sciences (OAW), XP055084009, Print-out of Internet Archive record on Apr. 12, 2011 of RICAM reports webpage: https://web.archive.org/web/20110412115350/http://www.ricam.oeaw.ac.at/publications/reports/, Accessed Aug. 7, 2014.
Naumova V et al. Extrapolation in Variable RKHSs With Application to the Blood Glucose Reading, RICAM Report Apr. 2011, John Radon Institute for Computational and Applied Mathematics, Austrian Academy of Sciences (OAW), XP055084009, Print-out of WebDate result obtained on Oct. 15, 2013 for URL: http://www.ricam.oeaw.ac.at/publications/reports/11/rep11-04.pdf, Accessed Aug. 7, 2014.
Naumova V et al. A meta-learning approach to the regularized learning-Case study: Blood glucose prediction, RICAM Report 2011-31, John Radon Institute for computational and Applied Mathematics(RICAM), Austrian Academy of Sciences (OAW), XP055086246, Print-out of RICAM reports webpage on Oct. 31, 2013, URL: http ://www.ricam.oeaw. ac.at/publications/reports/.
Naumova V et al. A meta-learning approach to the regularized learning-Case study: Blood glucose prediction, RICAM Report 2011-31, John Radon Institute for computational and Applied Mathematics(RICAM), Austrian Academy of Sciences (OAW), XP055086246, Print-out of WebDate result obtained on Oct. 31, 2013 for URL: http ://www.ricam.oeaw.ac.at/publications/reports/11/rep11-31.pdf, Accessed Aug. 7, 2014.
Naumova V et al. Extrapolation in Variable RKHSs With Application to the Blood Glucose Reading, RICAM Report Apr. 2011, John Radon Institute for Computational and Applied Mathematics, Austrian Academy of Sciences (OAW), XP055084009, Print-out of Internet Archive record on Feb. 27, 2011 of RICAM reports webpage: https://web.archive.org/web/20110227143429/http://www.ricam.oeaw.ac.at/publications/reports, Accessed Aug. 7, 2014.
Naumova V et al. Extrapolation in Variable RKHSs With Application to the Blood Glucose Reading, RICAM Report Apr. 2011, John Radon Institute for Computational and Applied Mathematics, Austrian Academy of Sciences (OAW), XP055084009, Print-out of part of the source code for https://web.archive.org/web/20110412115350/http://www.ricam.oeaw.ac.at/publications/ reports/, Accessed Aug. 7, 2014.

| BG <70 mg/dL (%) | | | | |
|---|---|---|---|---|
| Point error grid zones | | | | |
| | A | B | E | Acc. = 84.32 |
| A | 74.51 | 9.81 | 0 | Ben. = 3.92 |
| B | 9.81 | 0 | 0 | Err. = 11.76 |
| sC | 0 | 0 | 0 | |
| IC | 0 | 0 | 0 | |
| uD | 0 | 1.96 | 0 | |
| D | 1.96 | 0 | 0 | |
| uE | 0 | 0 | 0 | |
| E | 1.96 | 0 | 0 | |

| BG 70-180 mg/dL (%) | | | | |
|---|---|---|---|---|
| Point error grid zones | | | | |
| | A | B | C | Acc. = 93.32 |
| A | 66.52 | 14.4 | 0 | Ben. = 6.68 |
| B | 5.865 | 6.84 | 0 | Err. = 0 |
| sC | 0 | 0.26 | 0 | |
| IC | 0 | 0 | 0 | |
| uD | 0 | 0.13 | 0 | |
| D | 0.26 | 4.69 | 0 | |
| uE | 0 | 0 | 0 | |
| E | 0 | 0 | 0 | |

| BG >180 mg/dL (%) | | | | | |
|---|---|---|---|---|---|
| Point error grid zones | | | | | |
| | A | B | C | D | E | Acc. = 94.02 |
| A | 67.39 | 4.35 | 0 | 0 | 0 | Ben. = 2.17 |
| B | 15.76 | 6.52 | 0 | 0 | 0 | Err. = 3.81 |
| sC | 0 | 0 | 0 | 0 | 0 | |
| IC | 0 | 0 | 0 | 0 | 0 | |
| uD | 1.63 | 0.54 | 0 | 0 | 0 | |
| D | 2.18 | 1.63 | 0 | 0 | 0 | |
| uE | 0 | 0 | 0 | 0 | 0 | |
| E | 0 | 0 | 0 | 0 | 0 | |

Fig. 5

| | BG <70 | mg/dL | (%) | |
|---|---|---|---|---|
| | Point error grid zones | | | |
| | A | D | E | Acc. = 70.9 |
| A | 57.4 | 18.0 | 0 | Ben. = 2.6 |
| B | 13.5 | 5.1 | 0 | Err. = 26.5 |
| nC | 0 | 0 | 0 | |
| IC | 1.2 | 0.4 | 0 | |
| nD | 0.6 | 1.4 | 0 | |
| ID | 0.6 | 0 | 0 | |
| nE | 0 | 0.2 | 0 | |
| IE | 0.8 | 0 | 0 | |

| | BG 70-180 | mg/dL | (%) | |
|---|---|---|---|---|
| | Point error grid zones | | | |
| | A | B | C | Acc. = 88.9 |
| A | 53.2 | 23.4 | 0.1 | Ben. = 6.1 |
| B | 11.6 | 3.7 | 0.1 | Err. = 3 |
| nC | 0.6 | 0.5 | 0 | |
| IC | 0.4 | 0.5 | 0 | |
| nD | 1 | 0.7 | 0 | |
| ID | 1 | 0.4 | 0 | |
| nE | 0.1 | 0.2 | 0 | |
| IE | 0.4 | 0.1 | 0 | |

| | BG >180 | mg/dL | (%) | | |
|---|---|---|---|---|---|
| | Point error grid zones | | | | |
| | A | B | C | D | E | Acc. = 89.1 |
| A | 55.0 | 9.4 | 0 | 0.1 | 0 | Ben. = 6.3 |
| B | 20.1 | 3.7 | 0 | 0.1 | 0 | Err. = 4.6 |
| nC | 1.5 | 0.6 | 0 | 0 | 0 | |
| IC | 1.1 | 0.3 | 0 | 0 | 0 | |
| nD | 2 | 0.8 | 0 | 0 | 0 | |
| ID | 2.4 | 0.3 | 0 | 0 | 0 | |
| nE | 0.6 | 0.3 | 0 | 0 | 0 | |
| IE | 0.7 | 0.1 | 0 | 0 | 0 | |

Fig. 6

|  | BG ≤ 70 mg/dL (%) | | | BG 70-180 mg/dL (%) | | | BG > 180 mg/dL (%) | | |
|---|---|---|---|---|---|---|---|---|---|
| Patient ID | Acc. | Benign | Error | Acc. | Benign | Error | Acc. | Benign | Error |
| Subject1 | 70 | - | 30 | 93.52 | 6.48 | - | 98.11 | 1.89 | - |
| Subject2 | 100 | - | - | 94.51 | 3.82 | 1.67 | 90.32 | 3.23 | 6.45 |
| Subject3 | 73.68 | 5.26 | 21.05 | 90.78 | 7.45 | 1.77 | 90.28 | 4.17 | 5.56 |
| Subject4 | 84.31 | 3.92 | 11.77 | 93.32 | 6.68 | - | 94.02 | 2.17 | 3.81 |
| Subject5 | 87.5 | 4.17 | 8.33 | 85.81 | 12.79 | 1.4 | 90.73 | 3.23 | 6.05 |
| Subject6 | 90.63 | - | 9.37 | 98.65 | 1.35 | - | 100 | - | - |
| Subject7 | 93.94 | - | 6.06 | 98.25 | 1.75 | - | 98.77 | - | 1.23 |
| Subject8 | 77.78 | - | 22.22 | 99.31 | 0.69 | - | 100 | - | - |
| Subject9 | 100 | - | - | 96.94 | 2.18 | 0.87 | 100 | - | - |
| Subject10 | - | - | - | 92.67 | 6.9 | 0.43 | 97.34 | 1.6 | 1.06 |
| Subject11 | 73.68 | - | 26.32 | 96.07 | 3.37 | 0.56 | 100 | - | - |

Fig. 7

|  | Sensor Performance (%) | | | | | Predictor Performance (%) (30 mins ahead) | | | | |
|---|---|---|---|---|---|---|---|---|---|---|
| Patient ID | A | B | C | D | E | A | B | C | D | E |
| Subject1 | 65.71 | 25.72 | - | 8.27 | - | 48.57 | 42.86 | - | 8.57 | - |
| Subject2 | 91.89 | 8.1 | - | - | - | 71.62 | 27.03 | - | 1.35 | - |
| Subject3 | 79.17 | 15.28 | - | 5.55 | - | 51.39 | 41.67 | - | 6.94 | - |
| Subject4 | 85.71 | 9.09 | - | 5.2 | - | 58.44 | 35.07 | - | 6.49 | - |
| Subject5 | 90.67 | 6.67 | - | 2.67 | - | 58.67 | 38.67 | - | 2.67 | - |

Fig. 8

Clarke's - EGA for half an hour prediction (%)

| Patient ID | A | B | C | D | E |
|---|---|---|---|---|---|
| Subject1 | 91.85 | 7.39 | - | 0.76 | - |
| Subject2 | 88.15 | 11.04 | 0.8 | - | - |
| Subject3 | 80.04 | 19.4 | - | 0.57 | - |
| Subject4 | 86.82 | 12.02 | - | 1.16 | - |
| Subject5 | 82.9 | 16.48 | 0.13 | 0.49 | - |
| Subject6 | 90.28 | 9.72 | - | - | - |
| Subject7 | 92.39 | 7.43 | - | 0.18 | - |
| Subject8 | 88.29 | 10.81 | - | 0.9 | - |
| Subject9 | 93.38 | 6.62 | - | - | - |
| Subject10 | 92.19 | 7.74 | - | 0.07 | - |
| Subject11 | 87.74 | 11.4 | - | 0.86 | - |

Comparison with Reifman et al results

| Patient ID | A | B | C | D | E |
|---|---|---|---|---|---|
| 6-6 | 85.3 | 13.3 | - | 1.4 | - |
| 6-8 | 84.4 | 14.2 | - | 1.4 | - |
| 8-6 | 82.2 | 15 | - | 2.8 | - |
| 8-8 | 90 | 9.8 | - | 0.2 | - |

Fig. 9

Clarke's - EGA for one hour prediction (%)

| Patient ID | A | B | C | D | E |
|---|---|---|---|---|---|
| Subject1 | 81 | 17.2 | 0.2 | 1.7 | - |
| Subject2 | 72.56 | 26.69 | 0.75 | - | - |
| Subject3 | 67.53 | 29.86 | 0.35 | 2.26 | - |
| Subject4 | 71.84 | 23.75 | - | 4.41 | - |
| Subject5 | 71.03 | 26.82 | 0.67 | 0.89 | 0.78 |
| Subject6 | 82.06 | 16.81 | 0.28 | 0.85 | - |
| Subject7 | 81.69 | 17.36 | - | 0.98 | - |
| Subject8 | 76.09 | 22.46 | - | 1.45 | - |
| Subject9 | 84.88 | 15.12 | - | - | - |
| Subject10 | 82.9 | 16.57 | 0.12 | 0.35 | 0.06 |
| Subject11 | 76.89 | 21.78 | - | 1.33 | - |

Comparison with Reifman et al results

| Patient ID | A | B | C | D | E |
|---|---|---|---|---|---|
| 6-6 | 66.2 | 31.1 | 0.6 | 2.1 | - |
| 6-8 | 64.2 | 32.5 | 0.2 | 3.1 | - |
| 8-6 | 60.7 | 32.9 | 0.8 | 5.4 | - |
| 8-8 | 72.9 | 25.1 | - | 2.0 | - |

Fig. 10

| Patient ID | BG<70 mg/dL | | | BG 70-180 mg/dL | | | BG>=180 mg/dL | | |
|---|---|---|---|---|---|---|---|---|---|
| | Accurate | Benign | Error | Accurate | Benign | Error | Accurate | Benign | Error |
| Subject 12 | — | — | — | 90.61 | 1.39 | — | 94.44 | 5.56 | — |
| Subject 13 | 100 | — | — | 82.86 | 15.86 | 1.43 | 100 | — | — |
| Subject 14 | 100 | — | — | 91.82 | 3.13 | 5 | 95.56 | 2.22 | 2.22 |
| Subject 15 | 84.62 | 15.38 | — | 80.34 | 10.83 | 8.52 | 76.67 | 16.13 | 7.27 |
| Subject 16 | 85.71 | 14.29 | — | 75.58 | 10.82 | 13.61 | 87.78 | 3.22 | 8.97 |
| Subject 17 | 100 | — | — | 95.24 | 3.83 | 1.05 | 100 | — | — |
| Average | 90.89 | 4.94 | 4.17 | 86.04 | 9.33 | 8.73 | 91.36 | 4.52 | 4.13 |

Fig. 11

| Patient ID | BG<=70 mg/dL | | | BG 70-180 mg/dL | | | BG>=180 mg/dL | | |
|---|---|---|---|---|---|---|---|---|---|
| | Accurate | Benign | Error | Accurate | Benign | Error | Accurate | Benign | Error |
| Subject 12 | 84.21 | — | 15.79 | 100 | — | — | 94.97 | — | 5.03 |
| Subject 13 | 100 | — | — | 80.82 | 13.64 | 5.55 | 93.74 | 6.06 | — |
| Subject 14 | 100 | — | — | 80.55 | 14.5 | 5.17 | 95.77 | 2.13 | 2.13 |
| Subject 15 | 75 | 16.67 | 8.33 | 76.35 | 33.53 | 10.12 | 72 | 16.67 | 13.33 |
| Subject 16 | 85.71 | 14.29 | — | 73.07 | 24.33 | 2.7 | 81.48 | — | 18.52 |
| Subject 17 | — | — | — | 93.38 | 5.02 | 1.12 | 100 | — | — |
| Average | 90.82 | 5.16 | 4.02 | 83.96 | 13.05 | 3.99 | 90.57 | 4.12 | 5.31 |

*Fig. 12*

| Patient ID | BG<=70 mg/dL | | | BG 70-180 mg/dL | | | BG>=180 mg/dL | | |
|---|---|---|---|---|---|---|---|---|---|
| | Accurate | Benign | Error | Accurate | Benign | Error | Accurate | Benign | Error |
| Subject 11 | 78.95 | 0 | 21.05 | 90.13 | 8.7 | 0 | 96.77 | 0 | 3.23 |
| Subject 13 | 81.82 | 0 | 18.18 | 80.65 | 19.35 | 0 | 100 | 0 | 0 |
| Subject 14 | 100 | 0 | 0 | 82.45 | 17.55 | 0 | 96.08 | 0 | 3.92 |
| Subject 15 | 90.91 | 8.56 | 0.53 | 80.42 | 11.23 | 8.35 | 89.60 | 8.0 | 2.40 |
| Subject 16 | 74.19 | 11.92 | 13.89 | 79.92 | 20.21 | 2.56 | 98.4 | 0 | 1.6 |
| Subject 17 | 100 | 0 | 0 | 90.31 | 9.69 | 0 | 100 | 0 | 0 |
| Average | 87.75 | 3.16 | 11.09 | 83.78 | 16.08 | 1.81 | 96.81 | 1.33 | 1.86 |

Fig. 13

| Patient Id | BG≤70 mg/dL | | | BG 70-100 mg/dL | | | BG≥100 mg/dL | | |
|---|---|---|---|---|---|---|---|---|---|
| | Accurate | Benign | Error | Accurate | Benign | Error | Accurate | Benign | Error |
| Subject12 | 75 | 0 | 25 | 100 | 0 | 0 | 89.19 | 2.7 | 8.11 |
| Subject13 | 91.67 | 8.33 | 0 | 91.78 | 8.22 | 0 | 94.74 | 5.26 | 0 |
| Subject14 | 100 | 0 | 0 | 82.57 | 10.24 | 1.09 | 95.77 | 1 | 4.23 |
| Subject15 | 87.91 | 10.99 | 1.1 | 82.57 | 11.24 | 1.09 | 72.14 | 1.9 | 25.96 |
| Subject16 | 87.71 | 11.29 | 0 | 68.85 | 13.79 | 3.36 | 76.19 | 2.98 | 20.83 |
| Subject17 | 100 | 0 | 0 | 91.39 | 6.81 | 1.8 | 100 | 0 | 0 |
| Average | 90.63 | 5.15 | 4.17 | 89.39 | 9.03 | 1.57 | 88.88 | 5.64 | 5.48 |

Fig. 14

|  | BG < 70 mg/dL (%) | BG 70-180 mg/dL (%) | BG > 180 mg/dL (%) |
|---|---|---|---|
| Patient ID |  | Acc. Benign Error | Acc. Benign Error |
| Subject 1 | - | 100 - - | 100 - - |
| Subject 2 | - | 100 - - | 100 - - |

Fig. 17

|  | BG < 70 mg/dL (%) | BG 70-180 mg/dL (%) | BG > 180 mg/dL (%) |
|---|---|---|---|
| Patient ID | Acc. Benign Error | Acc. Benign Error | Acc. Benign Error |
| Subject 2 | - - - | 100 - - | - - - |
| Subject 5 | - - - | - - - | 80 6.67 13.33 |

Fig. 18

|  | BG < 70 mg/dL (%) | BG 70-180 mg/dL (%) | BG > 180 mg/dL (%) |
|---|---|---|---|
| Patient ID | Acc. Benign Error | Acc. Benign Error | Acc. Benign Error |
| Subject 2 | - - - | 96.86 3.12 - | - - - |
| Subject 5 | - - - | - - - | 53.33 26.67 20 |

Fig. 19

|  | Special event training predictor (%) | Blind Predictor (%) |
|---|---|---|
| Patient ID | A B C D E | A B C D E |
| Subject 2 | 90.63 9.38 - - - | 87.5 12.5 - - - |
| Subject 5 | 93.75 6.25 - - - | 50 50 - - - |

Fig. 20

GLUCOSE PREDICTOR BASED ON REGULARIZATION NETWORKS WITH ADAPTIVELY CHOSEN KERNELS AND REGULARIZATION PARAMETERS

CROSS-REFERENCE TO RELATED APPLICATIONS

This application is a 35 U.S.C. § 371 National Stage application of International Application PCT/EP2012/057260 (WO2012/143505), filed Apr. 20, 2012, which claimed priority of European Patent Application 11163219.6, filed Apr. 20, 2011; this application claims priority under 35 U.S.C. § 119 of U.S. Provisional Application 61/481,315; filed May 2, 2011.

FIELD OF THE INVENTION

The present invention relates to a method for predicting a glycaemic state of a subject on the basis of past physiologic measurements and/or therapeutic action, as well as to a device capable of executing such a prediction.

BACKGROUND OF THE INVENTION

People with diabetes, especially those suffering from Type 1 or juvenile diabetes, ought to measure their glucose levels frequently in order to be able to adjust treatment or behaviour to maximise time spent in normoglycaemia. Traditionally, glucose levels are measured manually by means of specialised glucose monitoring equipment comprising a lancet, glucose test strips and a dedicated metering device. During one such measurement the user punctuates the skin, typically on a finger, and obtains a small drop of blood which is placed onto a test strip. The test strip is then read by the blood glucose meter and after a few seconds the meter displays the result. The finger lancing can be quite painful and to repeat this procedure multiple times during the day is highly undesirable. Furthermore, since the user has to use, and bring around, three different system parts in order to carry out a measurement this form of glucose monitoring is viewed as a nuisance by most people with diabetes.

Recent advances in sensor technology have led to the development of wearable continuous glucose monitoring systems, also known as CGM systems, which are able to measure and display tissue glucose levels continuously (or near-continuously). These systems generally comprise a skin adhesive patch carrying a small sensor adapted for percutaneous placement, a sensor insertion applicator, wireless communication means, and a hand-held remote receiver device capable of interpreting the sensor signals and presenting the results. The sensors can be used for five to seven days and are subsequently discarded. In the course of these five to seven days the sensors need only be calibrated (using blood glucose measurements obtained manually) a couple of times per day or less, depending on the particular sensor brand.

CGM systems prospectively offer superior user convenience in comparison with conventional blood glucose monitoring equipment, partly because of the reduced requirement for performing painful and cumbersome fingerstick measurements, and partly because the measurements are performed automatically and processed continuously, thereby ensuring that dangerous glucose excursions are detected and the user is alerted to them in time. However, the currently marketed systems are only cleared for use in conjunction with conventional blood glucose testing and so the manual glucose testing is in principle not much reduced.

Furthermore, even though it is possible for glucose monitoring systems to provide real-time test results it remains desirable to more reliably predict glucose level fluctuations in the near future, e.g. half an hour or an hour ahead.

Estimation of future glucose concentrations is a crucial task for diabetes management since a projected picture of the glycaemic state of a person will be an invaluable help in relation to minimising glucose excursions and avoiding dangerous hypoglycaemic events. Continuous glucose monitoring provides detailed insight into glucose variations, and several methods have been developed recently for glucose prediction from CGM data, e.g. as presented in Sparacino et al.: "*Glucose concentration can be predicted ahead in time from continuous glucose monitoring sensor time-series*", IEEE Trans. on Biomedical Eng., 54(5): 931-937, 2007, Reifman et al.: "*Predictive Monitoring for Improved Management of Glucose Levels*", Journal of Diabetes Sci. and Tech., 1(4): 478-486, 2007, Zanderigo et al.: "*Glucose prediction algorithms from continuous monitoring data: Assessment of accuracy via Continuous Glucose Error-Grid Analysis*", Journal of Diabetes Sci. and Tech., 1(5): 645-651, 2007, and Eren-Oruklu et al. "*Estimation of future glucose concentrations with subject-specific recursive linear models*", Diabetes Technology & Therapeutics, 11(4): 243-253, 2009.

All these methods are based on time-series identification methodology and differ only in type and complexity of identified time-series models such as polynomial models, autoregressive models (AR), autoregressive moving average (ARMA) models, or other models from the MATLAB system Identification Toolbox.

In essence, in a model of a fixed type, model parameters are fitted at each sampling time against past glucose data. Then, the fitted model is iteratively used to predict the glucose level for a given prediction horizon (PH).

In a number of aspects time-series models appear rigid and in practice less suitable for the purpose of predicting future glucose concentrations, e.g. because such models need both frequent and consistent data input. This entails a high involvement of the user, e.g. via frequent glucose testing operations, and/or a need for an automatic glucose monitoring apparatus which is capable of conveying sampled data frequently and in a highly reliable manner. Therefore, from a user convenience point of view it is desirable to develop a glucose prediction method which neither requires a high sampling rate nor regularly sampled data.

There are several publications in the patent literature disclosing diabetes management systems, which comprise patient operated apparatuses programmed to predict the patient's future blood glucose values. A high reliability of the prediction is crucial for all such systems. In WO 2005/041103 an improvement of the reliability is achieved by providing a plurality of mathematical models, each adapted to generate a respective prediction from the same input. It is desirable that this plurality of mathematical models comprises at least two models based on different approaches.

At the moment all known and justified prediction models in CGM systems are based on a time-series approach or linear extrapolation. Even more, as also mentioned in Kovatchev and Clarke: "*Peculiarities of the Continuous Glucose Monitoring Data Stream and Their Impact on Developing Closed-Loop Control Technology*", Journal of Diabetes Sci. and Tech., 2(1): 158-163, 2008, in CGM systems practically all predictions are currently based on a linear extrapolation of glucose values. In view of the above, it is therefore, from a medical device point of view, desirable to develop a different approach to glucose prediction.

A good prediction of near future glucose levels is strongly desirable since it will enable the user to be alerted to potentially dangerous situations well in advance of any events happening, and to perform preventive actions to avoid spending too much time outside normoglycaemia. This could in turn further reduce, or perhaps even eliminate, the need for painful manual blood glucose check measurements.

SUMMARY OF THE INVENTION

Having regard to the above mentioned problems and deficiencies, it is an object of the invention to provide a glucose predictor which is able to predict the future glycaemic state of a subject on the basis of irregularly sampled data.

It is a further object of the invention to provide a glucose predictor which is able to predict the future glycaemic state of a subject on the basis of data obtained with a low sampling rate.

It is an even further object of the invention to provide a glucose prediction model which is an alternative to time-series or linear extrapolation based glucose prediction models.

In the disclosure of the present invention, aspects and embodiments will be described which will address one or more of the above objects or which will address objects apparent from the below disclosure as well as from the description of exemplary embodiments.

In a first aspect of the invention a computer-implemented method for predicting a glycaemic state of a subject is provided, comprising: i) receiving information indicative of a physiologic condition of the subject and/or information related to a therapeutic treatment, ii) specifying a functional space for a prediction on the basis of at least some of the information received under i), and iii) specifying in the functional space predicted glucose levels as a continuous function of time. Step iii) may comprise specifying blood glucose and/or tissue glucose levels as a continuous function of time.

In the present context, the term "glycaemic state" should be taken to include at least a specified blood or tissue glucose concentration at a given point in time. It is noted, however, that "glycaemic state" may additionally comprise glucose trend indication providing information about the change and/or the rate of change of the glucose level at the given point in time.

Information indicative of a physiologic condition of the subject may comprise information related to past measurements of at least one body characteristic, such as sensor based blood or tissue glucose measurements. Alternatively, or additionally, it may comprise information related to other measured parameters such as heart rate, skin temperature, skin impedance, respiration, etc.

Information related to a therapeutic treatment may comprise information related to a previous administration of a glucose regulating substance, such as e.g. insulin, glp-1 or glucagon. This information may comprise the time of administration, the specific type of substance (e.g. fast acting insulin) administered, the amount administered, e.g. in terms of International Units (IU), mg or ml, and/or the specific site of administration.

The above method for predicting a glycaemic state of a subject may further comprise, in addition to receiving information indicative of a physiologic condition of the subject and/or information related to a therapeutic treatment, receiving exercise data and/or information related to food consumption. The exercise data may e.g. comprise time, type and/or duration of exercise or simply an estimation of calories burned. The information related to food consumption may e.g. comprise time and amount of food intake, e.g. an estimation of calories consumed.

The present approach is inspired by Learning Theory and in the Theory of Inverse and Illposed problems. Systematic mathematical research in the borderline area between these disciplines has been started only recently (see, e.g., Bauer et al.: "*On regularization algorithms in learning theory*", Journal of Complexity, 23: 52-72, 2007). Mathematically, the proposed predictor extrapolates glucose values from a small number of glucose measurements made before the moment of a prediction.

Embodiments of the present invention may predict blood glucose values ahead of time, i.e. blood glucose at points in time equal to or later than the time of the last actual measurement used in the prediction process. Hence the blood glucose prediction described herein may predict a future glycaemic state, e.g. a future blood glucose value.

In accordance with embodiments of the method described herein such a predictor is comprised of two learning machines. One of them, a supervising or main learning machine, is trained in choosing an adequate functional space, where the extrapolation will be made and from which an adequate extrapolating function may be selected. The other machine, a supervised learning machine, is trained in constructing a function from a given functional space. The latter machine may present a future glucose profile and may be constructed by a data-driven regularization algorithm performed in the space suggested by the supervising machine. Both machines may be constructed in the form of regularization networks with adaptively chosen kernels and regularization parameters. Hence, the prediction process comprises two stages: a first stage implemented by the main learning machine and a second stage implemented by the supervised learning machine. The first stage will also be referred to as prediction setting stage while the second stage will also be referred to as prediction execution stage. The main learning machine employed during the prediction setting stage of the prediction process may be trained during a training process. Embodiments of the training process are based on a data pool of measured physiological states and results in a specification of the main learning machine. In some embodiments, the training process is performed only once, and the resulting specification of the main learning machine remains unchanged during subsequent multiple executions of the prediction process. In other embodiments, the training process may be continued, e.g. based on new measurements included in an updated data pool and/or based on results of the subsequent prediction process, so as to continuously improve the main learning machine. The training process may be performed by a data processing system equal to or different from the prediction device that implements the prediction process.

Embodiments of the prediction process disclosed herein are advantageous in several ways compared to prediction models based on time-series analysis. For example, embodiments of the method, e.g. the adaptive regularization network, produce a prediction in the form of a function describing a future glucose profile, while time-series predictors give finite sequences of future glucose values. Specifying a predicted future glycaemic state as a continuous function of time instead of as a collection of discrete values provides for a better overview of glucose fluctuations within the prediction horizon. This allows, among other things, more precise alarm/alert features to be incorporated in, e.g., a continuous glucose monitoring system or a partly automated diabetes management system.

Further, for the identification of a time-series prediction model one needs chronologically ordered past glucose data with a sufficiently small sampling rate (e.g. with a sampling interval of 1 or 3 minutes), while adaptive regularization networks can be trained with the use of "piece-wise data" that have essential time gaps in measurements. Such essential time gaps in measurements are not unusual in practice since users sometimes forget to perform a glucose test. Furthermore, temporary malfunctions of automatic measurement systems, such as continuous glucose measurement systems, may occur. When only piece-wise data is required the prediction model will not be corrupted due to a low and/or irregular sampling rate.

Even further, the design of adaptive regularization networks can be easily adjusted for making predictions after special events, e.g. after breakfast, when new factors influencing the glucose level should be taken into account. In such cases a new regularization network can merely be added in the main learning machine, and this network can be trained independently of others. For time-series prediction models an incorporation of a new factor would mean an increase of the input dimensionality that completely changes the form of the model.

An embodiment of a training process of a method described herein may specifically comprise selecting (e.g. heuristically) input data segments (glucose measurements and possibly other input data types) which have sufficient variance and which therefore have dynamics which are desirable for the predictor to learn from and emulate. Other variation measurements such as mean absolute derivation (MAD) or a quota system to ensure that input data representing important base classes are included may alternatively be employed. Hence, in some embodiments of a training process, the method comprises selecting input data segments that have a predetermined variation measurement larger than the predetermined threshold.

Further, in some embodiments, the method comprises compressing the input data segments to deal with irregularly sampled input data. This may comprise performing a linear fit on each data segment, thereby performing a linear regression to minimise the residuals between data points and a best fit line. The data may then be compressed into the two coefficients which specify the line, the slope and the intercept. Alternatively, the data segments may be compressed to statistical parameters like mean and standard deviation or by performing a non-linear curve fit. For the purpose of the present description, the parameters defining the compressed input segments, e.g. the parameters of the linear fit or the statistical parameters, will also be referred to as labels that label the respective input data segments.

An error or cost function may then be defined that describes proper behaviour of the predictor in terms of the problem domain, e.g. a measure of deviation between predicted glucose values and measured glucose values. Realising that hypo- and hyperglycaemic events are more important for the predictor than the intermediate normoglycaemia range a piece-wise non-linear cost function may be designed which assigns a very high error to inaccurate hypo- and hyperglycaemia predictions, while a sliding error scale may be used to penalise inaccurate predictions in the intermediate range. Alternatively, an asymmetric penalty curve that penalises inaccuracy in the hypoglycaemia area more than inaccuracy in the hyperglycaemia area, or a manual process involving clinician input, may be chosen.

The defined error function may be expressed in terms of a Tikhonov-type functional which is minimised over a reproducing kernel Hilbert space. This functional depends on a Tikhonov regularization parameter which may be tuned adaptively using the quasi-balancing principle, or, alternatively, using other methods such as cross-validation or the balancing principle. If e.g. no regularization is applied (i.e. the regularization parameter equals zero) then the solution depends on the inverse of the kernel. This kernel is often ill-conditioned or non-invertible, in part because of dependencies within the input data. One way to solve this is to shift the eigenvalues of the kernel matrix away from zero which is done by adding a small shift. If the shift is too small then the kernel will remain nearly ill-conditioned and for numerical reasons a solution will not be found. If on the other hand the shift is too large then the solution will be altered by an unacceptable amount thus injecting error. The approximate optimal magnitude of the regularization parameter may, according to the quasi-balancing principle (which does not require any a priori knowledge of the predictor), be determined by starting with an unacceptably small value of the regularization parameter and then gradually increase this by e.g. an exponential factor over a certain range in a geometric sequence. Whereas a more exact solution requires all pair-wise comparisons of predictor evaluations with values of the regularization parameter, the quasi-balancing principle decreases the computational costs by involving only pair-wise comparisons between consecutive solutions.

In some embodiments the predictor is a function of the kernel and the initial regularization parameter. The kernel may be parameterised by one or more kernel parameters. For a given set of kernel parameters the kernel may be calculated and using the quasi-balancing principle and the kernel specific coefficients the predictor function may be determined. A summation over these coefficients and the kernel over the desired future times gives predicted glucose values for that particular set of kernel parameters.

During embodiments of the training process, the predicted glucose value may then be compared against the actual value and assigned an error in order to find the best set of kernel and regularization parameters for a given input data segment from a data pool of training data segments, e.g. in a way that minimizes the risk of missing a prediction of hypo- and hyperglycemia. A direct search may be used to do this, or, alternatively, optimisation methods like e.g. the Nealder-Mead and conjugate-gradient methods.

Next, during embodiments of the training process, a trained non-linear relationship between compressed data segments as input and the best kernel and regularization parameter values as output may be created. In some embodiments, the trained non-linear relationship is constructed by a data-driven regularization algorithm, e.g. by minimising an error function expressed in terms of a Tikhonov-type functional which is minimised over a reproducing kernel Hilbert space. The non-linear mapping may be defined by a set of kernels, each defined by a set of kernel parameters, and by a set of compressed training data segments. The error function may be indicative of a deviation (using a suitable distance measure) between the determined best kernel parameters for a set of compressed testing data segments and the kernel parameters generated by the non-linear relationship from the set of compressed testing data segments. Thereby, testing data segments from the data pool are used as the input and the kernel parameters of the main learning machine are found so as to minimize an indicative error function. Alternatively, a non-linear machine capable of generalising the relationship between the input data segments and the training kernel parameters may be constructed using neural networks or support vector machines. The choice of coefficients determining the kernels in the main learning machine may in some embodiments not necessarily be unique, which is not crucial, since the prediction based on these kernels may employ a regularization that has a special regularization parameter aimed, in particular, at decreasing the sensitivity to non-uniqueness.

During the prediction setting stage of embodiments of the prediction process, the trained non-linear relationship between compressed data segments and desired parameters created in the main learning machine is used to determine the kernel parameters and the regularization parameter for the final kernel to be used in the prediction execution stage of the prediction process. These parameters are specific to the data, but need not be trained specific to a patient, i.e. the prediction setting stage as described in the above specifies a functional space for a prediction which can be employed independently of the individual user. Input data from personal sensors, such as a CGM sensor, a BG sensor, a heart rate sensor etc., from a drug delivery device and/or from user provided meal information are now received for a specific user and compressed using, e.g., a linear fit on each data segment. The compressed data are run through the above mentioned non-linear relationship created during the training process in the main learning machine to produce the parameters for the final, predictor kernel, and the predictor itself is subsequently constructed on the basis thereof enabling a calculation of predicted glucose values as a continuous function of time.

A highly accurate glucose prediction over a period of up to one hour ahead of time, as obtainable with a glucose predictor of the present invention, will enable timely preventive or corrective action, either by the involved person or by a suitable automated/semi-automated control system, and thereby ensure a larger percentage of time spent by that person in normoglycaemia, ultimately leading to increased safety, later onset of chronic complications of diabetes, and lowered health care costs.

The present invention relates to different aspects including the method described above and in the following, and further methods, devices, and/or product means, each yielding one or more of the benefits and advantages described in connection with the first mentioned aspect, and each having one or more embodiments corresponding to the embodiments described in connection with the first mentioned aspect and/or disclosed in the appended claims.

In a second aspect of the invention a glucose prediction device is provided, comprising: input means adapted to receive information indicative of a physiologic condition of a subject, processing means adapted to predict a glycaemic state of the subject on the basis of at least some of the information received by the input means, and output means adapted to convey information related to the predicted glycaemic state. The processing means may employ a multistage algorithm comprising a prediction setting stage which specifies a functional space for the prediction and a prediction execution stage which specifies a predicted glycaemic state, e.g. predicted future blood and/or tissue glucose values, of the subject in the functional space as a continuous function of time.

The prediction setting stage may specify a functional space for the prediction through a compression of input data segments and a determination of a kernel and an initial regularization parameter. The input data segments may be selected input data from one or more glucose sensors and/or from other personal physiologic sensors measuring body parameters such as heart rate, respiration, and skin temperature. Input data pertaining to the subject's therapeutic treatment, such as time and amount of a specific insulin type delivered or to be delivered, energy intake, and/or exercise routines may also be included. Each input data segment may comprise a plurality of input data records associated with respective points in time, and each input data record being indicative of one or more measurements and/or inputs. The compressed data segments may then form the basis for a suggestion of a kernel and an initial regularization parameter which are used in the prediction execution stage to construct the predictor. Generally, the processing means is capable of carrying out the various algorithm related procedures in accordance with the method for glycaemic state prediction described herein.

Each selected input data segment may be associated with some label, e.g. an element from some set of variables. For example, if data segments are given in the form of sequences of glucose measurements made in successive time moments, then the space of two dimensional vectors may be chosen as the set of labels. In this case a labelling may be performed by assigning to each input data segment the two coefficients of the best linear fit associated with these data. One more example of labelling, which is relevant in the context of this application, is related with the case when a selected input data segment is given in the form of sequence of glucose measurements made in successive time moments around insulin injection or meal time. This case is considered in the section "Extension of the predictor". Then a label for such a data segment may be given as a 3-dimensional vector, where the first two components e.g. are the coefficients of the best linear fit associated with glucose measurements, and the third component is the amount of injected insulin or meal intake.

The input means may comprise one or more manually operable keys, turn dials, push pads, touch screens and/or the like. Alternatively, or additionally, the input means may comprise a receiver, e.g. wireless, for reception of input data. A wireless communication may be automated, e.g. per request of the glucose prediction device itself or of one or more other apparatuses in a dedicated network, or it may be manually initiated by the user. The input means may even be physically integrated in a physiologic measurement device, thereby receiving input data directly from the device sensor.

The output means may comprise a graphic display, an alphanumeric display, and/or a speaker and may be adapted to present one or more pieces of information related to the predictions made by the processing means. Specifically, the output means may be adapted to present the predicted glycaemic state specified by the processing means as a continuous function of time and/or as discrete values or intervals within certain temporal boundaries. Alternatively, or additionally, the output means may comprise a transmitter, e.g. wireless, capable of communicating some or all of the processed information to a further device, e.g. a device with a display or a speaker.

In one embodiment the glucose prediction device is a separate device functioning independently of other devices. The glucose prediction device is a portable, preferably hand held, unit which receives relevant data from one or more external devices as well as manual input by a user, e.g. relating to fat and carbohydrate intake, and provides a processed output in the form of one or more numbers and graphs showing at least the predicted future glucose profile for a specific prediction horizon, e.g. 20 minutes, half an hour or one hour.

In another embodiment the glucose prediction device is incorporated in a drug delivery device such as an injection device, an infusion device or an inhalation device. The glucose prediction device receives data from one or more glucose sensors and uses the data together with relevant use data logged by the drug delivery device to predict a future glycaemic state of the subject, which can be presented at least as a glucose profile for a self-elected prediction horizon (e.g. between 0 and 1 hour) on an associated display. The associated display may be a display on the drug delivery device or on a separate display device. In the latter case the processed data from the drug delivery device may be transmitted wirelessly to the separate display device. Alternatively, the drug delivery device and the separate display device are connected by wire during the data transmission.

In yet another embodiment the glucose prediction device is incorporated in a dedicated communication device such as a remote controller for a drug delivery device, a remote monitor, a mobile phone, or a PDA. In a remote controller for an infusion pump, for example, the glucose prediction device receives use data wirelessly from the pump, tissue glucose data wirelessly from a CGM, and blood glucose data from manual user input. On the basis of these data a future glycaemic state is predicted and at least a glucose profile for a prediction horizon can be displayed on a built-in screen.

In a further embodiment the glucose prediction device is incorporated in a glucose measurement device, such as a continuous glucose monitor or a blood glucose meter. The glucose prediction device uses the data established by the glucose measurement device to predict a future glycaemic state of the subject. Results may be shown on a remotely located screen for the continuous glucose monitor or on the blood glucose meter display.

In a third aspect of the invention a system is provided, comprising: a glucose prediction device, body fluid parameter sensing equipment, a drug administration device and/or a body characteristic measurement device. Each system part may comprise means for transmission of data, e.g. a wireless transceiver, and the glucose predictor may be adapted to receive and process information from each other system part related to measurements performed in connection with the use of the specific system part. The glucose prediction device may comprise a processor adapted to specify a functional space for a prediction to be executed on the basis of some or all of the information received from the other system parts, and to specify, in the specified functional space, a predicted glycaemic state, e.g. predicted future glucose values, of a subject as a continuous function of time.

The body fluid parameter sensing equipment may comprise a continuous glucose monitor adapted to measure tissue glucose levels continuously or near-continuously, and/or a blood or interstitial fluid glucose meter adapted to be used for manual intermittent measurements of blood glucose or interstitial fluid glucose levels.

The drug administration device may comprise a drug injection device, such as an insulin pen, a drug infusion device, such as an insulin pump, or another type of device for administering a drug to the body. The drug administration device may further comprise electronics, e.g. for storing, processing and/or transmitting data pertaining to the use of the device.

The body characteristic measurement device may comprise a device capable of monitoring a physiologic parameter such as heart rate, skin temperature, skin impedance, respiration, or indeed any body characteristic the level or change of which may be associated with glucose excursions.

The glucose prediction device may be incorporated in any of the above mentioned devices or in a separate unit, such as a remote controller or remote monitor for such a device. Alternatively, the glucose prediction device is provided as a stand-alone device.

As mentioned above, continuous glucose monitoring systems, also known as CGM systems, generally comprise a sensor adapted to provide a sensor signal, e.g. a percutaneous electric current reading, and a receiver device capable of interpreting the sensor signals and presenting the results. It will be appreciated that it is desirable to provide a device and process that provides an accurate estimation of a glucose concentration based on the sensor signal.

Accordingly, in yet another aspect, a regularisation scheme disclosed herein is used to determine a glucose concentration from a sensor signal, e.g. from a subcutaneous electric current reading. The sensor signal may be obtained from a glucose meter such as a blood glucose meter or a continuous glucose monitor. The estimated glucose concentration may be an estimated blood glucose concentration or an estimated tissue glucose concentration. Embodiments of a method for determining a glucose concentration comprise:
  receiving a sensor signal, such as a subcutaneous electric current reading, of a subject,
  estimating a glucose concentration from the received sensor signal; wherein estimating comprises determining an estimated glucose concentration predictor function in a predetermined functional space as a continuous function of sensor signal values.

In some embodiments, the continuous function is determined from a kernel, a regularisation parameter, and a set of training data, the set of training data comprising sensor signal values and reference glucose concentrations, and wherein the kernel is determined from a set of kernels as an at least approximate minimizer of an error functional.

The continuous function of sensor signal values may be constructed by a regularized learning algorithm in a reproducing kernel Hilbert space.

The functional space for the prediction on may be determined on the basis of information obtained from a predetermined data pool comprising the set of training data. In particular, the error functional may be indicative of a deviation of estimated glucose concentrations and reference glucose concentrations from the set of training data. To this end, the set of training data may be split in two subsets, and determining the kernel may comprise:
a) selecting a kernel from the set of kernels
b) computing an estimated glucose concentration predictor function and a regularisation parameter from the selected kernel as a predictor function that minimizes a regularisation functional indicative of a regularised deviation of estimated glucose concentrations and reference glucose concentrations from a first subset of the set of training data;
c) computing an error functional as a weighted sum of the regularisation functional and a performance functional indicative of a regularised deviation of estimated glucose concentrations predicted by the computed predictor function, and reference glucose concentrations from a second subset of the set of training data, different from the first subset; and
d) repeating steps a) through c) within a minimization procedure to determine a kernel that at least approximately minimizes the error functional.

Embodiments of the above method for determining a glucose concentration may be performed by a processing device, e.g. a continuous glucose measurement device, comprising: input means for receiving sensor signals, processing means adapted to perform the steps of en embodiment of the method for determining a glucose concentration described herein, and output means for outputting the determined glucose concentration.

In the present specification reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in at least that one aspect or embodiment of the invention, but not necessarily in all aspects or embodiments of the invention. It is emphasized, however, that any combination of features, structures and/or characteristics described in relation to the invention is encompassed by the invention unless expressly stated herein or clearly contradicted by context.

In the present specification, reference is made to minimisation of error or cost functions. It will be appreciated that such minimisation may be performed using numerical optimisation methods known as such in the art. It will further be appreciated that such numerical minimisation of error or cost functions typically results in an approximate minimisation, normally defined by a suitable completion criterion of the numerical optimisation process in question. Consequently, the terms minimising and minimisation as used herein are intended to include approximate minimisation achieved by such numerical minimisation methods.

BRIEF DESCRIPTION OF THE DRAWINGS

In the following the invention will be further described with references to the drawings, wherein FIG. 5 is a table presenting the results of CG-EGA for an adaptive predictor for a specific patient ID, when predictions are made with a prediction horizon of 30 minutes, FIG. 6 is a table showing comparative results of CG-EGA for a specific CGM system, FIG. 7 is a table presenting the results of CG-EGA for 11 patients with a prediction horizon of 30 minutes, FIG. 8 is a table presenting a comparison, in terms of Clarke's EGA, between the performance of a predictor according to an embodiment of the invention and a CGM sensor, FIGS. 9 and 10 are tables presenting a comparison, in terms of Clarke's EGA, between the performance of a predictor according to an embodiment of the invention and a predictor based on time-series analysis, within a prediction horizon of 30 minutes, respectively one hour, FIG. 11 is a table presenting the results of PRED-EGA for 6 patients with a prediction horizon of 0 minutes, FIG. 12 is a table presenting the results of PRED-EGA for 6 patients with a prediction horizon of 10 minutes, FIG. 13 is a table presenting the results of PRED-EGA for 6 patients with a prediction horizon of 20 minutes, FIG. 14 is a table presenting the results of the PRED-EGA for 6 patients with Seven® Plus CGM viewed as oracle predictors, FIG. 17 presents CG-EGA results for considered special event predictions, FIG. 18 presents the performance of a special event training predictor according to an embodiment of the invention using CG-EGA, FIG. 19 presents the performance of a blind predictor using CG-EGA, FIG. 20 presents comparative results from performances, in terms of Clarke's EGA, of a special event training predictor according to an embodiment of the invention and a blind predictor.

In the figures like structures are mainly identified by like reference numerals. It is noted that the shown figures are schematic representations for which reason the configuration of the different structures as well as their relative dimensions are intended to serve illustrative purposes only.

DESCRIPTION OF EXEMPLARY EMBODIMENTS

Figure 1A:
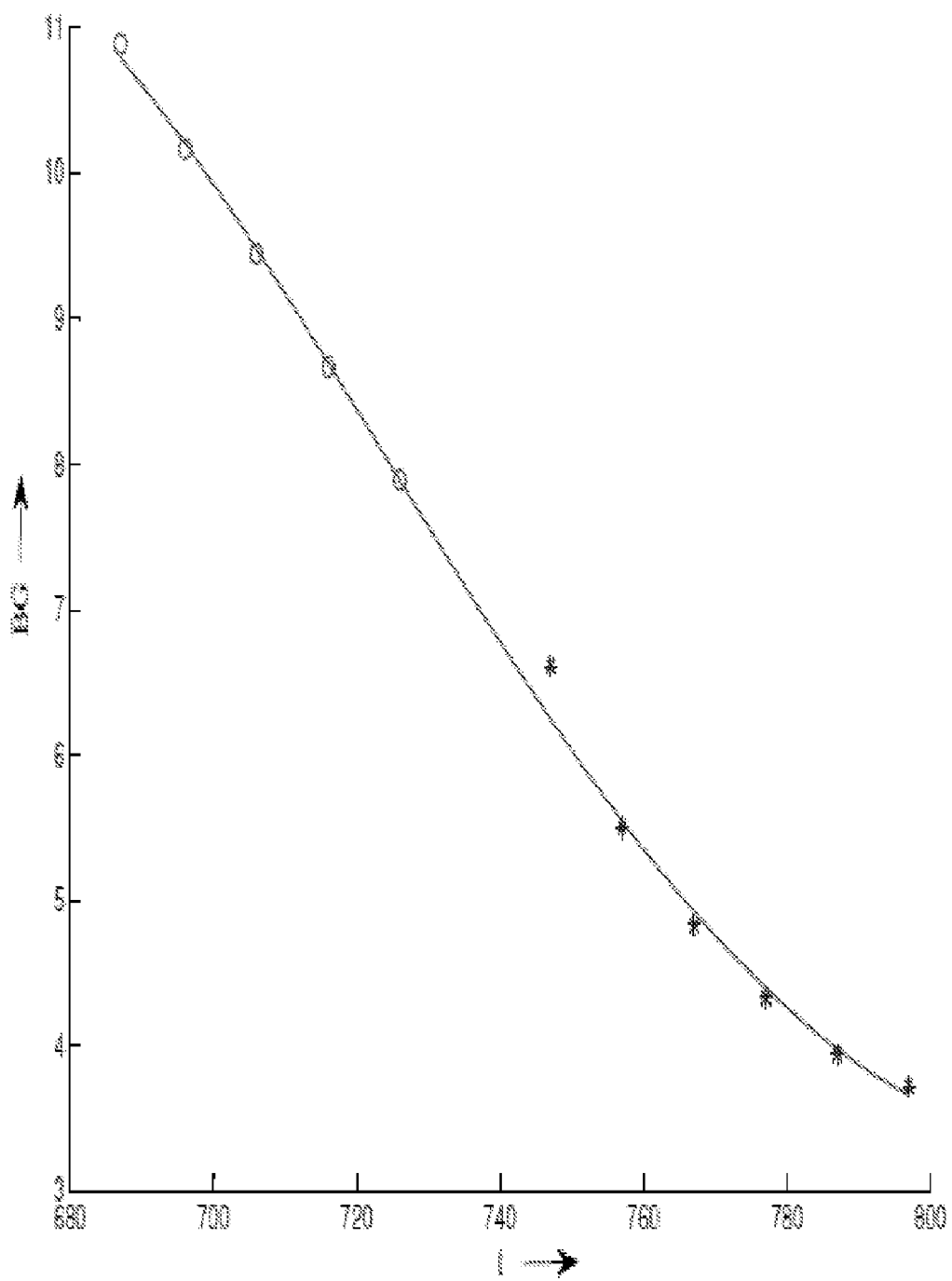
FIGS. 1a and 1b show the examples of subsequent measurements of the subject's blood glucose concentration that are used for training a predictor according to an embodiment of the invention, as well as the graphs interpreted as prediction traces.

For the purpose of the present description, it is initially assumed that for a particular subject m-subsequent measurements of the subject's blood glucose concentration $y_i$ at time moments $t=t_i$, $i=1, 2, \ldots, m$, are given. In the following an embodiment of a process for constructing a predictor is described in detail where the predictor will use these past measurements $\{y_i\}_{i=1}^{m}$ to predict a future blood glucose concentration for the subject in a time interval from $t=t_m$ till $t=t_m+PH$, where PH is a prediction horizon. Prediction will be done in the form of a continuous function of time $y=y(t)$, for $t \in [t_m, t_m+PH]$.

Data Pool

To construct such a predictor a Data Pool consisting of records of blood glucose (BG) measurements previously performed with the same or with another subject is used. It could be, for example, clinical records of BG concentrations $y_j^{(\mu)}$ sampled at time moments $t=t_j^{(\mu)}$ during the $\mu^{th}$ day of a clinical trial. It could also be CGM-measurements collected by the subject. Alternatively, a Data Pool may comprise records of blood glucose (BG) measurements previously performed with multiple subjects. Generally, for the purpose of the present description, a Data Pool is assumed to comprise Q data segments $\{(t_j^{(\mu)}, y_j^{(\mu)})\}$, $\mu=1, \ldots, Q$.

In some embodiments, certain requirements may be imposed on a Data Pool. Possible requirements to a Data Pool $\{(t_j^{(\mu)}, y_j^{(\mu)})\}$ are that:

each segment $(t_j^{(\mu)}, y_j^{(\mu)})$, $j=p, p+1, \ldots, P$ should be "long enough" such that a time interval $[t_p^{(\mu)}, t_P^{(\mu)}]$ is longer than a time interval $[t_m, t_m+PH]$ in which the predictor is expected to operate, namely, data $\{y_i\}$ for prediction are collected during the period $[t_1, t_m]$, and a prediction is made for time $[t_m, t_m+PH]$; and it is expected that Data Pool $\{(t_j^{(\mu)}, y_j^{(\mu)})\}$ contains hyper- and hypoglycaemia events such that there is an essential amount of data $(t_j^{(\mu)}, y_j^{(\mu)})$ with $y_j^{(\mu)} > 180$ mg/dl and $y_j^{(\mu)} < 70$ mg/dl.

From Data Pool to Training Set

Informative pieces are selected from the Data Pool to form a training set, and the selection procedure is the following:

1) For some $p=1, 2, \ldots$, consider a piece $(t_j^{(\mu)}, y_j^{(\mu)})_{j=p}^{m+p-1}$ from the Data Pool. Each such a piece contains the same number of measurements, namely, (m+l), and it is assumed that the length of the interval $[t_{m+p-1}^{(\mu)}, t_{m+l+p-1}^{(\mu)}]$ is not less than PH. To simplify the description it is assumed that $t_{m+l+p-1}^{(\mu)} - t_{m+p-1}^{(\mu)} = PH$.

2) Find a linear (polynomial) fit $a_p^{(\mu)} t + b_p^{(\mu)}$ for $(t_j^{(\mu)}, y_j^{(\mu)})_{j=p}^{m+p-1}$, where the value $a_p^{(\mu)}$ inherits a variance of $\{y_j^{(\mu)}\}_{j=p}^{m+p-1}$, while $b_p^{(\mu)}$ reflects the level of the BG value in the time interval $[t_p^{(\mu)}, t_{m+p-1}^{(\mu)}]$. Thus, the main features of $(t_j^{(\mu)}, y_{j(\mu)})_{j=p}^{m+p-1}$ are captured in $(a_p^{(\mu)}, b_p^{(\mu)})$. Alternatively, other methods of feature extraction may be performed, e.g. polynomial fits other than linear fits, e.g. a fit by a higher-order polynomial.

3) In this context a piece $(t_j^{(\mu)}, y_j^{(\mu)})_{j=p}^{m+p-1}$ is said not to be informative if there is no essential change in BG values $(y_j^{(\mu)})_{j=p}^{m+p-1}$. In other words the subject is in a stable situation. This scenario is captured in the value $a_p^{(\mu)}$. Hence one can fix a threshold value $\theta$ for $a_p^{(\mu)}$ to determine whether $(t_j^{(\mu)}, y_j^{(\mu)})_{j=p}^{m+p-1}$ is informative or not, and the threshold value may depend on the subject. More precisely, a piece $(t_j^{(\mu)}, y_j^{(\mu)})_{j=p}^{m+p-1}$ is said to be informative, if the corresponding coefficient $a_p^{(\mu)}$ in the linear fit satisfies the inequality $|a_p^{(\mu)}| \geq \theta$. In the present experiments with 11 subjects, the threshold was fixed as $\theta=0.019$ for eight of them, and $\theta=0.017$ was used for other four subjects.

4) Take from the Data Pool all pieces of the form $(t_j^{(\mu)}, y_j^{(\mu)})_{j=p}^{m+l+p-1}$ such that $(t_j^{(\mu)}, y_j^{(\mu)})_{j=p}^{m+p-1}$ are informative.

Figure 1B:
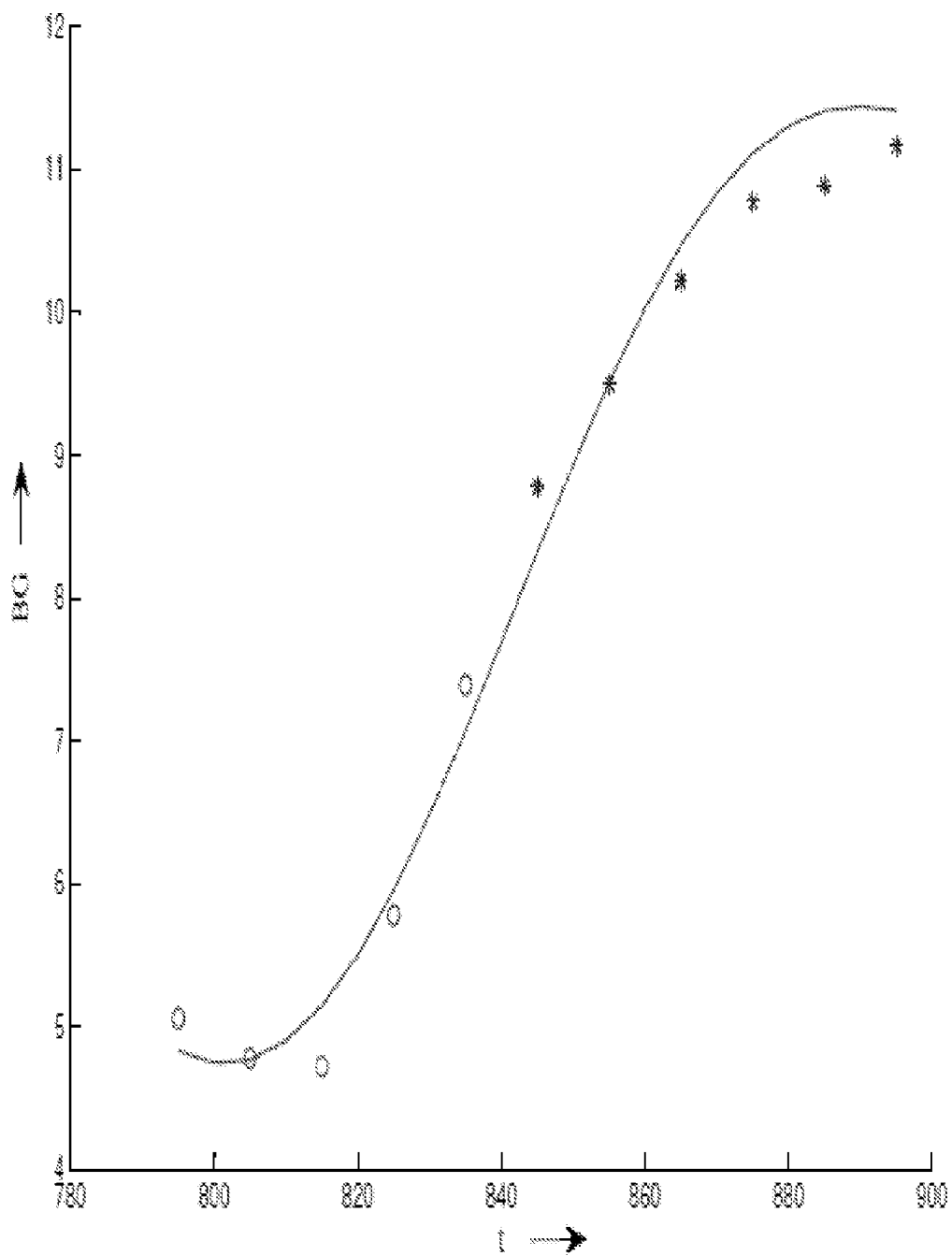

Now, the new Data Pool contains only pieces $(t_j^{(\mu)}, y_j^{(\mu)})_{j=p}^{m+l+p-1}$ with informative parts, $(t_j^{(\mu)}, y_j^{(\mu)})_{j=p}^{m+p-1}$. Examples of two such pieces corresponding to hypo- and hyperglycaemia events are shown in FIGS. 1a and 1b respectively. These pieces were selected from the Data Pool consisting of records of CGM-measurements taken from a particular subject (Patient ID: Subject4). Points from informative parts are marked by circles (o). In the figures BG-concentration is given in mmol/l for the sake of dealing with values in a smaller range. In these examples m=5, l=6, PH=60 minutes; and each data segment was collected within a time interval of 110 minutes. All together, 49 data pieces with informative parts were selected from the Data Pool of considered subject. This pool consisted of CGM-measurements collected during 2 days at hospital conditions. Note that selected data pieces were sampled within time intervals, which may intersect each other. Selected pieces formed a new Data Pool $\{(t_j^{(\mu)}, y_j^{(\mu)})_{j=p}^{p+10}\}_{\mu=1}^{Q_{new}}$, $Q_{new}=49$.

It will be appreciated that other selection criteria for selecting informative data segments may be used.

Learning Algorithm in the Prediction

For given m-subsequent measurements $(t_j, y_j)_{j=p}^{m+p-1}$, a predictor based on statistical learning theory and regularization networks is constructed. Such a predictor depends on a reproducing kernel, K, and a regularization parameter, $\lambda$, which are not fixed a priori.

To construct a predictor, $f_K^\lambda$, for given $(t_j, y_j)_{j=p}^{m+p-1}$, one minimizes the following Tikhonov-type functional $$f_K^\lambda = \operatorname{argmin} \frac{1}{m} \sum_{i=p}^{m+p-1} (y_i - f(t_i))^2 + \lambda \|f\|_H^2$$

over a reproducing kernel Hilbert space $H=H_K$ generated by a reproducing kernel, K. The predictor $f_K^\lambda = f_K^\lambda(t)$ can be explicitly given in the form $$f_K^\lambda(t) = \sum_{i=p}^{m+p-1} c_i K(t, t_i),$$

where $C=(c_i)=(m\lambda I + M_K)^{-1} Y$, $Y=(y_i)$, $M_K=(K(t_i, t_j))$, and I is the unit matrix of the size m. This method is a special case of the Tikhonov regularization method. One can also use iterative Tikhonov regularization, which has a higher qualification than the standard Tikhonov regularization. In such case $f_K^\lambda$ has the same form as in equation (1), but $C=(c_i)=(m^2\lambda I + M_K^2)^{-1} M_K Y$.

To achieve a good performance, the regularization parameter $\lambda$ should be tuned properly. This can be done adaptively by means of the quasi-balancing principle (as described in De Vito et al.: "*Adaptive kernel methods using the balancing principle*", Found. Comput. Math. V. 10, pp. 445-479, 2010), which selects $\lambda$ from the set $\{\lambda = \lambda_i = \lambda_0 q^i, i=0, 1, \ldots, M, q>1\}$.

Using the quasi-balancing principle, let $\{f_K^{\lambda_i}\}$ be the predictors (1) constructed for some $H=H_K$ and $\lambda_i = \lambda_0 q^i$, $i=0, 1, \ldots, M$, $q>1$. The choice of the regularization parameter is given by $\lambda_+ = \min\{\lambda_{emp}, \lambda_{H_K}\}$, where $$\lambda_{emp} = \lambda_k,$$

$$k = \operatorname{argmin}\{\sigma_{emp}(v): v = 1, 2, \ldots, M\},$$

$$\sigma_{emp}(v) = \|f_K^{\lambda_v} - f_K^{\lambda_{v-1}}\|_{\{t_j\}_{j=p}^{m+p-1}},$$

$$\lambda_{H_K} = \lambda_h,$$

$$h = \operatorname{argmin}\{\sigma_{H_K}(v): v = 1, 2, \ldots, M\},$$

$$\sigma_{H_K}(v) = \|f_K^{\lambda_v} - f_K^{\lambda_{v-1}}\|_{H_K},$$

$$\|g\|_{\{t_j\}_{j=p}^{m+p-1}}^2 = \frac{1}{m} \sum_{j=p}^{m+p-1} |g(t_j)|^2,$$

and $$\|g\|_{H_K}^2 = \frac{1}{m} \sum_{i=p}^{m+p-1} \sum_{j=p}^{m+p-1} c_i c_j K(t_i, t_j),$$

for $$g(t) = \sum_{k=p}^{m+p-1} c_k K(t_k, t) \in H_K.$$

It is noted that the quasi-balancing principle is a heuristic rule that can be used in case of a small sample size m, and it does not require any a priori knowledge about the predictor.

From the above, if for given $(t_j, y_j)_{j=p}^{m+p-1}$ a kernel, K, and an initial parameter, $\lambda_0$, are specified, then the learning algorithm constructs the predictor $f_K^{\lambda_+}$ which will predict the values y of BG in time interval $t \in [t_{m+p}, t_{m+p+l-1}] = [t_{m+p}, t_{m+p} + PH]$.

In the present prediction algorithms a kernel will be chosen from a 3-parameter set $K = \{K(t,\tau) = (t\tau)^\alpha + \beta e^{-\gamma(t-\tau)^2}: (\alpha,\beta,\gamma) \in [10^{-3},1] \times [10^{-3},3] \times [10^{-6},10^{-3}]\}$. It will be appreciated that, in other embodiments, other forms of kernels may be chosen.

A supervising, or main, learning machine is constructed which will learn from given examples and suggest a choice of the kernel, K, and starting parameter, $\lambda_0$, for any given $(t_i, y_i)_{i=p}^{m+p-1}$. To construct such a main learning machine the new Data Pool containing only pieces with informative parts is transformed into a training set.

Construction of a Training Set

The training set for the main learning machine consists of pairs of input and output vectors:

The input vector contains information about BG value $(y_i^{(\mu)})_{i=p}^{m+p-1}$ for some time interval $[t_p^{(\mu)}, t_{m+p-1}^{(\mu)}]$.

The output vector consists of kernel parameters $(\alpha_p^{(\mu)}, \beta_p^{(\mu)}, \gamma_p^{(\mu)}) \leftrightarrow K_p^{(\mu)} \in K$, and parameter $\lambda_+ = \lambda_{+,p}^{(\mu)}$, which are associated to $(t_i^{(\mu)}, y_i^{(\mu)})_{i=p}^{m+p-1}$ such that $f_K^\lambda(t)$ given for this data by the formula (1) with $\lambda = \lambda_+ = \lambda_{+,p}^{(\mu)}$ and $K = K_p^{(\mu)}$ will accurately approximate $(y_i^{(\mu)})_{i=m+p}^{m+p+l-1}$ at $(t_i^{(\mu)})_{i=m+p}^{m+p+l-1}$. Note that $\lambda_{+,p}^{(\mu)}$ is determined through the quasi-balancing principle by the kernel parameters $(\alpha_p^{(\mu)}, \beta_p^{(\mu)}, \gamma_p^{(\mu)})$ and the informative part $(t_i^{(\mu)}, y_i^{(\mu)})_{i=p}^{m+p-1}$.

In order to construct such a training set, for each $(t_i^{(\mu)}, y_i^{(\mu)})_{i=p}^{m+p+l-1}$, $\mu = 1, 2, \ldots, Q_{new}$, from the Data Pool the following quantity is considered:

$$E(\alpha, \beta, \gamma; (t_i^{(\mu)}, y_i^{(\mu)})_{i=p}^{m+p+l-1}) = \sum_{i=m+p}^{m+p+l-1} |y_i^{(\mu)} - f_K^{\lambda_+}(t_i^{(\mu)})|_A, \quad (2)$$

where $(\alpha,\beta,\gamma) \leftrightarrow K \in K$, and $f_K^{\lambda_+}$ is defined by (1) for $t_i = t_i^{(\mu)}$, $y_i = y_i^{(\mu)}$, $i = p, p+1, \ldots, p+m-1$, and $\lambda = \lambda_+$ chosen in accordance with the quasi-balancing principle starting from, say $\lambda_0 = 10^{-5}$. Moreover, here $|y_i^{(\mu)} - f_K^{\lambda_+}(t_i^{(\mu)})|_A = A$ if $c < 70 (mg/dl) \wedge d \leq 180 (mg/dl) \wedge y_i^{(\mu)} - f_K^{\lambda_+}(t_i^{(\mu)}) < 0$, $|y_i^{(\mu)} - f_K^{\lambda_+}(t_i^{(\mu)})|_A = y_i^{(\mu)} - f_K^{\lambda_+}(t_i^{(\mu)})$ if $c < 70(mg/dl) \wedge d \leq 180(mg/dl) \wedge y_i^{(\mu)} - f_K^{\lambda_+}(t_i^{(\mu)}) \geq 0$, $|y_i^{(\mu)} - f_K^{\lambda_+}(t_i^{(\mu)})|_A = f_K^{\lambda_+}(t_i^{(\mu)}) - y_i^{(\mu)}$ if $c \geq 70(mg/dl) \wedge d > 180(mg/dl) \wedge f_K^{\lambda_+}(t_i^{(\mu)}) - t_i \geq 0$, $|y_i^{(\mu)} - f_K^{\lambda_+}(t_i^{(\mu)})|_A = A$ if $c \geq 70(mg/dl) \wedge d > 180(mg/dl) \wedge f_K^{\lambda_+}(t_i^{(\mu)}) - y_i^{(\mu)} < 0$, and $|y_i^{(\mu)} - f_K^{\lambda_+}(t_i^{(\mu)})|_A = |y_i^{(\mu)} - f_K^{\lambda_+}(t_i^{(\mu)})|$ otherwise, $c = \min_{m+p \leq i \leq m+p+l-1} y_i^{(\mu)}$, $d = \max_{m+p \leq i \leq m+p+l-1} y_i^{(\mu)}$, and A is a fixed large positive number. In the present experiments A=40 (mg/dl). The basic idea about the new measure $|y_i^{(\mu)} - f_K^{\lambda_+}(t_i^{(\mu)})|_A$ is that it penalises heavily if there is a delay or failure in the prediction of dangerous events (hypoglycaemia/hyperglycaemia).

Using the quantity (2) we construct the training set for the main learning machine by assigning each of data pieces $(t_i^{(\mu)}, y_i^{(\mu)})_{i=p}^{m+p+l-1}$ from the new Data Pool to parameter set $(\alpha_p^{(\mu)}, \beta_p^{(\mu)}, \gamma_p^{(\mu)}, \lambda_{+,p}^{(\mu)})$, where $\alpha = \alpha_p^{(\mu)}$, $\beta = \beta_p^{(\mu)}$, $\gamma = \gamma_p^{(\mu)}$ realize the minimum value of the quantity $E(\alpha, \beta, \gamma; (t_i^{(\mu)}, y_i^{(\mu)})_{i=p}^{m+p+l-1})$.

Note that for each data piece $(t_i^{(\mu)}, y_i^{(\mu)})_{i=p}^{m+p+l-1}$ the quantity (2) is really a function of only three variables, and it can be easily calculated for any values of the variables $\alpha$, $\beta$, $\gamma$ defining a kernel $K \in K$. Therefore, the parameters $(\alpha_p^{(\mu)}, \beta_p^{(\mu)}, \gamma_p^{(\mu)})$ realizing the minimum value of (2) can be found by standard methods of functional minimization. In particular, one may use the minimization by random search technique (as described in Solis, Wets: "Minimization by random search techniques", Mathematics of Operation Research, V. 6, pp. 19-30, 1981). For example, if the random search is generated by Gaussian random vectors with diagonal covariance matrix that has diagonal entries (0.5, 1.5, $5 \times 10^{-4}$), and the limit on the maximal number of search steps is set to $10^4$, then the application of this technique to the minimization of the function(2) for two data pieces $(t_i^{(\mu)}, y_i^{(\mu)})_{i=p}^{m+p+l-1}$, m=5, l=6, shown in FIGS. 1a, 1b, gives respectively the following values of the parameters $\alpha_p^{(\mu)} = 0.0963, 0.8794$, $\beta_p^{(\mu)} = 2.83, 2.955$, $\gamma_p^{(\mu)} = 6.4 \times 10^{-5}, 2.38 \times 10^{-4}$ $\lambda_{+,p}^{(\mu)} = 10^{-4}, 1.27 \times 10^{-4}$. The graphs of the corresponding functions $f_K^{\lambda_+}(t)$ with $K \leftrightarrow (\alpha_p^{(\mu)}, \beta_p^{(\mu)}, \gamma_p^{(\mu)})$, $\lambda_+ = \lambda_{+,p}^{(\mu)}$, $t \in [t_p^{(\mu)}, t_{m+p+l-1}^{(\mu)}]$, are displayed by solid lines in FIGS. 1a and 1b. In the considered context they are interpreted as the predictions for $t \in [t_{m+p}^{(\mu)}, t_{m+p}^{(\mu)} + PH]$, PH=60 minutes, from the data $(t_i^{(\mu)}, y_i^{(\mu)})_{i=p}^{m+p-1}$.

As mentioned earlier, the essential information about $\{(t_i^{(\mu)}, y_i^{(\mu)})\}_{i=p}^{m+p-1}$ is captured in $(a_p^{(\mu)}, b_p^{(\mu)})$, where $a_p^{(\mu)} t + b_p^{(\mu)}$ is a linear fit to $\{(t_i^{(\mu)}, y_i^{(\mu)})\}_{i=p}^{m+p-1}$. To reduce the dimensionality of the problem, the training set is collected as $\{((a_p^{(\mu)}, b_p^{(\mu)}), (\alpha_p^{(\mu)}, \beta_p^{(\mu)}, \gamma_p^{(\mu)}, \lambda_{+,p}^{(\mu)}))\}$ for each $\{(t_i^{(\mu)}, y_i^{(\mu)})\}_{i=p}^{m+p+l-1}$ from the new Data Pool. It is noted that $(a_p^{(\mu)}, b_p^{(\mu)})$ is the input, while $(\alpha_p^{(\mu)}, \beta_p^{(\mu)}, \gamma_p^{(\mu)}, \lambda_{+,p}^{(\mu)})$ is the output for the training.

Construction of the Main Learning Machine

Figure 2:
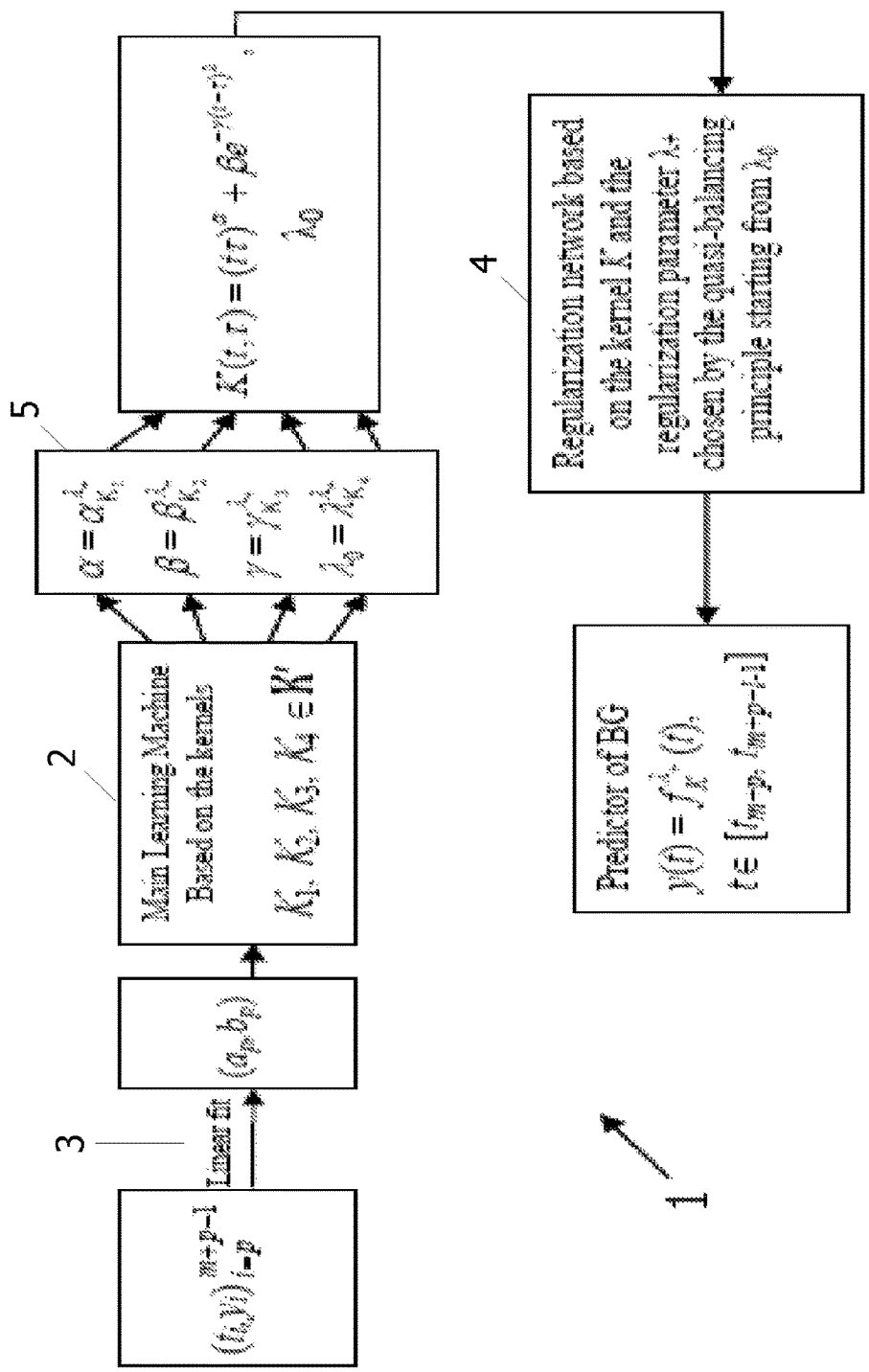
FIG. 2 shows a schematic representation of a particular realisation of the prediction algorithm according to an embodiment of the invention, based on a regularization network with adaptively chosen kernel and regularization parameter.

FIG. 2 shows the scheme of an exemplary embodiment of a prediction process 1 based on a regularization network with adaptively chosen kernel and regularization parameter. The values of the kernel parameters $(\alpha, \beta, \gamma) \leftrightarrow K \in K$ and the starting parameter $\lambda_0$ in the quasi-balancing principle are suggested by the main learning machine 2 on the basis of learning from training sets formed for each of parameters as follows:

input: $(a_p^{(\mu)}, b_p^{(\mu)}) \rightarrow$ output: $\alpha_p^{(\mu)}$
input: $(a_p^{(\mu)}, b_p^{(\mu)}) \rightarrow$ output: $\beta_p^{(\mu)}$
input: $(a_p^{(\mu)}, b_p^{(\mu)}) \rightarrow$ output: $\gamma_p^{(\mu)}$
input: $(a_p^{(\mu)}, b_p^{(\mu)}) \rightarrow$ output: $\lambda_{+,p}^{(\mu)}$ The main learning machine may be trained off-line prior to the actual prediction process. Then for any input $u = (a_p, b_b)$ containing the coefficients of a linear fit 3 to given subsequent measurements $(t_i, y_i)_{i=p}^{m+p-1}$ in question the values of the parameters $\alpha, \beta, \gamma, \lambda_0$ are defined by predictors $\alpha = \alpha_{K_1}^\lambda(u)$, $\beta = \beta_{K_2}^\lambda(u)$, $\gamma = \gamma_{K_3}^\lambda(u)$, $\lambda_0 = \lambda_{K_4}^\lambda(u)$, which are constructed with the use of iterative Tikhonov regularization in reproducing kernel Hilbert spaces $H_{K_i}$, $i = 1, 2, 3, 4$, generated by the kernels $K_i$, from the following collection:

$$K' = \left\{ K(u,v) = \frac{1}{Q_{new}} \sum_{p=1}^{Q_{new}} \varphi_\xi(|u - u_p|_r)\varphi_\xi(|v - u_p|_r), u, v \in R^2, \right. \quad (3)$$

$$\left. \xi = (\xi_0, \xi_1, \ldots, \xi_4) \in \{0, 1\} \times [0, 4] \times [0, 15] \times [0, 4] \times [0, 4] \right\}$$

where $Q_{new}$ is the number of data pieces in the new Data Pool, $u_p = (a_p^{(\mu)}, b_p^{(\mu)})$, $$\varphi_\xi(\tau) = \xi_0 \tau^{\xi_1} + \xi_2 e^{-\xi_3 \tau^{\xi_4}}$$

and $|\cdot|_r$ denotes the natural weighted distance in $R^2$ which is defined by $|u|_r = (r_1 u_1^2 + r_2 u_2^2)^{1/2}$. It is clear that any kernel $K \in K'$ is completely defined by the values of $\xi_0, \ldots, \xi_4$. The values of the weighting coefficients $r_1$ and $r_2$ may be selected a priori. In the present embodiment they are selected to be either 0 or 1; however, other choices are possible as well. Yet alternatively, the values of $r_1$ and $r_2$ may also be determined by the data in a similar fashion as the values of $\xi_0, \ldots, \xi_4$.

It will be appreciated that the predictors for $\alpha$, $\beta$, $\gamma$, and $\lambda_0$ may be determined by kernels from different collections of kernels K'. For example, in another embodiment, the kernels for the main learning machine may be chosen from the following collection $K' = \{K(u,v) = -\|u-v\|^{\alpha_1} + \alpha_2 e^{-\alpha_3\|u-v\|^{\alpha_4}}$, $u, v \in R^2$, $\alpha_1, \alpha_4 \in [0,2]$, $\alpha_2, 60_3 \in [0,15]\}$. In this case, any kernel $K \in K'$ is completely defined by the values of $\alpha_1, \alpha_3, \alpha_4$ which may be determined in a similar fashion as will now be described for the values of $\xi_0, \ldots, \xi_4$.

Having a training set with an essential amount of possible events for a subject, the choice of the kernel, say $K_1$, for the main machine can be done by splitting the corresponding training set into two parts in the following way:
1) Split the training set $z' = \{((a_p^{(\mu)}, b_p^{(\mu)}), \alpha_p^{(\mu)})\} = \{(u_p, h_p)\}$ (where $u_p = (a_p^{(\mu)}, b_p^{(\mu)})$, $h_p = \alpha_p^{(\mu)}$ for some p, $\mu$) into two subsets $z_t'$ and $z_c'$ such that $z' = z_t' \cup z_c'$, and $z_c'$ contains, for example, the pairs $(u_p, h_p)$ with the first two largest and the first two smallest $h_p$.
2) Take, for example, $\xi_0 = 1$ and consider the quantity $$E_1(\xi_1, \xi_2, \xi_3, \xi_4; z') = \frac{1}{|z'|} \sum_{(u_p, h_p) \in z_c'} |h_p - \alpha_K^{\lambda_+}(u_p)|^2, \quad (4)$$

where $|z|$ means the number of elements in some set z, $(\xi_1, \xi_2, \xi_3, \xi_4) \leftrightarrow K \in K'$, and $\alpha_K^\lambda(u)$ is defined by means of the iterative Tikhonov regularization in the form $$\alpha_K^\lambda(u) = \sum_{u_p : (u_p, h_p) \in z_t'} c_p K(u, u_p)$$

with $(c_p) = (|z_t'|^2 \lambda I + M_K^2)^{-1} M_K Y$. Here I is the unit matrix of the size $|z_t'|$, and $M_K$, Y are the matrix and the vector of the size $|z_t'|$, which are formed by numbers $K(u_p, u_q)$, $h_p$ with p,q such that $(u_p, h_p), (u_q, h_q) \in z_t'$. Moreover, the regularization parameter $\lambda = \lambda_+$ is chosen, in the same way as before, by means of the quasi-balancing principle, where $$\sigma_{emp}(\nu) = \|\alpha_K^{\lambda_\nu} - \alpha_K^{\lambda_{\nu-1}}\|_{\{u_p : (u_p, h_p) \in z_t'\}}, \sigma_{H_K}(\nu) = \|\alpha_K^{\lambda_\nu} - \alpha_K^{\lambda_{\nu-1}}\|_{H_K}.$$

Figure 3:
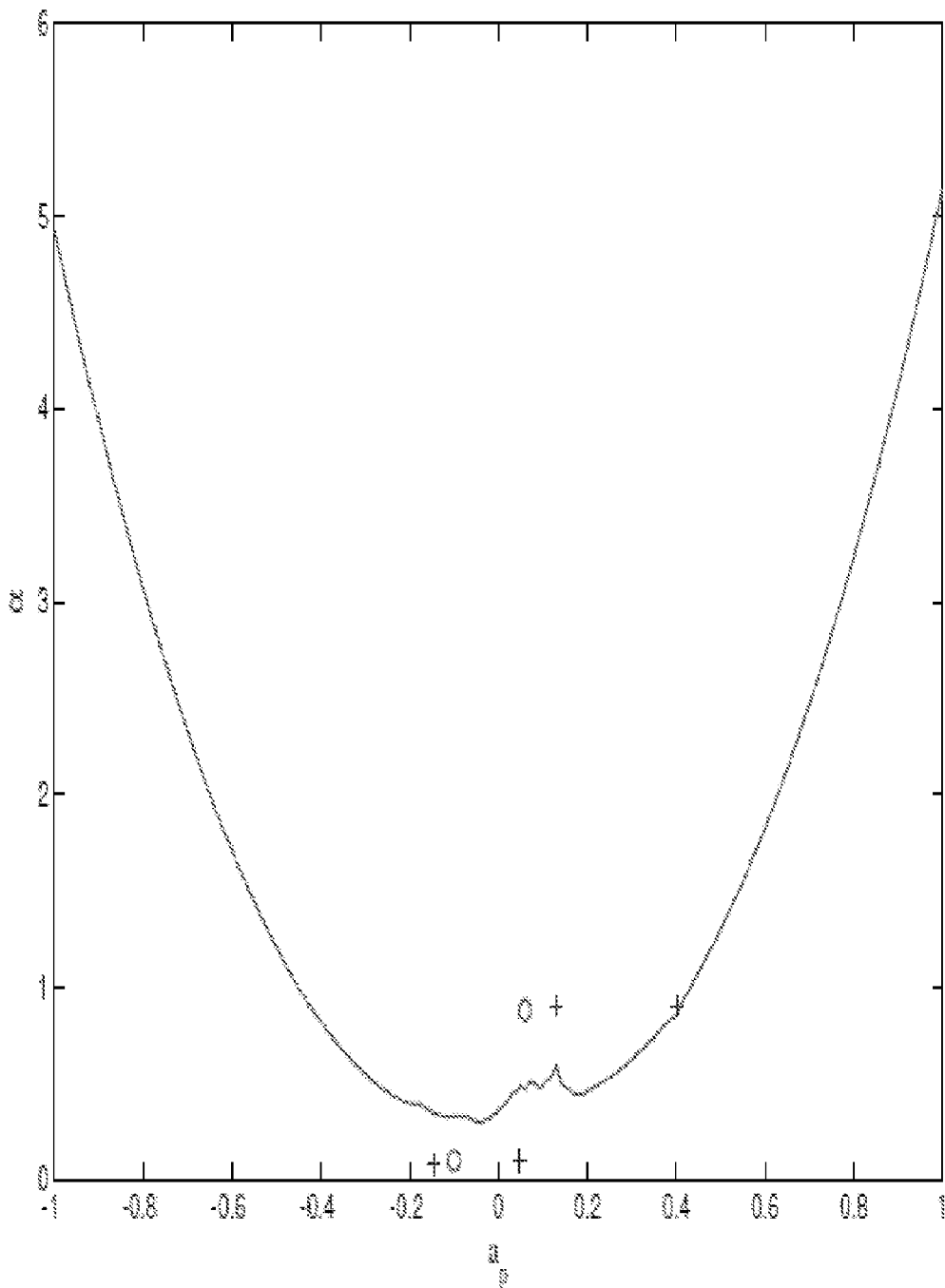
FIG. 3 shows the graph of one of functions specifying the parameters for adaptive choice of kernels in an exemplary embodiment.

It is clear that for fixed training set z' the quantity (4) is a function of variables $\xi_1, \xi_2, \xi_3, \xi_4$, and its point of minimum $(\xi_1^{(1)}, \xi_2^{(1)}, \xi_3^{(1)}, \xi_4^{(1)})$ can be found by standard methods of functional minimization. For example, for the training set z' constructed from the Data Pool of the subject (Patient ID: Subject4) and for $r_1 = 1$, $r_2 = 0$ (i.e., for the case when only the first component $a_p$ of the vector $u = (a_p, b_p)$ is taken into account) the use of the minimization by random search mentioned above gives the values $\xi_1^{(1)} = 2.2$, $\xi_2^{(1)} = 0.3$, $\xi_3^{(1)} = 1.95$, $\xi_4^{(1)} = 0.16$. The graph of the corresponding function $\alpha_{K_1}^{\lambda_+}(u) = \alpha_{K_1}^{\lambda_+}(a_p)$ with $\lambda_+ = 1.2081 \times 10^{-4}$ and $(\xi_1^{(1)}, \xi_2^{(1)}, \xi_3^{(1)}, \xi_4^{(1)}) \leftrightarrow K_1 \in K'$, is displayed in FIG. 3. In this figure the points marked by (o) correspond to the inputs $\alpha_p^{(\mu)}$ from the training set z' found for data pieces displayed in FIGS. 1a and 1b. The points marked by (+) correspond to the inputs from the part $z_c' \subset z'$ used in the definition of the quantity (4).

The determined point of minimum $(\xi_1^{(1)}, \xi_2^{(1)}, \xi_3^{(1)}, \xi_4^{(1)})$ thus specifies the kernel $K_1$, and the kernel $K_1$ together with the subset $z_t'$ and the above schedule for specifying the regularisation parameter $\lambda = \lambda_+$ are sufficient for calculating $\alpha_{K_1}^{\lambda_+}$ as a function of an input $(a_p, b_p)$. The predictor $\alpha_{K_1}^{\lambda_+}$ will thus specify the value of $\alpha$ to choose a kernel $K \in K$. In a similar manner, the other parameter predictors $\beta_{K_2}^{\lambda_+}$, $\gamma_{K_3}^{\lambda_+}$, $\lambda_{K_4}^{\lambda_+}$, $K_2$, $K_3$, $K_4 \in K'$ are constructed and the predictors $\alpha_{K_1}^{\lambda_+}$, $\beta_{K_2}^{\lambda_+}$, $\gamma_{K_3}^{\lambda_+}$, $\lambda_{K_4}^{\lambda_+}$ are the results of the training process to be used during the subsequent prediction process.

During the subsequent prediction process the predictors $\beta_{K_1}^{\lambda_+}$, $\beta_{K_2}^{\lambda_+}$, $\gamma_{K_3}^{\lambda_+}$, $\lambda_{K_4}^{\lambda_+}$ are used in the specification of a kernel $K \in K$ for use in eqn. (1). As described above, the prediction process 1 comprises a main learning machine 2 or prediction setting stage, and a prediction execution stage 4. Thus, in the considered exemplary embodiment of the prediction process, for a given input $(a_p, b_p)$ the main learning machine uses the trained non-linear relationships $\alpha_{K_1}^{\lambda_+}$, $\beta_{K_2}^{\lambda_+}$, $\gamma_{K_3}^{\lambda_+}$, $\lambda_{K_4}^{\lambda_+}$ to determine the parameters 5 of the kernel $K(t, \tau) = (t\tau)^\alpha + \beta e^{-\gamma(t-\tau)^2} \in K$ and the initial regularization parameter $\lambda_0$, where the parameters are given as $\alpha = \alpha_{K_1}^{\lambda_+}(u)$, $\beta = \beta_{K_2}^{\lambda_+}(u)$, $\gamma = \gamma_{K_3}^{\lambda_+}(u)$, $\lambda_0 = \lambda_{K_4}^{\lambda_+}(u)$, and $u = (a_p, b_p)$. With the suggested kernel K and $\lambda_0$ for $(t_i, y_i)_{i=p}^{m+p-1}$, the predictor $f_K^{\lambda_+}$ is constructed by the prediction execution stage 4 using the learning algorithm (1), which will give a prediction in the time interval $[t_{m+p}, t_{m+p} + PH]$.

In an exemplary embodiment of a BG-prediction process the main learning machine 2 is completely defined by the functions $\alpha_{K_1}^{\lambda_+}(u)$, $\beta_{K_2}^{\lambda_+}(u)$, $\gamma_{K_3}^{\lambda_+}(u)$, $\lambda_{K_4}^{\lambda_+}(u)$, which are constructed off-line with the use of Data Pool of a particular patient. Once these functions are specified, the BG-prediction process is ready to operate on-line for this patient. At the same time, the performance tests reported below show that the main learning machine defined for a particular individual can be then successfully used for others without any readjustments. The functions $\alpha_{K_1}^{\lambda_+}(u)$, $\beta_{K_2}^{\lambda_+}(u)$, $\gamma_{K_3}^{\lambda_+}(u)$, $\lambda_{K_4}^{\lambda_+}(u)$ may be computed by the same device that performs the on-line prediction process. For example, a computer program executed by a prediction device may be executed in a training mode to compute the functions $\alpha_{K_1}^{\lambda_+}(u)$, $\beta_{K_2}^{\lambda_+}(u)$, $\gamma_{K_3}^{\lambda_+}(u)$, $\lambda_{K_4}^{\lambda_+}(u)$. Alternatively, the functions $\alpha_{K_1}^{\lambda_+}(u)$, $\beta_{K_2}^{\lambda_+}(u)$, $\gamma_{K_3}^{\lambda_+}(u)$, $\lambda_{K_4}^{\lambda_+}(u)$ may be computed by a data processing system different from the prediction device. Once computed, the functions $\alpha_{K_1}^{\lambda_+}(u)$, $\beta_{K_2}^{\lambda_+}(u)$, $\gamma_{K_3}^{\lambda_+}(u)$, $\lambda_{K_4}^{\lambda_+}(u)$ may be installed on the prediction device in any suitable form, e.g. by storing the parameters specifying the kernels $K_i$, $i = 1, \ldots, 4$, and the corresponding subset(s) $z_t'$ of compressed data segments. In some embodiments, the above parameters may be transmitted to the prediction device using any suitable communications channel, thus allowing repeated updates of the main learning machine, e.g. based on updated data pools.

Performance Tests

Figures 4A, 4B:
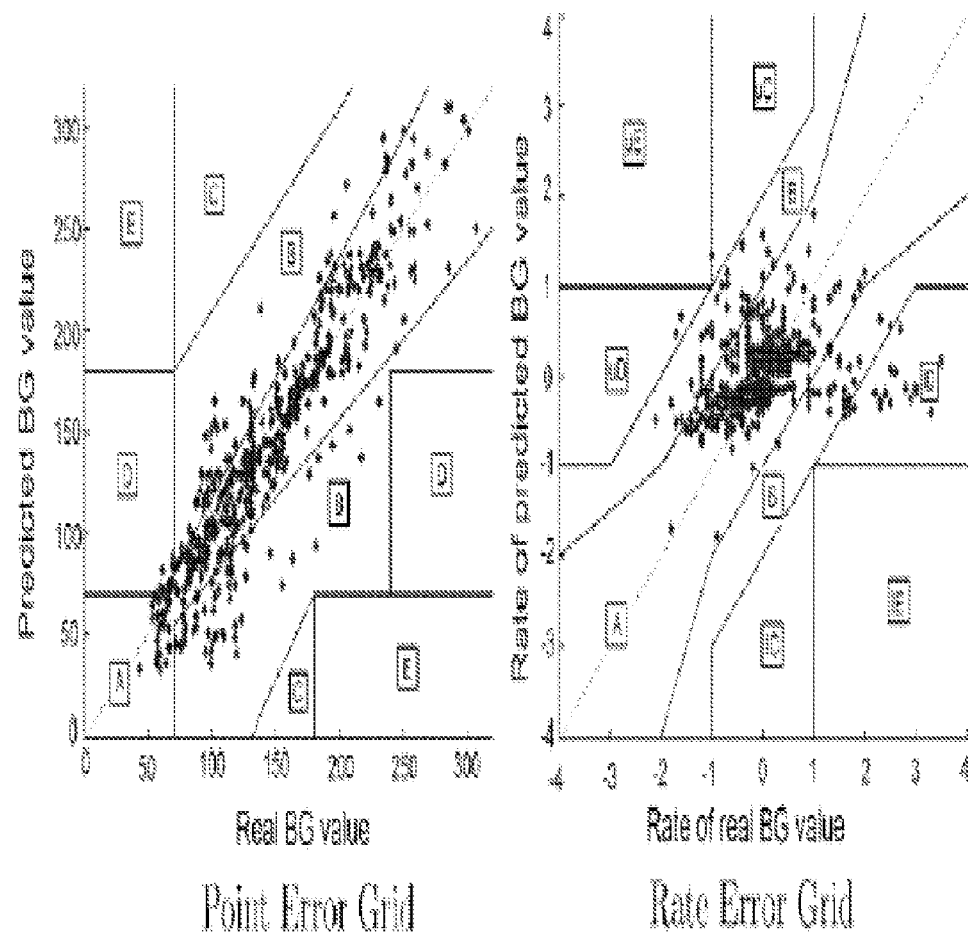
FIGS. 4a and 4b show a point error grid, respectively a rate error grid exemplifying an assessment for predictions made with a prediction horizon of 30 minutes.

The performance assessment of an example of a predictor constructed by the above-described method has been made with the use of three different assessment metrics known from the literature. One of them is the classical Point Error Grid Analysis (EGA) by Clarke (described in Clarke et al.: "*Evaluating clinical accuracy of systems for self-monitoring of blood glucose*", Diabetes Care, 10(5):622-628, 1987). Another one is the Continuous Glucose Error Grid Analysis (CG-EGA) (described in Kovatchev et al.: "*Evaluating the* accuracy of continuous glucose-monitoring Sensors: Continuous glucose error grid analysis illustrated by TheraSense Freestyle Navigator data", Diabetes Care, 27(8): 1922-1928, 2004, and in Clarke: "*The original Clarke error grid analysis (EGA)*", Diabetes Tech. & Therapeutics, 7(5): 776-779, 2005), which can be used for an assessment of the clinical accuracy of both continuous glucose monitors (Kovatchev et al.: "*Comparison of the numerical and clinical accuracy of four continuous glucose monitors*", Diabetes Care, 31:1160-1164, 2008) and BG prediction engines (Zanderigo et al.: "*Glucose prediction algorithms from continuous monitoring data: Assessment of accuracy via Continuous Glucose Error-Grid Analysis*", Journal of Diabetes Sci. and Tech., 1(5):645-651, 2007). The third used assessment metric is the Prediction Error Grid Analysis (PRED-EGA) (described in Sivananthan et al.: "*Assessment of Blood Glucose Predictors: The Prediction Error Grid Analysis*", Diabetes Tech. & Therapeutics, 13 (8): 787-796, 2011) that has been designed especially for BG prediction assessment. The performance tests have been made with the use of clinical data from two trials executed within EU-project "DIAdvisor" at CHU-Montpellier, France, and IKEM—Prague, Czech Republic. In the first trial, each clinical record of a diabetes patient contains nearly 10 days of CGM-data collected with the use of Abbott's Freestyle Navigator® Continuous Glucose Monitoring system having a sampling frequency of 10 minutes. For each subject, two days record is used to train and test the main learning machine (in the experiments four hours were used for testing). Then assessment has been done for the remaining nearly eight days that corresponds to the recommended use period for a CGM sensor. It is stressed that no recalibration/readjustment of the prediction engines has been made during this assessment period. Examples of CG-EGA assessment for predictions made with time horizon 30 minutes are shown in FIGS. 4a and 4b (Patient ID: Subject4).

For the considered subject the parameters of the kernels (3) in the Main Learning Machine have been determined in accordance with the procedure described in the above as follows:

$K_1$:$\xi$=(1, 2.2, 0.3, 1.95, 0.16), r=(1, 0), $Q_{new}$=49,
$K_2$: $\xi$=(1, 0.16, 0.01, 2, 3), r=(1, 0), $Q_{new}$=49,
$K_3$: $\xi$=(1, 0, 1, 0.001, 0.003), r=(1, 0), $Q_{new}$=49,
$K_4$: $\xi$=(1, 0.2, 0.02, 0.1, 0.2), r=(1, 1), $Q_{new}$=49.

The CG-EGA calculates combined accuracy in three clinically relevant regions, hypoglycaemia (<70 mg/dl), euglycaemia (70-180 mg/dl), and hyperglycaemia (>180 mg/dl). In short, it provides three estimates of the predictor performance. FIG. 5 presents predictor assessment using this format. For comparison, in FIG. 6 one can see the assessment of the accuracy for the Abbott Navigator sensors presented in Clarke: "*The original Clarke error grid analysis (EGA)*", Diabetes Tech. & Therapeutics, 7(5):776-779, 2005. Thus, from a view point of CG-EGA the performance of the proposed predictor with reference to CGM-data really mimics the performance of some continuous glucose monitoring systems, such as Abbott's Freestyle Navigator® Continuous Glucose Monitoring System, with reference to blood glucose. Such comparison of predictor and sensor performances can be considered as a benchmark, since a predictor is trying to predict what will be shown by a sensor, and from this view point can be treated as a "surrogate sensor".

FIG. 7 shows the results of CG-EGA for 11 subjects. The predictions have been made for 30 minutes ahead.

At the same time, data collected at CHU-Montpellier allows a prediction comparison with reference to blood glucose for both the present predictor and the Freestyle Navigator® Continuous Glucose Monitoring System used at CHU. In this comparison EGA is used because of non-uniform and scarce reference glucose sampling. The results are presented in FIG. 8. They show that the reliability of the present prediction engine is level with the sensor reliability: in all cases the predictor and the sensor have almost the same percentage of clinically acceptable (A+B zones) and erroneous reading (D zone).

The performance of the present predictor has also been compared with that of the predictor developed by Reifman et al. ("*Predictive Monitoring for Improved Management of Glucose Levels*", Journal of Diabetes Sci. and Tech., 1(4): 478-486, 2007), using standard Point Error Grid Analysis because this performance measure was used by Reifman et al. Comparison was made in cases of the prediction for half an hour (FIG. 9), and for one hour (FIG. 10). In this connection it is stressed that Reifman et al. sampled data each minute, while in the present experiments the data sampling rate was 10 minutes.

Another series of the performance tests were made with the use of clinical data from the second trial executed at IKEM—Prague, where the objective was to check whether a predictor based on the present approach can provide accurate BG predictions during provocation of hypo and hyperglycaemia. In that trial 6 patients (Patient ID: Subject12, . . . , Subject17) were asked to make one provoked hyperglycaemia and one provoked hypoglycaemia by applying, respectively, lower dose of insulin (minus 30% of usual dose) and higher dose of insulin (plus 30% of usual dose) before their two lunches.

A special blood sampling schedule was used to measure real blood glucose concentration by YSI analyzer during the provocation periods. Blood samples were collected every five to ten minutes during at least 2.5 hours from the beginning of each test. Seven® Plus CGM devices were used in the study for providing the prediction inputs. Such CGM device estimates BG concentration every 5 minutes, and the estimates produced in the recent 25 minutes are used for predicting the future BG profile. It is important to note that the tested glucose prediction system was not specially readjusted for performing during provocation of hypo and hyperglycaemia. Moreover, the tested system was not readjusted for receiving prediction inputs from Seven® Plus CGM, which has a different sampling frequency than Abbott's Freestyle Navigator® used previously. Therefore, the tested systems reports the prediction profiles for time moments/horizons PH=0, 10, 20, 30, . . . , minutes, determined by the Freestyle Navigator® sampling frequency $\Delta t$=10 minutes, while new prediction profiles are produced every 5 minutes, since Seven® Plus provides prediction inputs with this frequency. But what is probably even more important is that the tested system was not readjusted to any of the patients participating in the trial. More precisely, the kernels (3) in Main Learning Machine of the tested prediction system were determined in accordance with the procedure described in the above as follows:

$K_1$:$\xi$=(1, 1.6, 5, 0.001, 0.016), r=(1, 0), $Q_{new}$=24,
$K_2$: $\xi$=(1, 1.2, 0.001, 3, 0.01), r=(1, 0), $Q_{new}$=24,
$K_3$: $\xi$=(1, 0, 1, 0.001, 0.003), r=(1, 0), $Q_{new}$=24,
$K_4$: $\xi$=(1, 0.2, 0.02, 0.1, 0.2), r=(1, 1), $Q_{new}$=24.

and for this determination the data of another patient (Patient ID: Subject2) were used. Nevertheless, the tested prediction system performed quite well, as it can be seen in FIGS. 11, 12 and 13 displaying the assessment results produced by the PRED-EGA with reference to YSI blood glucose values for predictions with the horizons PH=0, 10, 20 (minutes) respectively. Note that the PRED-EGA used here is proven to be a very rigorous metric for the prediction assessment. It uses the same format as the CG-EGA, but in contrast to the latter, the PRED-EGA takes into account that predictors provide a BG estimation ahead of time, and it paves a new way to estimating the rates of glucose changes.

The PRED-EGA with reference to YSI blood glucose estimations can be also used to assess a CGM sensor, which in such a context could be viewed as an oracle knowing the future prediction input, or as a predictor with the horizon PH=0 (minutes). The results of such an assessment are shown in FIG. 14.

The comparison of the FIGS. 11-14 shows that during provocation of hypo and hyperglycaemia the predictions provided by the tested system for PH=0, 10 (minutes) are in average clinically more accurate than the corresponding BG estimations given by employed CGM device. For PH=20 minutes the accuracy of the tested system is at the level of the CGM accuracy, except for one patient (Patient ID: Subject15). The effect that for some horizons the tested prediction system can outperform the CGM device providing prediction inputs may be explained by the fact that the system takes into account a history of previous measurements and a training in the behaviour of CGM to be predicted.

Thus, the performance tests highlight such interesting advantages of the present approach as a portability from individual to individual, as well as from sensor to sensor, without readjustment, the possibility to use data with essential gaps in measurements, and the ability to perform at the level of the clinical accuracy achieved by approved CGM systems.

Special Event Training

For prediction after special events, such as meals, the performance of the proposed prediction can be improved. To do this the regularization networks generated by new kernels $K_i \in K'$, $i=1, \ldots, 4$, are incorporated into the main machine. These new networks are trained in the same way as described in the above, but the data for such training are collected after corresponding special events, say after breakfasts. The new part of the main machine is active only when a prediction after a special event is required. This idea is illustrated using CGM-data of Subject1 and Subject2 collected after breakfasts on two days at hospital and one day at home. Data from the first day was used for training new networks for the main machine. For Subject1, for example, the following kernels (parameters) (3) were found:

$K_1$: $\xi=(0, 0, 1, 1.5, 2)$, $r=(1, 0)$, $Q_{new}=1$,
$K_2$: $\xi=(0, 0, 1, 0.1, 2)$, $r=(1, 0)$, $Q_{new}=1$,
$K_3$: $\xi=(0, 0, 1, 2, 1.5)$, $r=(1, 0)$, $Q_{new}=1$,
$K_4$: $\xi=(1, 0.0001, 15, 2, 1)$, $r=(1, 1)$, $Q_{new}=1$.

Figure 15A:
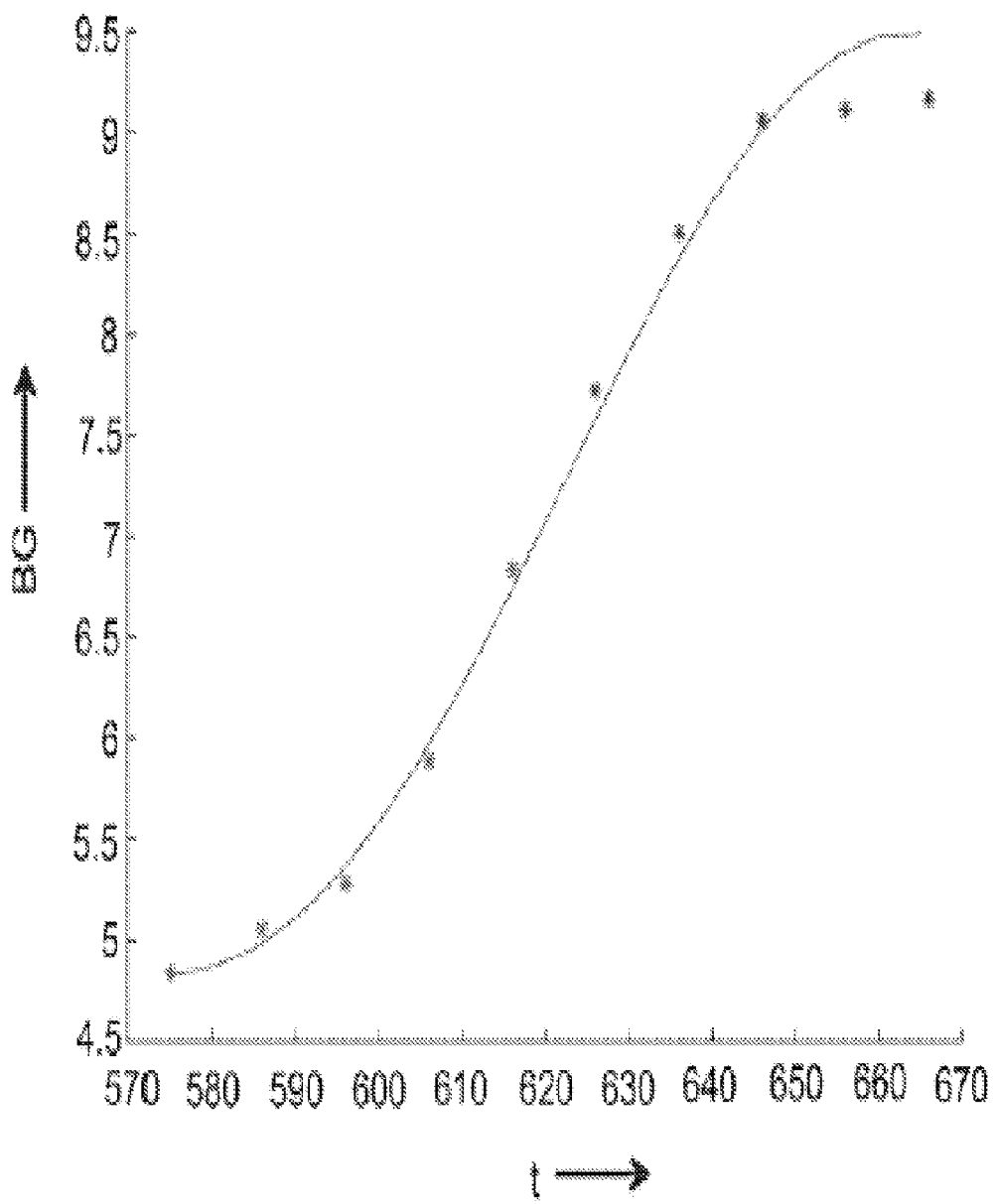
FIGS. 15a-15b and 16a-16b are graphs illustrating the effect of a special event training incorporated in a predictor according to an embodiment of the invention.
Figure 15B:
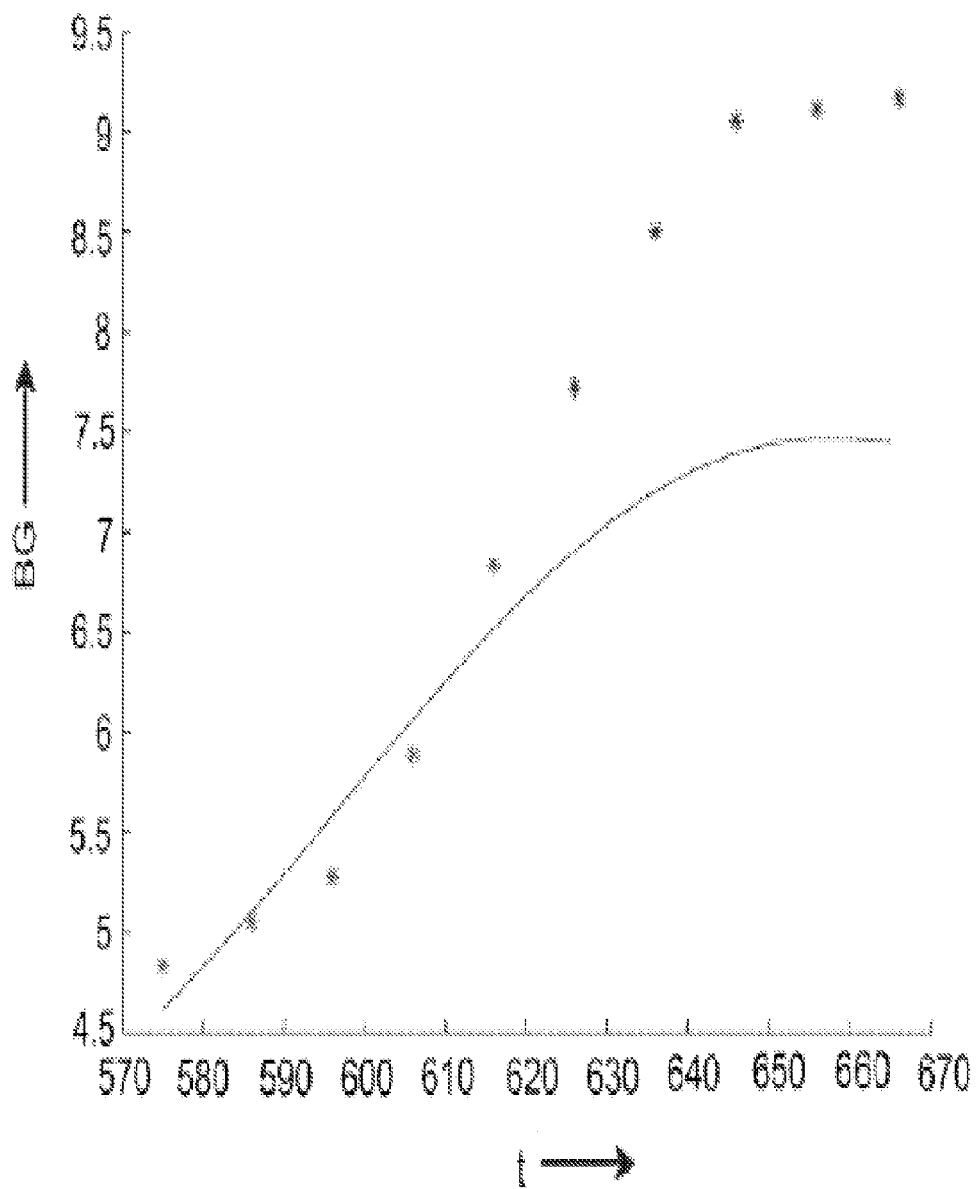

The other days were used for testing the performance of the new part of the main machine. A typical predicted BG profile together with CGM-data used for reference can be seen in FIG. 15a. Now the prediction horizon is PH=50 minutes. FIG. 15b shows the predicted profile produced by a plain predictor, which does not take special events into account. The improvement when incorporating special event training is obvious.

The design of the predictor based on adaptive regularization networks allows the use of strip measurements (e.g. HemoCue) in parallel with CGM-data. For example, if in the time interval where CGM-measurements are collected for making a prediction some HemoCue measurements are available, then they can be easily used instead of CGM-measurements made at corresponding moments of time; and no changes in the prediction algorithm are necessary for this.

Figure 16A:
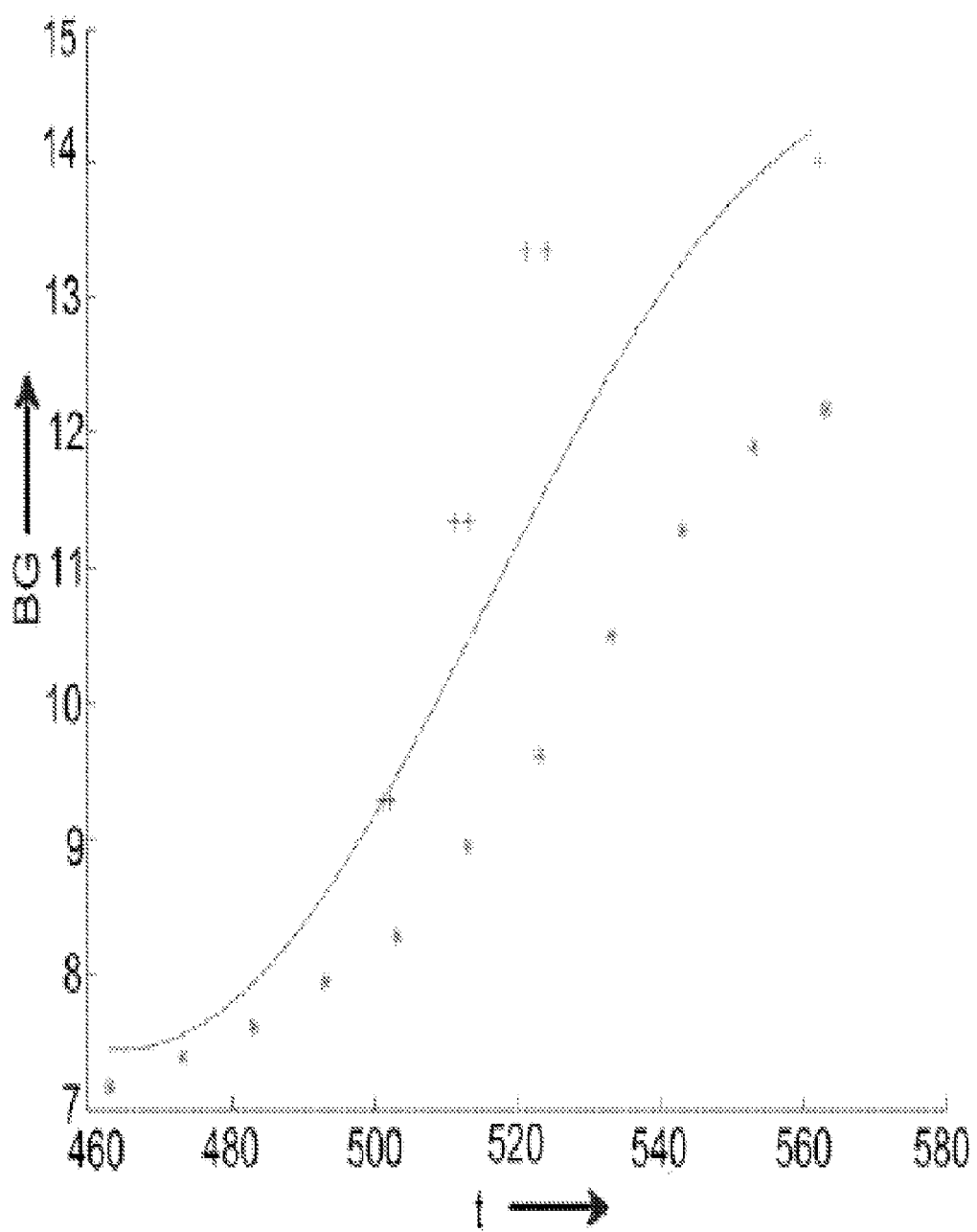
Figure 16B:
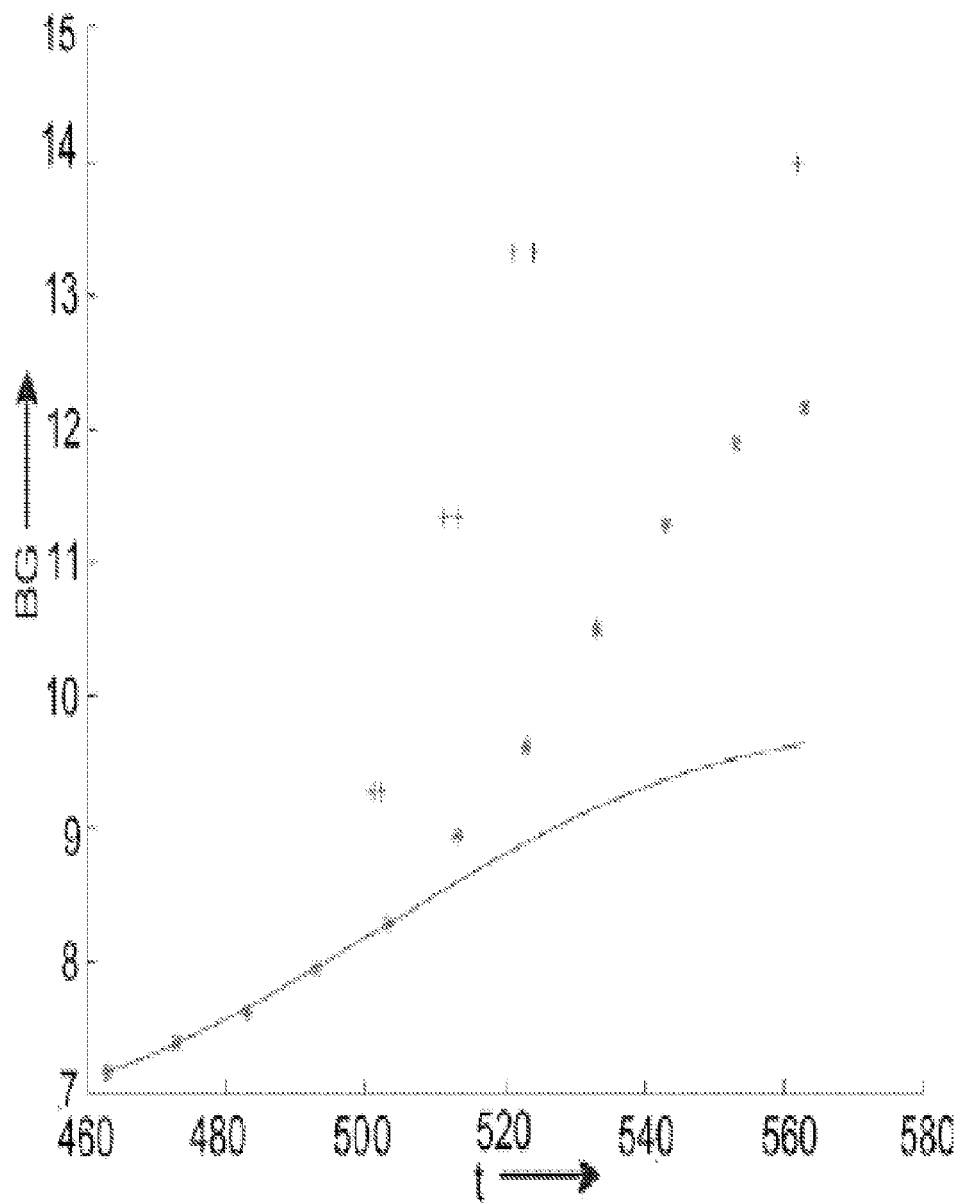

Usually the use of HemoCue measurements improves the prediction performance. A typical example is shown in the FIG. 16, where HemoCue measurements of Subject2 are labelled by (+), and CGM-data are marked by (*). In FIG. 16(b) the first five CGM-measurements are used for a prediction with 60 minutes prediction horizon, while in the FIG. 16(a) the last of them is substituted for an available HemoCue measurement. Again, an improvement is obvious.

FIG. 17 presents CG-EGA results for considered special event predictions. It turns out that the data for this experiment have been collected on the background of similar insulin dynamics. In the general case the information about current dynamics should be presented in the prediction input.

Extension of the Predictor

The design of the adaptive regularization networks predictor can be naturally extended to prediction from other types of inputs. Assume that at the moment of prediction $t=t_{m+p-1}$ in addition to the past glucose measurements $\{y_i\}_{i=p}^{m+p-1}$ made at the time moments $\{t_i\}_{i=p}^{m+p-1}$ information such as the amount of the insulin injection, $W_{1,p}$ made during a fixed period in the past, current basal level, $W_{2,p}$, intake of the latest/next meal, $W_{3,p}$, and so on, $W_{4,p}, \ldots, W_{s,p}$, is provided. If such information is also contained in the Data Pool then supervising learning machines can be constructed in the same spirit as in the above by considering the training set as input: $(a_p^{(\mu)}, b_p^{(\mu)}, W_{1,p}^{(\mu)}, \ldots, W_{s,p}^{(\mu)}) \rightarrow$ output:
$(\alpha_p^{(\mu)}, \beta_p^{(\mu)}, \gamma_p^{(\mu)}, \lambda_{+,p}^{(\mu)})$, where $W_{1,p}^{(\mu)}, \ldots, W_{s,p}^{(\mu)}$ are the values of the above mentioned information items given at the moment $t_{m+p-1}^{(\mu)}$, and $(\alpha_p^{(\mu)}, \beta_p^{(\mu)}, \gamma_p^{(\mu)}, \lambda_{+,p}^{(\mu)})$ is a vector of kernel and regularization parameters chosen as mentioned above.

Keeping in mind the increase of the input dimension the kernels for the main learning machine should now have the form of functions $K(u, v; W_1, \omega_1; W_2, \omega_2; \ldots; W_s, \omega_s)$ of $2s+2$ variables. If at the moment of prediction $t=t_{m+p-1}$ the value of some $W_{j,p}$ is not provided, then $W_{j,p}=0$. In that case the kernels of the main learning machine are automatically reduced to functions of a smaller number of variables $K(u,v;W_1,\omega_1;W_2,\omega_2;\ldots;W_{j-1},\omega_{j-1};W_{j+1},$
$\omega_{j+1};\ldots;W_s,\omega_s).$ In particular, one can choose the kernels for the main learning machine from the set $$K' = \Bigg\{ K(u,v; W_1, \omega_1; \ldots; W_s, \omega_s) =$$

$$\frac{1}{Q_{new}} \sum_{p=1}^{Q_{new}} \varphi_\xi(|u - u_p|_r, |W_1 - W_{1,p}|, \ldots, |W_s - W_{s,p}|)$$

$$\varphi_\xi(|v - u_p|_r, |\omega_1 - W_{1,p}|, \ldots, |\omega_s - W_{s,p}|),$$

$$u, v \in R^2; W_j, \omega_j \geq 0, ; \xi_i, \xi_{5,j}, \xi_{6,j} \in [0, 4], i = 0, 1, 2,$$

$$3, 4, j = 1, 2, \ldots, s, \xi_2 \in [0, 15] \Bigg\},$$

where $$\varphi_\xi(\tau_0, \tau_1, \ldots \tau_s) = \xi_0 \tau_0^{\xi_1} + \xi_2 e^{\left(-\xi_3 \tau_0^{\xi_4} - \sum_{j=1}^{s} \xi_{5,j} \tau_j^{\xi_{6,j}}\right)}.$$

Then the construction of the main learning machine goes through the same steps as previously described. To illustrate this, the prediction of the BG concentration after the injection of $W_{bol}$ insulin units made at the time $t=t_{bol}$ is considered. The data allows an input to be a vector ($\{t_i, y_i\}_{i=p}^{m+p-1}, W_{1,p}$), where $t_{m+p-1}=t_{bol}+10$ (min), $W_{1,p}=W_{bol}$ for $t_i\in[t_{bol},t_{bol}+H_{bol}]$, and $W_{1,p}=0$ for $t\in[t_{bol}+H_{bol},t_{next}]$, $t_{next}$ being the moment of the next injection made after $t=t_{bol}$. In this way the influence of the injected short-acting insulin outside of the period $[t_{bol},t_{bol}+H_{bol}]$ is ignored. For $t_{m+p-1}=t_{bol}+10$ (min), $H_{bol}=70$ (min), it reflects the fact that the onset of such an insulin occurs approximately within 10-15 minutes (therefore, kernels $K(u,v;W_1,\omega_1)$ are in operation starting from $t=t_{m+p-1}=t_{bol}+10$ (min)), peaking in 30-90 minutes (Snetselaar: "*Nutrition counselling skills for the nutrition care process*", Jones and Bartlett Publishers, 2009). In this case, the function $\varphi_\xi$ determining the kernels of the main learning machine is reduced to the following form $$\varphi_\xi(\tau_0, \tau_1) = \xi_0 \tau_0^{\xi_1} + \xi_2 e^{-\xi_3 \tau_0^{\xi_4} - \xi_{5,1} \tau_1^{\xi_{6,1}}}$$

and the kernels $K_i \in K'$, $i=1, \ldots, 4$ are chosen as in the above, to learn the prediction kernel parameters ($\alpha, \beta, \gamma, \lambda_+$) by considering the training set as input: $(a_p^{(\mu)}, b_p^{(\mu)}, W_{1,p}^{(\mu)}) \rightarrow$ output: $(\alpha_p^{(\mu)}, \beta_p^{(\mu)}, \gamma_p^{(\mu)}, \lambda_{+,p}^{(\mu)})$.

In particular, the values $\xi_0=\xi_1=0$, $\xi_2=1$, $\xi_4=2$ and $\xi_{6,1}=2$ have been fixed in the experiments. As to the values of $\xi_3$ and $\xi_{5,1}$, they are different for different kernels $K_i$, $i=1, 2, 3, 4$. For example, for one of subjects we have $\xi_3=0.01$ and $\xi_{5,1}=0.002$ for the kernel $K_1$, $\xi_3=0.001$ and $\xi_{5,1}=2$ for the kernel $K_2$, $\xi_3=0.35$ and $\xi_{5,1}=2$ for the kernel $K_3$, and $\xi_3=0.0001$ and $\xi_{5,1}=2$ for the kernel $K_4$. This is illustrated with the data of Subject1 and Subject5 collected around standard boluses at the lunch time. For training CGM-data and bolus amounts $W_{1,p}=W_{bol}$ collected around lunches of the first three days at hospital are used. The trained machine has been tested for 30 minutes ahead prediction during four days out of hospital after the boluses at lunch and dinner time. As mentioned earlier, this block of the main learning machine is active to make a prediction at moments $t_{m+p-1}$ from $t_{bol}+10$ (minutes) to $t_{bol}+40$ (minutes). Its performance has been evaluated using CG-EGA and Clarke's-EGA, and comparison has been made with the predictor blind to the pumped insulin (blind predictor).

FIG. 18 shows the performance of a special event training predictor using CG-EGA, FIG. 19 shows the performance of a blind predictor using CG-EGA, and FIG. 20 shows the performance test using Clarke's-EGA. From FIGS. 18-20 it can be seen that the use of additional information allows an improvement of predictions. It is stressed that this does not require a change of the two level architecture of the proposed predictor. Simply, a new block related with the kernels $K(u,v;W_1,\omega_1)$ is added to the main learning machine.

The numerical experiments performed with the present data and the available information about the performance of time-series based prediction models (Reifman et al.), allows the conclusion that for half an hour and one hour prediction horizons the adaptive regularization networks performs better than time-series models. For half an hour prediction, which is most often discussed in the literature, the reliability of adaptive regularization networks is level with CGM-sensors reliability: in all cases the predictor and the sensor have almost the same percentage of clinically acceptable (A+B zones of EGA) and erroneous reading (D zone).

Moreover, the present predictor mimics CGM-sensors in the sense that in terms of CG-EGA with reference to CGM-data its performance is similar to sensors performance reported in the literature (e.g. Kovatchev et al.: "*Comparison of the numerical and clinical accuracy of four continuous glucose monitors*", Diabetes Care, 31:1160-1164, 2008) with reference to blood glucose values.

Figure 21:
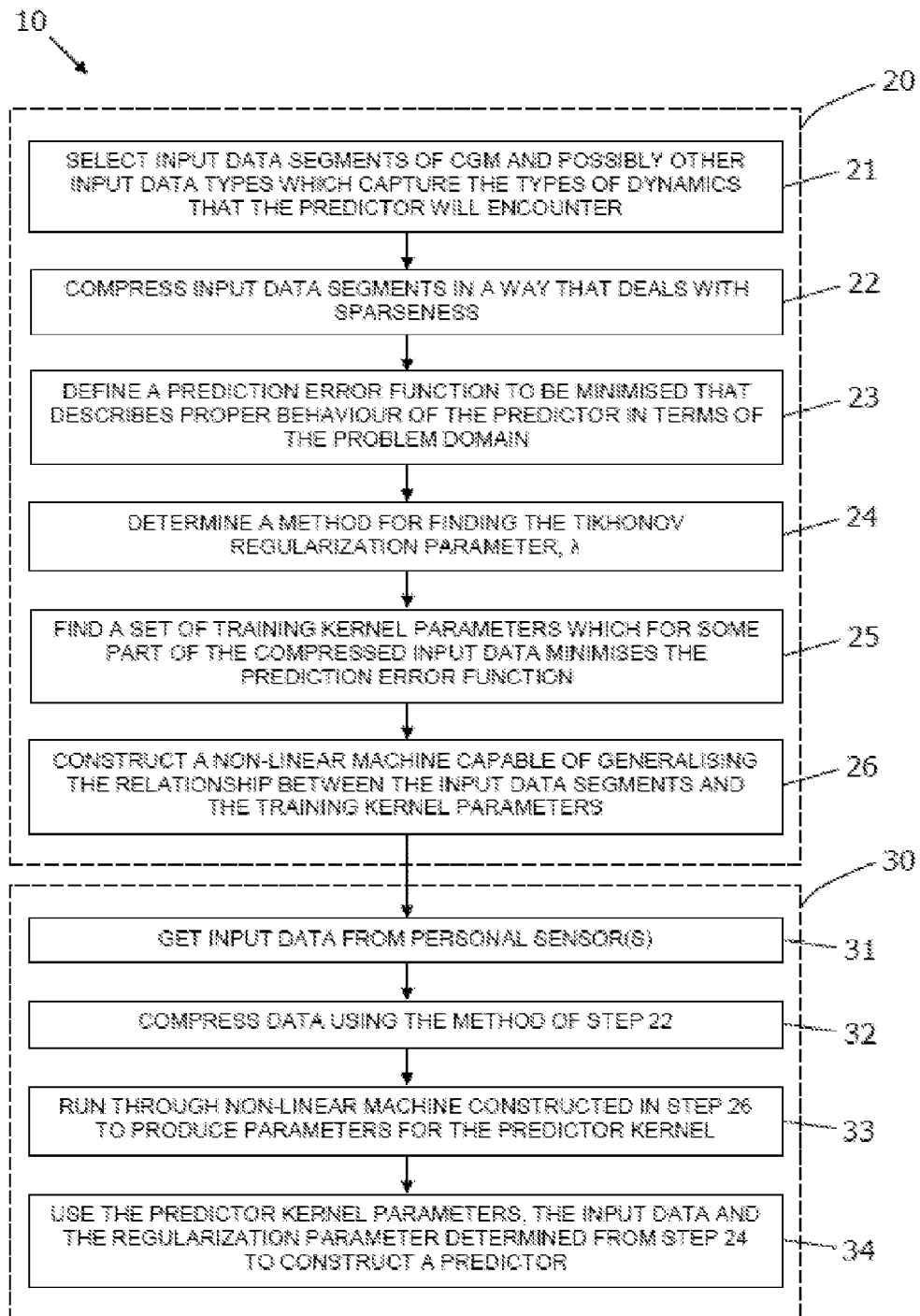
FIG. 21 is a flow diagram depicting steps of a method according to an exemplary embodiment of the invention.

FIG. 21 is a flow diagram depicting steps of a method 10 for predicting the future glycaemic state of a subject according to an embodiment of the present invention. The flow diagram can be seen as an overview of the above described method for constructing a predictor, and so each step is executed in accordance therewith. The method 10 comprises a series of training steps initially performed in a training sequence 20 followed by a series of prediction steps in a prediction sequence 30. In the training sequence 20, at step 21, input data segments of past glucose measurements, and possibly also of other measurements, that capture the types of dynamics that the predictor will encounter are selected. These data are compressed at step 22 to deal with potentially sparse and irregularly sampled input. At step 23 an error function to be minimised is defined that penalises heavily missed predictions in the hypo- and hyperglycaemia areas. The exact form of the error function is not constrained, but the general function of it is constrained by biology in the sense that hypo- and hyperglycaemia are more important events for the predictor than an intermediate range condition. At step 24 the quasi-balancing principle is chosen as the method for determining the approximate optimal value of the Tikhonov regularization parameter, $\lambda$. On the basis of that a set of training kernel parameters ($\alpha,\beta,\gamma,\lambda$), which for some part of the compressed input data minimises the error function, are established at step 25, and following that, at step 26, a trained non-linear relationship between the testing data segment and the desired parameter values is created. Given that relationship, a predictor is constructed in the prediction sequence 30 based on personal sensor data received at step 31. The predictor is constructed in a multistage process comprising a prediction setting stage (steps 32 and 33) and a subsequent prediction execution stage (step 34). During the prediction setting stage, the received personal sensor data are compressed, at step 32, in a manner similar to that which is used in the data segment compression of step 22. The thus compressed data are then at step 33 run through the non-linear machine constructed at step 26, whereby the parameters for the predictor kernel are established. Finally, during a subsequent prediction execution stage, at step 34, these parameters are used together with the input data and the regularization parameter to construct the prediction. The form of the prediction is fixed by the type of Tikhonov regularization used, e.g. iterative vs. non-iterative regularization. Generally, though, the prediction is a continuous function capable of producing predicted values from the end of the input data to any arbitrary future point in time.

Figure 22:
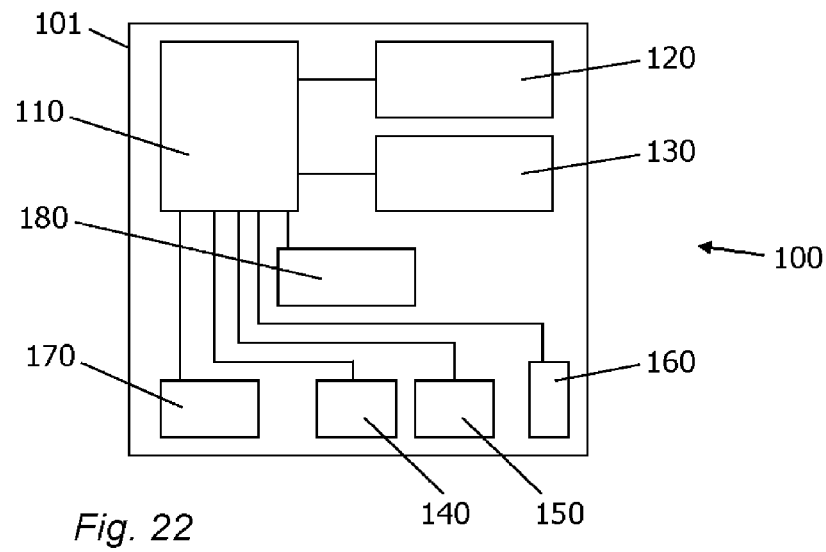
FIG. 22 shows a schematic representation of a glucose prediction device according to an embodiment of the invention.

FIG. 22 shows a simplified block diagram of an exemplary glucose prediction device 100 incorporating the above described prediction algorithm. The glucose prediction device 100 includes a housing 101, electronics 110 including a processing unit and a memory, a display 120 for presenting results to the user in the form of numbers, graphs and other indicators, a user input keyboard 130 providing the user with an opportunity for manually inputting information, an RF receiver 140 for wirelessly receiving data transmitted from one or more other devices such as a blood glucose meter, a continuous glucose monitor, or an insulin injection device, an RF transmitter 150 for wirelessly communicating results to a further external device such as e.g. a PC or a mobile phone, a speaker 160 adapted to produce an audible signal, e.g. an alarm for catching the attention of the user, a battery 170 supplying energy to the device, and a strip port 180 adapted to receive and read a glucose test strip (not shown). Other elements may additionally be included in the glucose prediction device 100, which device may be a stand-alone device, a remote controller, e.g. for an infusion pump, a remote receiver in a CGM system, a PDA, a mobile phone, a portable music player, a portable multi-purpose device, a PC, or indeed any electronic device comprising a processing unit capable of executing the glucose prediction algorithm. It is noted that means for wireless communication other than RF may be employed, for example IR, NFC, Bluetooth, induction etc.

The glucose prediction device 100 may, alternatively, be a simple relay device, e.g. without a display, capable of receiving data from one or more medical devices, processing the data in accordance with the above described algorithm, and transmitting the processed data to a further external device, e.g. for display of results.

Figure 23:
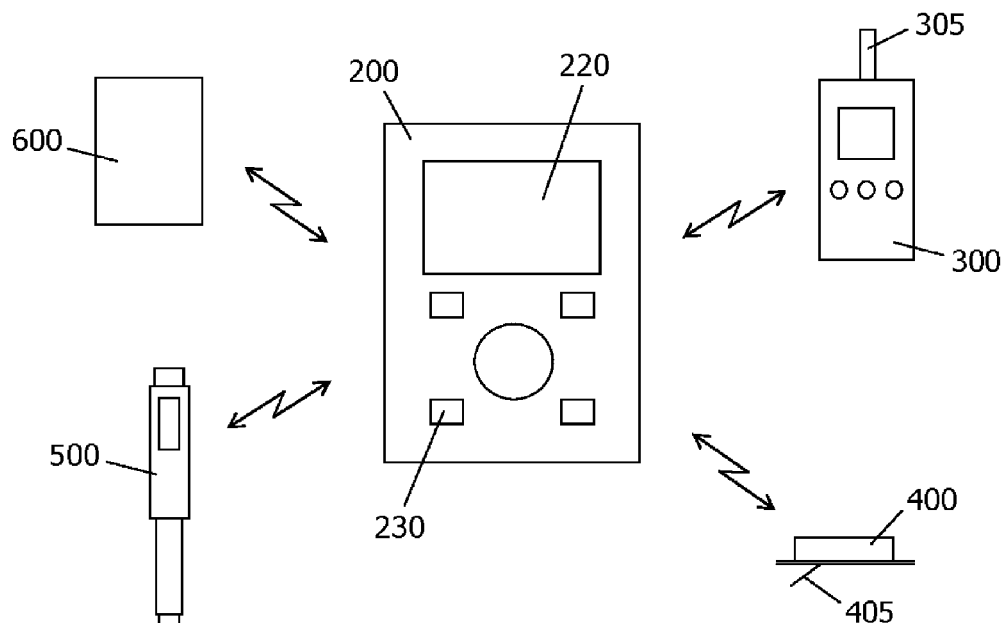
FIG. 23 shows a glucose prediction device according to an embodiment of the invention in wireless communication with exemplary data input devices.

FIG. 23 depicts a glucose prediction device 200 of the type described with respect to FIG. 22, except that it does not comprise a strip port and a glucose meter function. The glucose prediction device 200 is in wireless communication with a blood glucose meter 300, a continuous glucose monitor 400, an insulin injection pen 500, and some other personal sensing device 600, such as e.g. a heart rate monitor, a pulse meter, a breath monitor, or the like useful for providing physiologic measurements indicative of the current glycaemic state of the user. The blood glucose meter 300 is adapted to receive a glucose test strip 305 which has been, or which is to be, wetted with a drop of blood from the user. Within a few seconds, the blood glucose meter 300 displays a test result and automatically transmits this result to the glucose prediction device 200 via an RF connection. The continuous glucose monitor 400 is adapted to be placed on the skin of the user. In use, a needle-type sensor 405 residing in the subcutaneous tissue continuously or near-continuously measures the local tissue glucose level, and the data is transmitted automatically, e.g. each minute or each five minutes, via an RF connection to the glucose prediction device 200. The insulin pen 500 is adapted to log information pertaining to injections performed, such as dose size, time of injection and type of insulin, and to transmit this information to the glucose prediction device 200 via an RF connection. The other personal sensing device 600 is likewise adapted to wirelessly transmit information pertaining to the specific measurements performed therewith to the glucose prediction device 200.

Further, the user may manually input information, such as calorie intake, time of meal consumption etc., via keys 230 on the glucose prediction device 200. Alternatively, the meal related information may be conveyed to the glucose prediction device 200 by wireless transmission from another electronic device.

Depending on the incoming data the glucose prediction algorithm will use the received information from one or more of the additional devices as input to the Data Pool and construct supervising learning machines and so on in accordance with the above described. When the glucose prediction device 200 has produced a result, a display 220 will present the projected glycaemic state as a continuous function of time for a given prediction horizon. In case of impending hypo- or hyperglycaemic events the glucose prediction device 200 will sound an alarm to alert the user, which may then take preventive action.

For example, if a short term prediction is low the user could respond with an immediate carbohydrate intake, and if a long term prediction is low the user could respond with cutting short her/his exercise routine. If a short term prediction is high, on the other hand, the user could respond with injecting fast acting insulin, and if a long term prediction is high the user could respond with a moderate exercise.

The results reported in the literature show that the prediction accuracy crucially depends on the sampling rate of the data used for a prediction. For example, the predictor proposed by Reifman et al. requires the data sampled at a frequency of one minute. It is reported that this predictor is calibrated once for one individual and then can be applied, without further adjustments, to predict other individuals. This is in sharp contrast with the predictor proposed by Sparacino et al., which is also based on the time-series identification methodology, but should be updated continuously for each individual. Reifman et al. hypothesize that the capability of their predictor to be portable from individual to individual without readjustment is because of the higher sampling rate of available CGM data (1 minute versus 3 minutes for the predictor of Sparacino et al.).

Notably, all predictors described in the recent literature (Sparacino et al., Reitman et al., Zanderigo et al., Eren-Oruklu et al., and Pappada et al.: "*Development of a neural network for prediction of glucose concentration in Type 1 Diabetes patients*", Journal of Diabetes Sci. and Tech., 2(5): 792-801, 2008) use CGM data with sampling frequency ranges from 1-5 minutes. From this viewpoint the present predictor based on adaptive regularization networks provides improved results compared with known predictors, since for a half an hour prediction horizon, for example, it gives a prediction of the same or better quality from CGM data sampled at a frequency of 10 minutes, and in spite of a low sampling rate it can be made portable from individual to individual without any readjustment.

A use of the present predictor may be particularly attractive in the situation, where one would like the prediction output to be a direct estimate of the blood glucose concentration and not a prediction of what a CGM monitor will show. Such a prediction presupposes that the input comprises values of the blood glucose concentration as well. In that case a low sampling rate is a desirable feature of a predictor, since it reduces an individual's burden of performing manual blood glucose measurements.

The features of embodiments of the methods described herein may be implemented in software and carried out on a mobile device or other data processing system caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software. According to another aspect a computer program comprises program code means for causing a data processing system or device to perform one or more of the methods disclosed herein, when said computer program is executed on the data processing device or system.

In the following further embodiments of the methods disclosed herein will be described.

It is well known (see, e.g., [1] and references therein) that regularization algorithms can be profitably used in the context of learning theory, when one approximates the minimizer of expected risk by elements of some Reproducing Kernel Hilbert Space. Once a regularized kernel based learning algorithm is applied, two questions should be answered. One of them is how to choose a regularization parameter, and another one is how to choose a kernel, since in several practically important applications, such as the prediction of the blood glucose, for example, a kernel is not a priori given. Usually these questions are discussed separately (see, e.g., [9] and [2]). In this disclosure, probably for the first time, a learning algorithm with kernels and parameters chosen in the course of regularization is proposed. The construction of such an algorithm is motivated by the problem of monitoring and predicting the blood glucose concentration, which is extremely important in Diabetes therapy.

In its simplest form, this therapy is based on rules that are used to estimate the necessary amount of insulin injection or possibly of additional snacks. Keeping in mind that the onset of insulin occurs within 10-30 minutes, and the onset of meal responses on glucose levels occurs approximately within 5-10 minutes, it is important to know future blood glucose level at least 20 minutes ahead of time. In this disclosure, we show that proposed regularization learning algorithm in principle allows a prediction with this horizon. It is interesting to note that in numerical experiments with proposed algorithm only 2 past blood glucose measurements sampled with time interval of 5 minutes were necessary to make a prediction with a clinically acceptable accuracy. This feature of the algorithm is very promising since potentially it may reduce the burden associated with blood sampling.

In the next section, we give some theoretical background and introduce our approach with a few academic illustrations. Later we discuss a possibility to use proposed approach in reading blood glucose level from subcutaneous electric current measurements. It turns out that this approach can be seen as an answer to the request [6] for "more sophisticated procedure" to calibrate blood glucose meters. Finally, we present one more embodiment of a blood glucose predictor based on proposed approach and report the results of numerical experiments with data from clinical trials. In further embodiment a prediction is made from past subcutaneous electric current readings of a subject, which are transformed into estimations of blood glucose concentrations by a regularized learning algorithm in an adaptively chosen reproducing kernel spaces.

The Basic Regularized Learning Algorithm and Related Issues

In a regression setting the problem of learning from examples can be formulated in this way: given a training set $z=\{z_i=(x_i,y_i), i=1, 2, \ldots, l\}$ of examples obtained by sampling $l$ times the set $X \times Y$, $X \subset \mathbb{R}^d$, $Y \subset \mathbb{R}$, according to an unknown probability measure $\rho$ on $X \times Y$, approximate the regression function $f_\rho$, which minimizes the so-called expected risk $$\varepsilon(f):=\int_{X \times Y}(y-f(x))^2 d\rho(x,y).$$

A widely used approach to approximate $f_\rho$ from given training set $z$ consists in finding the function $f(x)=f(K, \lambda, z; x)$ that minimizes the regularization functional $$T(K, \lambda, z; f) := \frac{1}{l}\sum_{i=1}^{l}(y_i - f(x_i))^2 + \lambda\|f\|_K^2, \quad (i)$$

where $\lambda$ is a positive regularization parameter, and $\|\cdot\|_K$ is the standard norm in a Reproducing Kernel Hilbert Space (RKHS) $\mathcal{H}_K$ defined by a symmetric positive definite function K: $X \times X \to \mathbb{R}$.

From the representer theorem [14] it follows that the minimizer of (i) has the form $$f(K, \lambda, z; x) = \sum_{i=1}^{l} c_i^\lambda K(x, x_i) \quad (ii)$$

for a real vector $\vec{c}_\lambda=(c_1^\lambda, c_2^\lambda, \ldots, c_l^\lambda)$ of coefficients such that $$\vec{c}_\lambda = (\lambda l \mathbb{I} + \mathbb{K})^{-1}\vec{y}$$

where $\mathbb{I}$ is the unit matrix of the size $l$, $\mathbb{K}$ is the kernel matrix with entries $K_{ij}=K(x_i,x_j)$, $i,j=1, 2, \ldots, l$, and $\vec{y}=(y_1, y_2, \ldots, y_l)$ is the vector of outputs.

Once the regularized learning algorithm (i), (ii) is applied, two issues should be addressed. One of them is how to choose a regularized parameter $\lambda$. When the kernel K is fixed, this is typically solved by means of some training data splitting. (see, for example, recent paper [2], and references therein).

Another issue which needs to be addressed is one of a kernel choice, since in several practically important applications a kernel K is not a priori given. This issue is much less studied. It has been discussed recently in [9] (see also [4]), but, as it will be seen from our discussion below, the kernel choice suggested in [9] does not fit well the application we have in mind.

Therefore, we will propose another kernel choice rule, which is based on a splitting of training data. Then for choosing a regularization parameter $\lambda$ we need a rule that avoids data splitting. Such a rule, the balancing principle, has been recently introduced in the context of the theory of learning from examples [4], and it has been proved that for a fixed kernel K this rule gives an order-optimal rate of the approximation error as $l \to \infty$. Moreover, in [4] one can also find a heuristic counterpart of the balancing principle, which can be used in practice, when the amount $l$ of training data is not so large. This heuristic rule, called quasi-balancing principle, can be seen as a combination of the balancing principle [4] and quasi-optimality criterion [13], which is the most ancient of rules known in the regularization theory.

To apply the quasi-balancing principle [4] one needs to calculate the approximations $f(K, \lambda, z; \cdot)$ given by (ii) for $\lambda$ from a finite part of a geometric sequence $$\Lambda_q^\nu = \{\lambda_s = \lambda_0 q^s, s=0,1,2, \ldots \nu\}, q>1. \quad (iii)$$

Then one needs to calculate the norms $$\sigma_{emp}^2(s) = \|f(K, \lambda_s, z; \cdot) - f(K, \lambda_{s-1}, z; \cdot)\|_{\{x_i\}_{i=1}^l}^2 := \quad (iv)$$
$$\frac{1}{l}\sum_{i=1}^{l}\left(\sum_{j=1}^{l}(c_j^{\lambda_s} - c_j^{\lambda_{s-1}})K(x_i, x_j)\right)^2$$

$$\sigma_{\mathcal{H}_K}^2(s) = \|f(K, \lambda_s, z; \cdot) - f(K, \lambda_{s-1}, z; \cdot)\|_K^2 := \quad (v)$$
$$\frac{1}{l}\sum_{i=1}^{l}\sum_{j=1}^{l}(c_i^{\lambda_s} - c_i^{\lambda_{s-1}})(c_j^{\lambda_s} - c_j^{\lambda_{s-1}})K(x_i, x_j),$$

and find $$\lambda_{emp} = \lambda_h, h = \arg\min\{\sigma_{emp}^2(s), s=1,2, \ldots, \nu\},$$

$$\lambda_{\mathcal{H}_K} = \lambda_p, p = \arg\min\{\sigma_{\mathcal{H}_K}^2(s), s=1,2, \ldots, \nu\}.$$

Finally, in accordance with the quasi-balancing principle one chooses a value of the regularization parameter $\lambda = \lambda_+ \in \Lambda_q^v$ given by $$\lambda_+ = \min\{\lambda_{emp}, \lambda_{\mathcal{H}_K}\}. \quad (vi)$$

Let us return to the discussion on a choice of a kernel K. It is worth to note that in this paper we are interested in constructing regularized approximants of the form (ii), which will approximate/predict the values of a function of interest (the blood glucose concentration) at points outside of the scope of inputs $\{x_i\}$ from the training set. We find it suitable to call such an approximation as a prediction of the extrapolation type and need a kernel choice rule that will allow good performance in such a prediction.

As we already mentioned, the kernel choice issue has been recently discussed in [9]. But the approach advocated there seems to be not appropriate for a prediction of the extrapolation type.

Indeed, the idea of [9] is to recover from given training set z the kernel K generating a RKH-space, where inaccessible target function $f_\rho$ lives, and then use this kernel for constructing an approximant (ii).

To illustrate that such an approach may fail in a prediction of the extrapolation type we use the same example as in [9], where $$f_\rho(x) = 0.1\left(x + 2\left(e^{-8\left(\frac{4\pi}{3}-x\right)^2} - e^{-8\left(\frac{\pi}{2}-x\right)^2} - e^{-8\left(\frac{3\pi}{2}-x\right)^2}\right)\right),$$

$X \in [0, 2\pi]$, and the training set consists of points $$\left\{x_i = \frac{\pi i}{10}, i = 0, 1, 2, \ldots, 15\right\}$$

accompanied by $y_i = f_\rho(x_i) + \in$ with random $\in$ sampled uniformly in the interval $[-0.02, 0.02]$. Note that in [9] the target function $f_\rho$ has been chosen in such a way that it belongs to RKHS generated by the kernel $K(x,u) = xu + e^{-8(x-u)^2}$. Using this kernel in the regularized learning algorithm (i), (ii), as it is suggested in [9], one can successfully predict the values of the target function $f_\rho$ at any point of $[0, 1.5\pi]$, which is the scope interval for the inputs $$\left\{x_i = \frac{\pi i}{10}, i = 0, 1, \ldots, 15\right\}.$$

Figure 24:
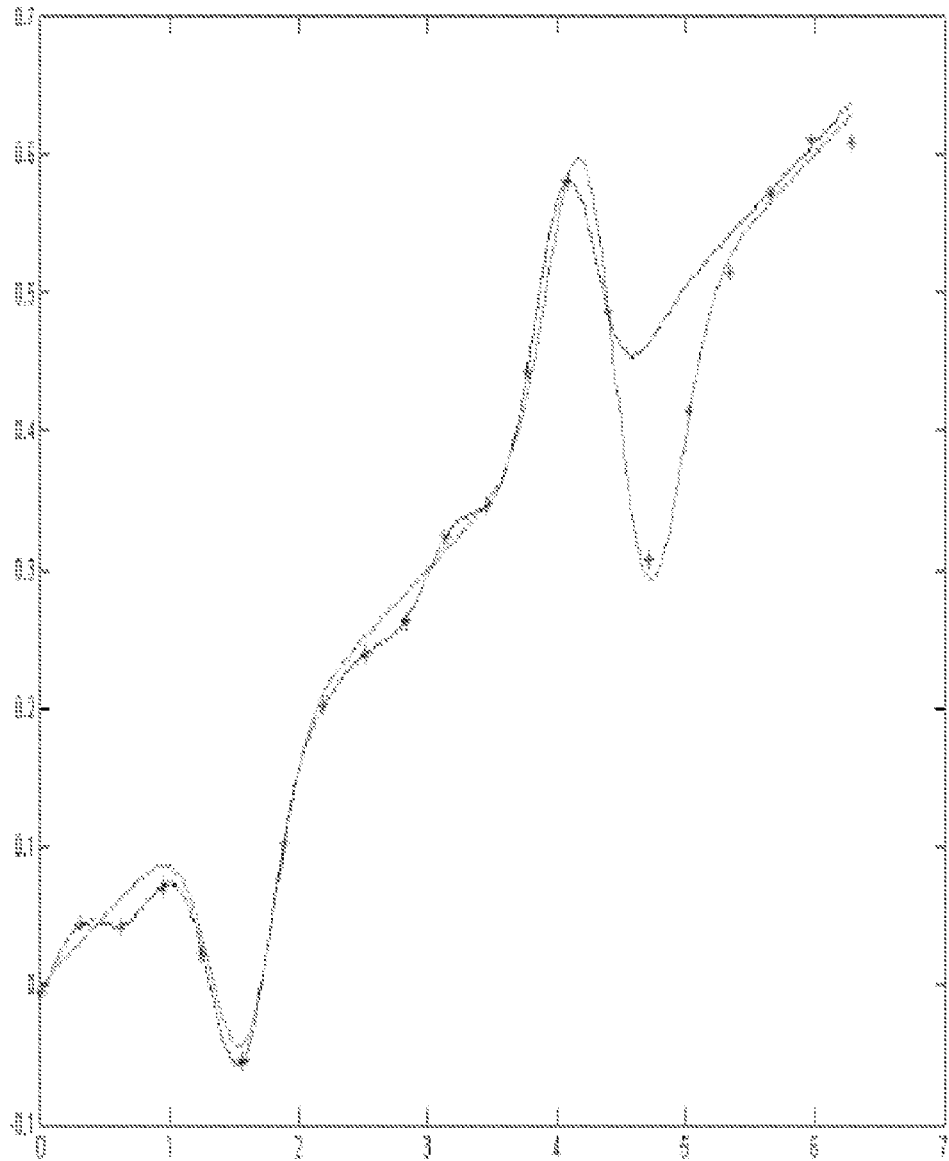
FIG. 24 illustrates the prediction performance of a prior art method when predicting an exemplary function.

It can be seen in the FIG. 24. At the same time, this figure shows that the quality of the prediction at the points $x \in [1.5\pi, 2\pi]$ being beyond the scope of the training set inputs $\{x_i\}$ is rather poor. Observe that the FIG. 24 displays the performance of the approximant (ii) with the best $\lambda$ from the set (iii), where $\lambda_0 = 10^{-6}$, $q = 1.5$, $v = 20$. This best $\lambda$ has been chosen "by hands" with the knowledge of "right" answer $f = f_\rho$. It means that the choice of the regularization parameter $\lambda$ cannot improve the performance of the approximant (i), (ii) given by the "ideal" kernel, that is, the kernel $K(x,u) = xu + e^{-8(x-u)^2}$ used to generate the target function $f_\rho$ (see [15] for more details).

Figure 25:
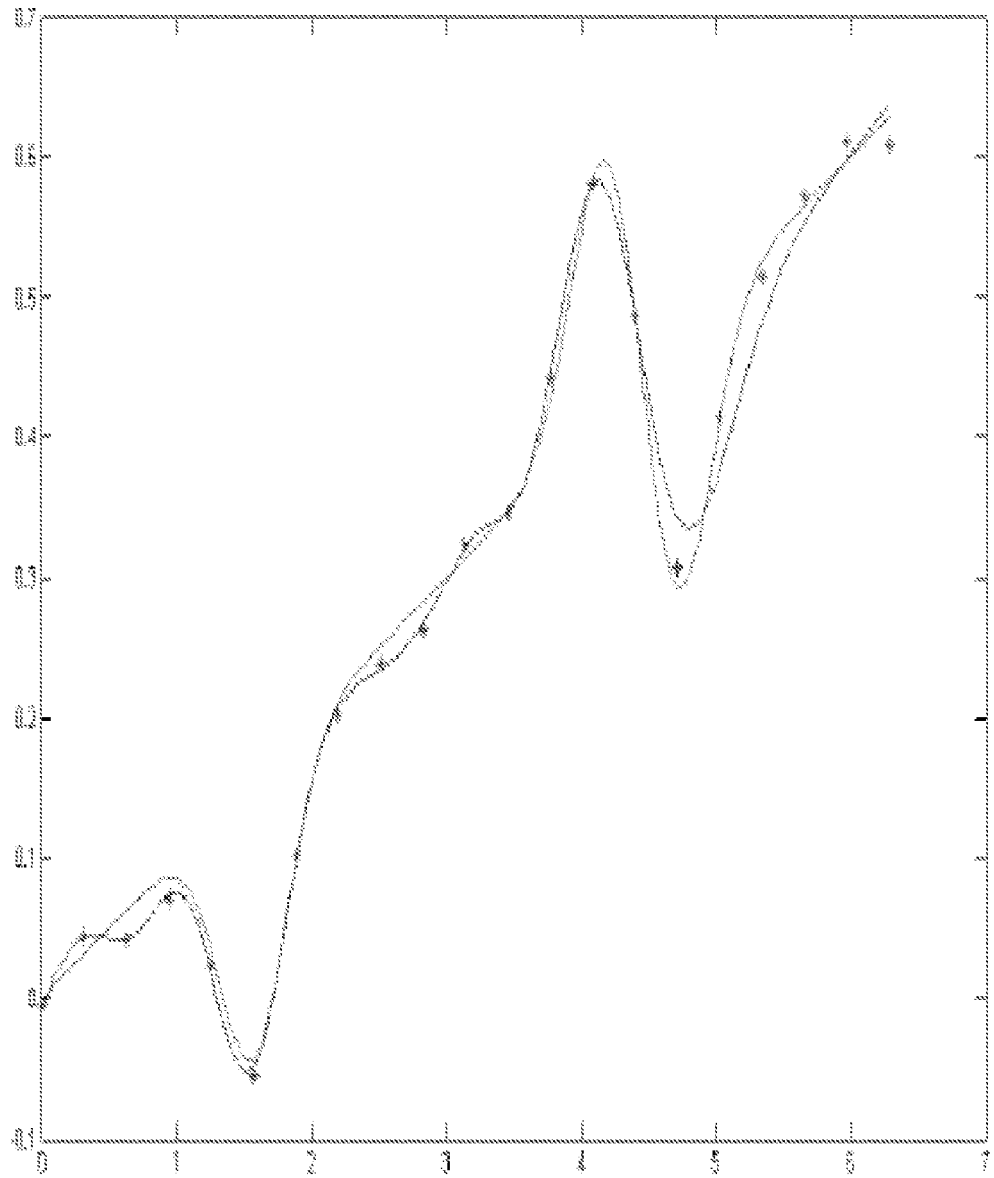
FIG. 25 illustrates the prediction performance of an examples of a prediction method described herein when applied to the same exemplary function as in FIG. 24.

The FIG. 25 displays the performance of the approximant (ii) constructed for the same training set z, but with the use of the kernel $K(x,u) = (xu)^{1.2} + e^{-2.6(x-u)^2}$. As one can see, the approximant based on this kernel performs much better compared to the FIG. 24. Note that the regularization parameter $\lambda$ for this approximant has been chosen from the same set $\Lambda_q^v$ as above by means of the quasi-balancing principle (vi). The kernel improving the approximation performance has been chosen from the set $$\kappa = \{K(x,u) = (xu)^\alpha + \beta e^{-\gamma(x-u)^2}, \alpha, \beta, \gamma \in [10^{-4}, 3]\} \quad (vii)$$

as follows.

At first, given training set z has been splitted into two parts $z_T$ and $z_P = z \setminus z_T$ such that, for example, the convex hull of inputs $\{x_i\}$ from $z_T$ does not contain inputs from $z_P$.

The first part $z_T$ has been used for constructing approximants $f = f(K, \lambda, z_T; \cdot)$, $K \in \kappa$, which minimize the regularization functionals $$T(K, \lambda, z_T; f) = \frac{1}{|z_T|} \sum_{i:(x_i, y_i) \in z_T} (y_i - f(x_i))^2 + \lambda \|f\|_K^2, \quad (viii)$$

where $|z_T|$ is the total number of elements from $z_T$. It is clear that $T(K, \lambda, z_T; f)$ is just the functional (i) written for $z = z_T$.

The performance of each approximant $f = f(K, \lambda, z_T; \cdot)$, $K \in \kappa$, has been measured by a value of the functional $$P(K, \lambda, z_P; f) = \frac{1}{|z_P|} \sum_{i:(x_i, y_i) \in z_P} (y_i - f(x_i))^2. \quad (ix)$$

Then the kernel of our choice is $K = K(\kappa, \mu, \lambda, z; x, u)$ that minimizes the functional $$Q(\mu, \lambda, z_T; f) := \mu T(K, \lambda, z_T; f(K, \lambda, z_T; \cdot)) + (1-\mu) P(K, \lambda, z_P; f(K, \lambda, z_T; \cdot)) \quad (x)$$

over the set of kernels $\kappa$. Note that the parameter $\mu$ here can be seen as a performance regulator on the sets $z_T$ and $z_P$. For a prediction of the extrapolation type it seems to be reasonable to take sufficiently small $\mu$. The kernel choice rule based on the minimization of (x) can be seen as a generalization of the rule proposed in [9], where it has been suggested to select the kernel as the minimizer of the functional $T(K, \lambda, z; \theta(K, \lambda, z; \cdot))$ over kernel set $\kappa$. It corresponds to (x) with $\mu = 1$, $z = z_T$, and from our discussion above one can conclude that such a choice is mainly oriented towards a prediction within the scope of inputs $\{x_i\}$ from a training set.

The above mentioned kernel $K(x,u) = (xu)^{1.2} + e^{-2.6(x-u)^2}$ (see FIG. 25) has been chosen from the set (vii) as an approximate minimizer of (x) with $\mu = 0.01$, $\lambda = \lambda_1 = 1.5 \cdot 10^{-6}$, $|z_T| = |z_P|$. Such a minimizer has been found by the full search over the grid of parameters $\alpha_i = 10^{-4} i$, $\beta_j = 10^{-4} j$, $\gamma_k = 10^{-4} k$, i, j, k = 1, 2, ..., determining kernels from (vii). We choose this naive procedure since in application we have in mind the minimization of (x) can be performed off-line, so the computation cost is not a crucial issue.

The kernel choice rule based on the minimization of the functional (x) is rather general. Next theorem justifies this choice for kernel sets $\kappa$ described as follows.

Let $\Omega$ be a compact Hausdorff space. Consider a mapping G from $\Omega$ into the set of all symmetric positive definite kernels on X×X We say a mapping G is continuous provided that for each x, u∈X the function $\omega \mapsto G(\omega)(x, u)$ is continuous on $\Omega$, where $G(\omega)(x, u)$ is the value of the kernel $G(\omega)$ at the point (x, u)∈X×X. Each such a mapping G determines a set of kernels $$\kappa = \kappa(\Omega, G) = \{G(\omega) : \omega \in \Omega\}.$$

Note that the kernel set (vii) is a special case of $\kappa(\Omega, G)$, where $\Omega=[10^{-4}, 3]^3$, and for $\omega=(\alpha,\beta,\gamma)\in\Omega$ $G(\alpha,\beta,\gamma)(x,u)= (xu)^\alpha+\beta e^{-\gamma(x-u)^2}$.

Theorem 0.1. Let $\Omega$ be a compact Hausdorff space, and G be a continuous mapping from $\Omega$ into the set of all symmetric positive definite kernels on X×X Then there exists a kernel $K_o\in\kappa(\Omega, G)$ such that $$Q(\mu,\lambda,z,K_0)=\inf\{Q(\mu,\lambda,z,K), K\in\kappa(\Omega,G)\}.$$

This theorem is proven in a recent paper [10].

In the next sections the kernel choice rule based on the minimization of the functional Q will be used in the context of the blood glucose monitoring and prediction.

Remark 0.2. The minimizer $f(K, \lambda, z_T, \bullet)$ of the functional (viii) can be seen as a Tikhonov regularized solution of the equation $$S_{z_T}f=\vec{y}, \qquad (xi)$$

where $S_{z_T}: \mathcal{H}_K\to\mathbb{R}^l$, $l=|z_T|$, is the sampling operator defined by $(S_{z_T}f)_i=f(x_i)$, $i:(x_i, y_i)\in z_T$, and $\vec{y}=(y_i)\in\mathbb{R}$.

When a kernel K has already been chosen, other methods of general regularization theory can also be applied to the equation (xi), as it has been analysed in [1]. In particular, one can apply iterative Tikhonov regularization. In this case regularized solution $f=f(K, \lambda, z_T, \bullet)$ also has the form (ii), but $\vec{c}=(l^2\lambda\mathbb{I}+\mathbb{K}^2)^{-1}\mathbb{K}\vec{y}$.

Reading Blood Glucose Level from Subcutaneous Electric Current Measurements

Information about a patient's current blood glucose concentration is extremely important in Diabetes therapy. Minimal-invasive continuous glucose monitoring (CGM) systems providing estimated blood glucose level almost in real-time have been recently developed and approved. For example, needle based electrochemical sensors, such as Abbott Freestyle Navigator, measure electrical signal (ADC counts) in the interstitial fluid (ISF) and return ISF glucose concentration (mg/dl) exploiting some internal calibration procedure. This ISF glucose reading is taken as an estimate of current blood glucose concentration, which is of interest in Diabetes therapy.

At the same time, it is known (see [6] and references therein) that the equilibration between blood and ISF glucose is not instantaneous. Therefore, CGM devices sometimes give a distorted estimation of blood glucose level.

In [6] it has been shown how such a distortion can be compensated through the use of a differential equation based model of blood-interstitium kinetics. Within this model a blood glucose concentration can be recovered from ISF glucose level provided the latter one was accurately determined from subcutaneous electric current measurements by means of a calibration procedure.

The results of [6] show that in this approach the role of calibration is really crucial. In particular, these results suggest that further improvements of blood glucose reconstruction require more sophisticated procedures than the standard calibration by which ISF glucose is determined is CGM systems, such as Abbott Freestyle Navigator.

At the same time, one could try to circumvent the calibration issue using regularized learning algorithms discussed in the previous section. Then in these algorithms the input $x_i$ represents subcutaneous electric current (ADC counts) measured by a CGM sensor and the output $y_i$ represents corresponding blood glucose concentration (mg/dl). Unlike the model used in [6] the ISF glucose level is not assumed to be known now.

To illustrate this approach we use data sets of nine type 1 diabetic subjects studied in the Endocrinology Department at Centre Hospitalier Universitare de Montpellier (CHU, France) and in the Department of Clinical and Experimental Medicine at the University of Padova (UNIPD, Italy) within the framework of EU-project "DIAdvisor". The chosen number of data sets is consistent with earlier research [11], [6], where correspondingly 9 and 6 subjects have been studied.

In each subject, blood glucose concentration and subcutaneous electric current were measured in parallel for 3 days in hospital conditions. The blood glucose concentration was measured 30 times per day by the HemoCue glucose meter. Blood samples were collected every hours during day, every 2 hours during night, every 15 minutes after meals for 2 hours. Specific sampling schedule was adopted after breakfasts: 30 minutes before, mealtime, 10, 20, 30, 60, 90, 120, 150, 180, 240, 300 minutes after. Subcutaneous electric current was measured by the Abbott Freestyle Navigator every 1 minute.

For each subject the values of the blood glucose concentration and subcutaneous electric current measured at the same time during the first day were used as training data $z=\{z_i=(x_i,y_i), i=1, 2, \ldots, 30\}$. Here $x_i\in[1, 1024]$ are the current values (ADC counts) ordered in increasing order, while $y_i\in[0, 450]$ are corresponding values of the blood glucose concentration (mg/dl).

The training set z corresponding to the subject CHU102 was used for choosing the kernel K from the set (vii). For this purpose, the set was splitted into two parts $z_T=\{z_i, i=3, 4, \ldots, 28\}$ and $z_P=\{z_i, i=1, 2, 29, 30\}$. Then the kernel $$K(x,u)=(xu)^{0.89}+0.5e^{-0.0003(x-u)^2} \qquad (xii)$$

was chosen as an approximate minimizer of the functional (x) with $\mu=0.5$, $\lambda=10^{-4}$. For all 9 subjects this kernel K was used to construct a regularized estimator (i), (ii) of the blood glucose concentration that, starting from a raw electric signal $x\in[1, 1024]$ returns a blood glucose concentration $y=f(K, \lambda, z, x)$, where $z=\{z_i=(x_i,y_i), i=1, 2, \ldots, 30\}$ are subject's data collected during the first day, and $\lambda$ was chosen from (iii) in accordance with the principle (vi).

To quantify clinical accuracy of constructed regularized estimatiors we use the original Clarke Error Grid Analysis (EGA), which is accepted as one of the "gold standards" for determining the accuracy of blood glucose meters and/or predictors (see [3], [11] and references therein).

In accordance with EGA methodlgy, for each 9 subjects the available blood glucose values obtained in the HemoCue meter have been compared with the estimates of the blood glucose $y=f(K, \lambda, z, x)$. Here x is a subcutaneous current value at the moment when corresponding HemoCue measurement was executed. Since HemoCue measurements made during the first day have been used for constructing $f(K, \lambda, z, x)$, only the data from the other 2 days (60 HemoCue measurements) have been used as references in the Clarke's analysis.

Figure 26:
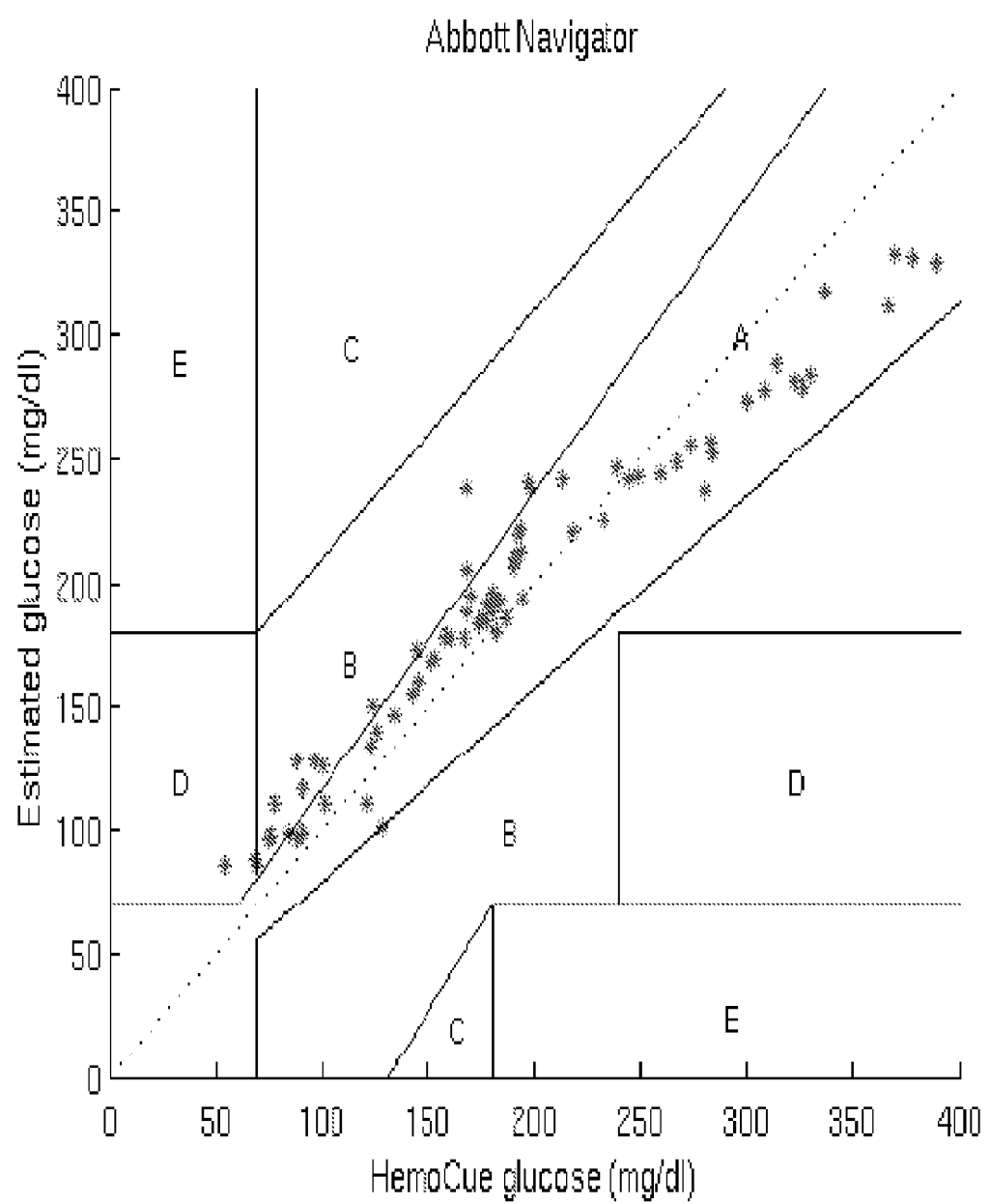
FIG. 26 shows a representative Clarke error grid for blood glucose estimations determined from the internal readings of the Abbott Freestyle Navigator.

In this analysis each pair (reference value, estimated/predicted value) identifies a point in the Cartesian plane, where the positive quadrant is subdivided into five zones, A to E, of varying degrees of accuracy and inaccuracy of glucose estimations (see FIG. 26, for example). Points in zones A and B represent accurate or acceptable glucose estimations. Points in zone C may prompt unnecessary corrections that could lead to a poor outcome. Points in zones D and E represents a dangerous failure to detect and treat. In short, the more points that appear in zones A and B, the more accurate the estimator/predictor is in terms of clinical utility.

Figure 27:
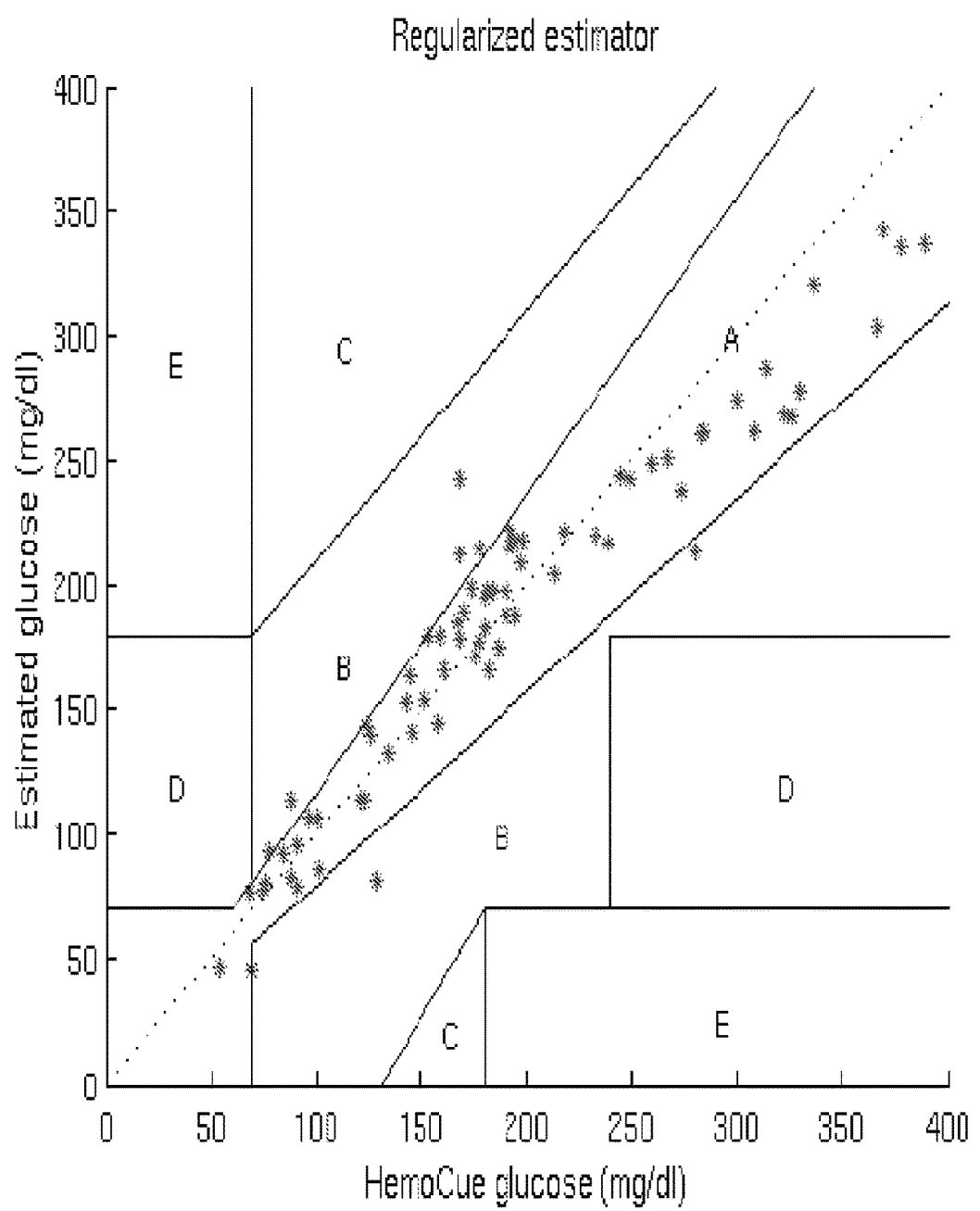
FIG. 27 shows a representative Clarke error grid for an example of a regularised blood glucose estimator as disclosed herein.

A representative Clarke error grid (subject UNIPD203) for proposed regularized blood glucose estimator is shown in FIG. 27. For comparison, in FIG. 26 the results of EGA for blood glucose estimations determined from the internal readings of the Abbott Freestyle Navigator calibrated according to the manufacturer's instruction are presented for the same subject and reference values. Comparison shows that regularized estimator is more accurate, especially in case of low blood glucose.

The results of EGA for all subjects are summarized in Table 1 (regularized estimator) and Table 2 (Abbott Freestyle Navigator).

TABLE 1

Percentage of points in EGA - zones for estimators based on the kernel (xii)

| Subject | A | B | C | D | E |
|---|---|---|---|---|---|
| CHU102 | 86.42 | 13.58 | — | — | — |
| CHU105 | 87.5 | 11.25 | — | 1.25 | — |
| CHU111 | 88.46 | 10.26 | — | 1.28 | — |
| CHU115 | 92.21 | 7.79 | — | — | — |
| CHU116 | 92.11 | 7.89 | — | — | — |
| CHU119 | 89.87 | 10.13 | — | — | — |
| CHU128 | 87.76 | 12.24 | — | — | — |
| UNIPD202 | 81.08 | 17.57 | — | 1.35 | — |
| UNIPD203 | 93.33 | 6.67 | — | — | — |
| Average | 88.75 | 10.82 | — | 0.43 | — |

TABLE 2

Percentage of points in EGA - zones for Abbott Freestyle Navigator

| Subject | A | B | C | D | E |
|---|---|---|---|---|---|
| CHU102 | 93.83 | 6.17 | — | — | — |
| CHU105 | 92.5 | 5 | — | 2.5 | — |
| CHU111 | 85.9 | 12.82 | — | 1.28 | — |
| CHU115 | 94.81 | 5.19 | — | — | — |
| CHU116 | 86.84 | 10.53 | — | 2.63 | — |
| CHU119 | 83.54 | 16.46 | — | — | — |
| CHU128 | 48.98 | 44.9 | — | 6.12 | — |
| UNIPD202 | 89.19 | 8.11 | — | 2.7 | — |
| UNIPD203 | 76 | 21.33 | — | 2.67 | — |
| Average | 83.51 | 14.5 | — | 1.99 | — |

These results allow a conclusion that in average proposed approach to reading blood glucose levels from subcutaneous electric current is more accurate than estimations given by the Abbott Freestyle Navigator on the basis of the standard calibration procedure. Proposed approach can be seen as an answer to the request [6] for "more sophisticated calibration procedure". We would like to stress that no recalibrations of regularized glucose estimators were made during 2 days assessment period. At the same time, a recalibration of the Abbott Freestyle Navigator should sometimes be made several times per day.

Prediction of Future Blood Glucose Concentration

The availability of a blood glucose predictor that would inform at any time the patient on the near future blood glucose outlook, would be highly valuable for insulin therapy of diabetes, which is one of the most difficult treatment to manage.

Mathematically, the problem can be formulated as follows. Assume that we are given m subsequent measurements/estimations $g_i, g_{i-1}, \ldots, g_{i-m+1}$ of patient's blood glucose concentration sampled with time interval $\Delta t$ at moments $t_i > t_{i-1} > \ldots > t_{i-m+1}$. The goal is to construct a predictor that will use these past measurements/estimations to predict a future blood glucose concentration $g=g(t)$ in a time interval from $t=t_i$ till $t=t_{i+n}=t_i+n\Delta t$, i.e. n steps ahead.

A multitude of methods have been proposed recently for the near-term prediction of glucose fluctuations from CGM data. Most of them are based on time-series modelling techniques (see [12], [11] and references therein).

In this section we propose another approach to blood glucose prediction, which is based on regularized learning algorithms discussed above. In accordance with this approach a predictor is comprised of two regularized learning algorithms. One of them, called supervising algorithm, is trained in choosing an adequate kernel K generating the space $\mathcal{H}_K$, where a future blood glucose profile g(t) will be reconstructed. Moreover, supervising algorithm also chooses initial term $\lambda_o$ in a geometric sequence (iii) from which a regularization parameter $\lambda$ will be selected. Another regularized learning algorithm, called supervised algorithm, operates with $\mathcal{H}_K$ and $\Lambda_q^v$ suggested by the supervising algorithm, and predicts a future blood glucose profile in the form of a function $g(K, \lambda_+, z_T; \bullet)$ given by iterative Tikhonov regularization, as it has been described in the Remark 0.2. Here $\lambda_+$ is selected from $\Lambda_q^v$ in accordance with the quasi-balancing principle (vi), and $z_T$ consists of a few blood glucose measurements made before the moment of prediction.

We find it suitable to call such a predictor as fully adaptive regularization learning (FARL) algorithm, since both above mentioned algorithms are regularizations of the form (ii) with adaptively chosen kernels and regularization parameters. To the best of our knowledge such design of a predictor has been never proposed in the literature before.

The main distinctions between FARL-algorithm and prediction models based on time-series analysis are as follows:

For the identification of a time-series prediction model one is in need of comparatively large portions of chronologically ordered past glucose data, while FARL algorithm can be trained with the use of "piece-wise" data that have essential time gaps in measurements.

In numerical experiments with FARL-algorithm reported below future blood glucose concentration has been predicted from only two measurements made in the past 5 minutes. On the other hand, time-series predictors usually require more data and longer sampling history. For example, in [5] it is assumed that 3-5 measurements from the past 15-25 minutes are always available.

To describe FARL-algorithm assume that we are given a pool of historical data, which encompasses a sufficient number of blood glucose measurements/estimations performed with some patient previously.

In our numerical experiments such a Data Pool is formed by estimations of the blood glucose of the subject CHU102 obtained in the first day with the use of the kernel (xii), as it has been discussed in the previous section. More precisely, every 5 minutes we have read subject's blood glucose estimations $g_i$ from available measurements of raw electric signal.

The requirements imposed on a Data Pool in this particular embodiment are that data pieces $\{(t_i, g_i), i=p, p+1, \ldots, p+r\}$ forming the pool are "long enough" such that the length $r\Delta t$ of the time interval $[t_p, t_{p+r}]$ is larger than the length $(m+n-1)\Delta t$ of an interval, in which a predictor is expected to operate (Recall that blood glucose measurements/estimations $g_i$ are collected during a time period $(m-1)\Delta t$ and used in a prediction for time horizon $n\Delta t$). Moreover, it is expected that a Data Pool contains examples $\{(t_i, g_i)\}$ of hypo- and hyper-glycemia, when $g_i<70$ (mg/dl) or $g_i>180$ (mg/dl).

Assume that a Data Pool with pieces of data $\{(t_i, g_i), i=p, p+1, \ldots, p+r\}$ satisfying above-mentioned requirements is given. Then we need to transform it into a training set that will be used for constructing the supervising learning algorithm. Such a transformation can be done as follows. At first the form of the functional (x) is tailored to blood glucose prediction problem. For this purpose we take $$P(K, \lambda, z_P; g) = \frac{1}{|z_P|} \sum_{i:(t_i,g_i)\in z_P} |g_i - g(t_i)|_A, \quad (xiii)$$

where $$|g_i - g(t_i)|_A = \begin{cases} A & \text{if } c < 70(mg/dl) \wedge d \leq 180(mg/dl) \wedge (g_i - g(t_i)) < 0, \\ g_i - g(t_i) & \text{if } c < 70(mg/dl) \wedge d \leq 180(mg/dl) \wedge (g_i - g(t_i)) < 0, \\ g(t_i) - g_i & \text{if } c \geq 70(mg/dl) \wedge d > 180(mg/dl) \wedge (g(t_i) - g_i) < 0, \\ A & \text{if } c \geq 70(mg/dl) \wedge d > 180(mg/dl) \wedge (g(t_i) - g_i) < 0, \\ |g(t_i) - g_i| & \text{otherwise,} \end{cases}$$

$c=\min\{g_i:(t_i,g_i)\in Z_P\}$, $d=\max\{g_i:(t_i,g_i)\in Z_P\}$, and A (mg/dl) is a fixed large positive number. In our experiments A=40 mg/dl.

The idea behind the measure $|\bullet|_A$ is that it penalizes a delay or failure in the prediction of dangerous events of hypo- or hyper-glycemia.

We split each data piece $z=\{(t_i,g_i), i=p, p+1, \ldots, p+r\}$ from a given Data Pool into two parts $z_T=\{(t_i,g_i), i=p, p+1, \ldots, p+r-m\}$, $z_P\{(t_i,g_i), i=p+r-m+1, \ldots, p+r\}$, and choose a kernel $K(t, \tau)$ and a regularization parameter $\lambda$ by minimizing the transformed functional $Q(\mu, \lambda, z, K)$ (viii), (x), (xiii) over the sets (vii) and (iii) for some $\mu>0$. In our experiments we take $\mu=0.01$. In this way the parameters $\alpha=\alpha_p$, $\beta=\beta_p$, $\gamma=\gamma_p$, $\lambda=\lambda_{p,0}$, which allow the value $$\min\{Q(\mu,\lambda,z,K): K = K(t,\tau) = (t\tau)^\alpha + \beta e^{-\gamma(t-\tau)^2}, \alpha, \beta, \gamma \in [10^{-4},3], \lambda \in \Lambda_q^\nu\},$$

are assigned to each data piece $z_T=\{(t_i,g_i), i=p, p+1, \ldots, p+r-m\}$, which is used in constructing the predictor g(K, $\lambda_{p,0}$, $z_T$; t). On the other hand, the blood glucose trend reflected in data $z_T$ can be captured by the coefficients of the best linear fit $x_p^{(1)}t + x_p^{(2)}$ determined as $$(x_p^{(1)}, x_p^{(2)}) = \mathrm{argmin}\left\{\sum_{i:(t_i,g_i)\in z_T} (x^{(1)}t_i + x^{(2)} - g_i)^2, x^{(1)}, x^{(2)} \in \mathbb{R}\right\}.$$

Then the coefficient vectors $x_p=(x_p^{(1)}, x_p^{(2)})$ are considered as inputs of the training sets for the supervising learning algorithm.

Recall that this algorithm should be trained in choosing an adequate kernel K from (vii). Therefore, the parameters $\alpha=\alpha_p$, $\beta=\beta_p$, $\gamma=\gamma_p$, and $\lambda=\lambda_{p,0}$ are considered as outputs for training. In this way we form training sets $z^{(1)}=\{(x_p,\alpha_p)\}$, $z^{(2)}=\{(x_p,\beta_p)\}$, $z^{(3)}=\{(x_p,\gamma_p)\}$, $z^{(4)}=\{(x_p,\lambda_{p,0})\}$, to learn the parameters separately. Here the index p is running through the set of values corresponding to data pieces $\{(t_i,g_i), i=p, p+1, \ldots, p+r\}$ from the Data Pool.

The supervising algorithm comprises of regularized learning algorithms producing correspondingly the functions $\alpha=\alpha(K_1, x) = \alpha(K_1, \lambda_+^{(1)}, z_T^{(1)}; x)$, $\beta=\beta(K_2, x) = \beta(K_2, \lambda_{+(2)}, z_T^{(2)}; x)$, $\gamma=\gamma(K_3, x) = \gamma(K_3, \lambda_+^{(3)}, z_T^{(3)}; x)$, $\lambda=\lambda(K_4, x) = \lambda(K_4, \lambda_+^{(4)}, z_T^{(4)}; x)$, $x \in \mathbb{R} \times \mathbb{R}$, which are used to assign the parameters of a kernel K from (vii) and an initial term $\lambda_0$ in (iii) to each coefficient vector $x=(x^{(1)}, x^{(2)})$. These functions have the form of (ii) and minimize the functional (viii) for $K=K_i$, $z_T=z_T^{(i)}$, $\lambda=\lambda_+^{(i)}$, i=1, 2, 3, 4. Here $K_i$ are chosen from the set of radial basis functions $$, \kappa_{main} = \{K(x,u) = -\|x-u\|^{a_1} + a_2 e^{-a_3\|x-u\|^{a_4}}, a_1, a_4 \in [0,2], a_2, a_3 \in [0, 15]\}, \quad (xiv)$$

where $\|\bullet\|$ is the standard Euclidean norm. Note that from [8] it follows that kernels from (xiv) are positive definite functions provided $a_1$, $a_2$, $a_4$ are not equal to zero simultaneously.

To give further details we describe the way of constructing $\alpha=\alpha(K_1, x)$. The other functions are constructed in the same way.

We rearrange the set $z^{(1)}\{(x_p, \alpha_p)\}$ so that $z^{(1)}=\{(x_{pi}, \alpha_{pi})\}$, and $\alpha_{pi}<\alpha_{pi+1}$, i=1, 2, ..., $|z^{(1)}|-1$. Then we split rearranged set into two parts $z_T^{(1)}=\{(x_{pi}, \alpha_{pi}), i=3, \ldots, 1_T\}$, $1_T = |z^{(1)}|-2$, $z_p^{(1)} = z^{(1)} \setminus z_T^{(1)}$, and choose the kernel $K_1 \in \kappa_{main}$ as a minimizer of the functional (x) with $z_T=z_T^{(1)}$, $z_P=z_P^{(1)}$.

In experiments with data of the subject CHU102 we have taken (x) with $\lambda=10^{-4}$, $\mu=0.5$ and received $$K_1(x,u) = -\|x-u\|^{1.6} + 5e^{-0.001\|x-u\|^{0.016}}. \quad (xv)$$

In the same way the other kernels have been constructed:

$$K_2(x,u) = -\|x-u\|^{1.2} + 0.001 e^{-e\|x-u\|^{0.001}}$$

$$K_3(x,u) = -1 + e^{-0.001\|x-u\|^{0.003}}$$

$$K_4(x,u) = -\|x-u\|^{0.2} + 0.02 e^{-0.1\|x-u\|^{0.2}} \quad (xvi)$$

Using these kernels one can construct the minimizers of the functionals (viii) for $z_T = z_T^{(i)}$, i=1, 2, 3, 4, and then choose the parameters $\lambda_+^{(i)}$ in accordance with the quasi-balancing principle (vi). In this way the functions $\alpha=\alpha(K_1, \alpha)$, $\beta=\beta(K_2, x)$, $\gamma=\gamma(K_3, x)$, $\lambda=\lambda(K_4, x)$, have been constructed.

Now we are in a position to present the scheme of FARL-algorithm.

Learning mode. Precompute the kernels $K_i$, i=1, 2, 3, 4, and the functions $\alpha=\alpha(K_1, x)$, $\beta=\beta(K_2, x)$, $\gamma=\gamma(K_3, x)$, $\lambda=\lambda(K_4, x)$, using available Data Pool.

Operating mode.

Input: m measurements $g_i, g_{i-1}, \ldots, g_{i-m+1}$ of patient's blood glucose sampled with time interval $\Delta t$ at moments $t_i > t_{i-1} > \ldots > t_{i-m+1}$ Step 1: Find the coefficient vector $x=(x^{(1)}, x^{(2)})$ of the best linear fit $x^{(1)}t + x^{(2)}$ of the input data $z_T = \{(t_i, g_i)\}$.

Step 2: Choose the kernel $K(t,\tau) = (t\tau)^{\alpha} + \beta e^{-\gamma(t-\tau)^2}$, where $\alpha = \alpha(K_1, x)$, $\beta = \beta(K_2, x)$, $\gamma = \gamma(K_3, x)$.

Step 3: Using the kernel $K(t, \tau)$ calculate regularized approximants $g(K, \lambda, z_T, t)$ by means of iterative Tikhonov regularization (Remark 0.2) for $\lambda \in \Lambda_q^\nu$, where $\lambda_0 = \lambda(K_4, x)$.

Step 4: Construct a predictor of patient's blood glucose concentration $g(K, \lambda_+, z_T, t)$ for time period $t \in [t_i, t_i + n\Delta t]$, where $\lambda_+$ is chosed from $\Lambda_q^\nu$ in accordance with the quasi-balancing principle (vi).

It is interesting to note that a predictor based on FARL-algorithm can be potentially made portable from individual to individual without any need of changing the Learning mode: Once the functions $\alpha=\alpha(K_1, x)$, $\beta=\beta(K_2, x)$, $\gamma=\gamma(K_3, x)$, $\lambda=\lambda(K_4, x)$ are determined for one patients, they can be used for another ones without tuning.

To demonstrate above mentioned portability we apply FARL-algorithm calibrated for the subject CHU102 to predict 20 minutes ahead (i.e. n=4) the blood glucose concentration of other 8 subjects.

To quantify clinical accuracy of such predictions we again use Clarke Error Grid Analysis (EGA) described above. Moreover, as in that section, for each subject 60 HemoCue measurements from 2 hospital days are used as references in EGA. The results are presented in the Table 3.

TABLE 3

Percentage of points in EGA - zones for the blood glucose predictors based on FARL-algorithm, which has been trained with data of the subject CHU102

| Subject | A | B | C | D | E |
|---|---|---|---|---|---|
| CHU102 | 81.82 | 18.18 | — | — | — |
| CHU105 | 73.86 | 22.73 | — | 3.41 | — |
| CHU111 | 77.01 | 21.84 | — | 1.15 | — |
| CHU115 | 82.35 | 17.65 | — | — | — |
| CHU116 | 80.43 | 19.57 | — | — | — |
| CHU119 | 80.23 | 19.77 | — | — | — |
| CHU128 | 86.89 | 11.47 | — | 1.64 | — |
| UNIPD202 | 75.9 | 22.89 | — | 1.2 | — |
| UNIPD203 | 80.23 | 19.77 | — | — | — |
| Average | 79.86 | 19.32 | — | 0.82 | — |

Comparison of the Table 2 and 3 allows a conclusion that in average the predictors based on FARL-algorithm is even more accurate then Abbott glucose meter (it is especially interesting to compare percentages of points in D-zones).

It is not surprise, since in this embodiment the input for predictors is provided by the estimator of the glucose concentration based on the kernel (xii), which has been shown to be more accurate in average than the Abbott meter (compare the Tables 1 and 2).

Note that the possibility of having prediction models made portable from individual to individual has been also observed in [11] for data-driven autoregressive time series models. But in [11] a portability has been demonstrated only for 2 subjects. Moreover, in [11] the predictor input has been constructed by performing linear regression between the entire reference blood glucose measurements and corresponding subcutaneous electric current measurements. Then obtained regression fit has been applied to map electric signals $\{x_i\}$ into glucose concentrations $\{g_i\}$. It is easy to see that in this way a predictor is indirectly provided with an information about future blood glucose concentration that need to be predicted. Such kind testing strategies are sometimes called as "inverse crime". It occurs when reference data are employed to synthesize the input (see, e.g. [7]).

It should be noted that the results reported in the Table 3 correspond to the case, when only 2 blood glucose measurements/estimations $g_i$, $g_{i-1}$ samples with time interval $\Delta t=5$ (minutes) are used as a predictor input, i.e. m=2. To the best our knowledge, such a "poor input" has been never used for predicting blood glucose concentration before. Nevertheless, reported results show that for clinically important 20-minute-ahead blood glucose prediction the reliability of predictors based on FARL-algorithm is level with blood glucose meters reliability.

REFERENCES

[1] F. Bauer, S. V. Pereverzev and L. Rosasco, *On regularization algorithms in learing theory*, J. of Complexity, 23 (2007), pp. 52-72.

[2] A. Caponneto and Y. Yao, *Adaptation for Regularization Operators in learning Theory*, Technical Report CBCL Paper 265, MIT-CSAIL-TR 2006-063.

[3] W. L. Clarke, D. J. Cox, L. A. Gonder-Frederick, W. Carter, and S. L. Pohl, *Evaluating clinical accuracy of systems for self-monitoring of blood glucose*, Diabetes Care, 10 (1987), Issue 5, pp. 622-628.

[4] E. De Vito, S. V. Pereverzev and L. Rosasco, *Adaptive Kernel Methods Using the Balancing Principle*, Technical Report CBCL Paper 275, MIT-CSAIL-TR-2008-062.

[5] M. Eren-Oruklu, A. Cinar, L. Quinn and D. Smith, *Estimation of future glucose concentrations with subject-specific recursive linear models*, Diabetes Tech. & Therapeutics, 11 (2009), Issue 4, pp. 243-253.

[6] A. Facchinetti, G. Sparacino and C. Cobelli, *Reconstruction of glucose in plasma from interstitial fluid continuous glucose monitoring data: Role of sensor calibration*, J. of Diabetes Sci. and Tech., 1 (2007), Issue 5, pp. 617-623.

[7] J. Kaipio, E. Somersalo, *Statistical inverse problems: Discretization, model reduction and inverse crimes*, J. of computational and Applied Math., 198 (2007), pp. 493-504.

[8] C. A. Micchelli, *Interpolation of scattered data: Distance matrices and conditionally positive functions*, Constr. Approxiam., 2 (1986), pp. 11-22.

[9] C. A. Micchelli and M. Pontil, *Learning the kernel function via regularization*, J. of Machine Learning Research, 6 (2005), pp. 10991125.

[10] V. Naumova, S. V. Pereverzyev and S. Sivananthan, *Extrapolation in variable RKHSs with application to the blood glucose reading*, Inverse Problems, 27 (2011), 075010, 13 pp.

[11] J. Reitman, S. Rajaraman, A. Gribok and W. K. Ward, *Predictive monitoring for improved management of glucose levels*, J. of Diabetes Sci. and Tech., 1 (2007), Issue 4, pp. 478-486.

[12] G. Sparacino, F. Zanderigo, S. Corazza, A. Maran, A, Facchinetti and C. Cobelli, *Glucose concentration can be predicted ahead in time from continuous glucose monitoring sensor time-series*, IEEE Trans. on Biomedical Eng., 54 (2007), Issue 5, pp. 931-937.

[13] A. N. Tikhonov and V. B. Glasko, *Use of the regularization methods in non-linear problems*, USSR Comput. Math. Math. Phys., bf 5 (1965), pp. 93-107.

[14] G. Wahba, *Splines models for observational data*, Series in Applied Mathematics, 59, SIAM, Philadelphia, 1990.

[15] H. Wang, *Adaptive regularization algorithms in learning theory*, Master thesis, Johannes Kepler University Linz, 2008.

Some embodiments of the invention are summarised in the following:

Embodiment 1: A glucose prediction device comprising:
input means adapted to receive information indicative of a physiologic condition of a subject,
processing means adapted to predict a future glycaemic state of the subject on the basis of information received by the input means, and
output means adapted to convey information related to the predicted future glycaemic state,
wherein the processing means employs a multistage algorithm comprising a prediction setting stage specifying a functional space for the prediction and a prediction execution stage specifying a predicted future glycaemic state of the subject in the functional space as a continuous function of time, gp(t).

Embodiment 2: A device according to embodiment 1, wherein the specified function, gp(t), depends on a reproducing kernel and a regularization parameter, which are not fixed a priori.

Embodiment 3: A device according to embodiment 1 or 2, wherein the prediction setting stage comprises a) a labelling of data segments containing information received by the input means, and b) a suggestion of a kernel and an initial regularization parameter based on respective labels of the data segments, and wherein the prediction execution stage specifies a predicted glycaemic state by using the suggested kernel and initial regularization parameter to construct gp(t).

Embodiment 4: A device according to embodiment 3, wherein the labelling of data segments comprises a linear fitting, and wherein the suggestion of a kernel and an initial regularization parameter is based on respective coefficients of the linear fit.

Embodiment 5: A device according to any of the preceding embodiments, wherein gp(t) is constructed by a regularized learning algorithm in a reproducing kernel Hilbert space $H=H_K$.

Embodiment 6: A device according to any of the preceding embodiments, wherein the prediction setting stage specifies a functional space for the prediction on the basis of information obtained from a predetermined data pool.

Embodiment 7: A device according to any of embodiments 1-5, wherein the prediction setting stage specifies a functional space for the prediction on the basis of information obtained from a continuously updating data pool.

Embodiment 8: A device according to any of the preceding embodiments, wherein the information indicative of a physiologic condition of a subject comprises information related to at least one measurement of a body characteristic.

Embodiment 9: A device according to embodiment 8, wherein the body characteristic is blood or tissue glucose.

Embodiment 10: A device according to any of the preceding embodiments, wherein the input means is further adapted to receive information related to a therapeutic treatment.

Embodiment 11: A device according to embodiment 10, wherein the information related to a therapeutic treatment comprises information related to past delivery of a glucose regulating agent.

Embodiment 12: A device according to any of the preceding embodiment, wherein the input means is further adapted to receive information related to a meal consumed or to be consumed by the subject.

Embodiment 13: A method for predicting a future glucose profile of a subject, the method comprising:
receiving information related to at least one measurement of a body characteristic,
specifying a functional space for the prediction on the basis of the information received, and
specifying a predicted future glycaemic state of the subject in the functional space as a continuous function of time.

Embodiment 14: A method according to embodiment 13, wherein specifying a functional space for the prediction comprises labelling data segments containing information received by the input means and suggesting a kernel and an initial regularization parameter based on respective data segment labels.

Embodiment 15: A method according to embodiment 14, wherein specifying a predicted future glycaemic state of the subject in the functional space comprises using the suggested kernel and initial regularization parameter to construct a predictor.

The invention claimed is:

1. A glucose prediction device comprising:
an input device structured to receive information indicative of a physiologic condition of a subject;
a processing device comprising an adaptive regularization network that is structured to predict a future glucose profile;
an output device structured to convey the future glucose profile; and
an alarm;
wherein the future glucose profile is the glycaemic state of the subject as a continuous function of time;
wherein the adaptive regularization network is adapted to perform a multistage prediction process and comprises a supervising learning machine and a supervised learning machine that allows the future glucose profile to be predicted with irregularly sampled data in the information received by the input device;
wherein (a) the supervising learning machine is adapted to (i) compress the information received by the input device and (ii) run the compressed information through a pre-constructed machine to produce kernel parameters and a regularization parameter; and (b) the supervised learning machine is adapted to calculate the future glucose profile as a function of the information received by the input device and the kernel parameters and the regularization parameter produced by the supervising learning machine; and
wherein the alarm is structured to alert the subject if the future glucose profile includes an impending hypo- or hyperglycaemic event.

2. The device according to claim 1, wherein the pre-constructed machine is produced by a linear fitting, and wherein the kernel parameters and the regularization parameter is based on the linear fitting.

3. The device according to claim 1, wherein the multistage prediction process comprises a reproducing kernel Hilbert space.

4. The device according to claim 3, wherein the reproducing kernel Hilbert space is selected based on a data pool of training data segments, wherein each training data segment is indicative of the physiologic condition of the subject at a point in time.

5. The device according to claim 4, wherein the data pool is obtained from a predetermined data pool.

6. The device according to claim 4, wherein the data pool is obtained from a continuously updated data pool.

7. The device according to claim 1, wherein the information indicative of the physiologic condition of the subject is at least one measurement of a body characteristic.

8. The device according to claim 7, wherein the body characteristic is blood or tissue glucose.

9. The device according to claim 7, wherein the input device is further adapted to receive information related to a therapeutic treatment.

10. The device according to claim 9, wherein the information related to the therapeutic treatment is past delivery of a glucose regulating agent.

11. The device according to claim 1, wherein the input device is further adapted to receive information related to a meal consumed or to be consumed by the subject.

12. A computer-implemented method for predicting a future glucose profile of a subject that is the glycaemic state of the subject as a continuous function of time, the method comprising:
providing a glucose prediction device comprising a processing device;

receiving, by the processing device, information indicative of a physiologic condition of the subject;

specifying, by the processing device, a functional space for the predicted glucose profile by compressing the received information and running the compressed information through a pre-constructed machine to produce kernel parameters and a regularization parameter;

calculating, by the processing device, predicted glucose values as a continuous function of time based on the received information, the kernel parameters, and the initial regularization parameter to thereby produce the predicted future glucose profile of the subject; and alerting the user, by the glucose prediction device, if the future glucose profile of the subject includes an impending hypo- or hyperglycaemic event.

13. The method according to claim 12, further comprising producing the kernel parameters by a regularized learning algorithm in a reproducing kernel Hilbert space defined by at least approximately minimizing an error function.

14. The computer-implemented method according to claim 12, further comprising producing the pre-constructed machine by receiving a data pool of training data segments, wherein each training data segment is indicative of a physiologic condition of the subject at respective points in time;

compressing each training data segment to obtain a corresponding set of compressed training data segments;

determining a set of training parameters parameterising the functional space, wherein each training parameter of the training set minimizes a prediction error function indicative of a deviation between a physiologic condition and a predicted physiologic condition, wherein the predicted physiologic condition is predicted based on the functional space parameterised by said training parameter; and constructing, from the set of training parameters, a non-linear mapping between compressed input data segments and a set of kernel parameters parameterising the respective kernels.

15. The method according to claim 14, wherein constructing the non-linear mapping comprises determining a mechanism for determining a Tikhonov regularization parameter.

16. The method according to claim 14, wherein the prediction error function penalises a delay or failure in the prediction of physiological events classified as dangerous more heavily than a delay or failure in the prediction of physiological events classified as normal.

17. The method according to claim 14, wherein the data pool is obtained from a predetermined data pool.

18. The method according to claim 14, wherein the data pool is obtained from a continuously updated data pool.

19. The method according to claim 12, wherein the information indicative of the physiologic condition of the subject is at least one measurement of a body characteristic.

20. The method according to claim 19, wherein the body characteristic is blood or tissue glucose.

21. The method according to claim 12, further comprising receiving, by the processing device, information related to a therapeutic treatment.

22. The method according to claim 21, wherein the information related to the therapeutic treatment is past delivery of a glucose regulating agent.

23. The method according to claim 12, further comprising receiving, by the processing device, information related to a meal consumed or to be consumed by the subject.

24. A glucose prediction device comprising:

an input device structured to receive information indicative of a physiologic condition of a subject, wherein the information comprises blood or tissue glucose measurements;

a processing device comprising an adaptive regularization network that is structured to predict a future glucose profile;

an output device structured to convey the future glucose profile; and an alarm;

wherein the future glucose profile is the glycaemic state of the subject as a continuous function of time;

wherein the adaptive regularization network is adapted to perform a multistage prediction process and comprises a supervising learning machine and a supervised learning machine that allows the future glucose profile to be predicted with irregularly sampled data in the blood or tissue glucose measurements received by the input device;

wherein (a) the supervising learning machine is adapted to (i) compress the information received by the input device and (ii) run the compressed information through a pre-constructed machine to produce kernel parameters and a regularization parameter; and (b) the supervised learning machine is adapted to calculate the future glucose profile as a function of the information received by the input device and the kernel parameters and the regularization parameter produced by the supervising learning machine; and wherein the alarm is structured to alert the subject if the future glucose profile includes an impending hypo- or hyperglycaemic event.

25. The device according to claim 24, wherein the pre-constructed machine is produced by a linear fitting, and wherein the kernel parameters and the regularization parameter is based on the linear fitting.

26. The device according to claim 24, wherein the multistage prediction process comprises a reproducing kernel Hilbert space.

27. The device according to claim 26, wherein the reproducing kernel Hilbert space is selected based on a data pool of training data segments, wherein each training data segment is indicative of the physiologic condition of the subject at a point in time.

28. The device according to claim 27, wherein the data pool is obtained from a predetermined data pool.

29. The device according to claim 27, wherein the data pool is obtained from a continuously updated data pool.

30. The device according to claim 24, wherein the input device is further adapted to receive information related to a therapeutic treatment.

31. The device according to claim 30, wherein the information related to the therapeutic treatment is past delivery of a glucose regulating agent.

32. The device according to claim 24, wherein the input device is further adapted to receive information related to a meal consumed or to be consumed by the subject.

33. A computer-implemented method for predicting a future glucose profile of a subject that is the glycaemic state of the subject as a continuous function of time, the method comprising:

providing a glucose prediction device comprising a processing device;

receiving, by the processing device, information indicative of a physiologic condition of the subject, wherein the information comprises blood or tissue glucose measurements;

specifying, by the processing device, a functional space for the predicted glucose profile by compressing the received information and running the compressed information through a pre-constructed machine to produce kernel parameters and a regularization parameter, wherein the kernel parameters are produced by a regularized learning algorithm in a reproducing kernel Hilbert space defined by at least approximately minimizing an error function;

calculating, by the processing device, predicted glucose values as a continuous function of time based on the received information, the kernel parameters, and the initial regularization parameter to thereby produce the predicted future glucose profile of the subject; and alerting the user, by the glucose prediction device, if the future glucose profile of the subject includes an impending hypo- or hyperglycaemic event.

34. The method according to claim 33, further comprising producing the pre-constructed machine by receiving a data pool of training data segments, wherein each training data segment is indicative of a physiologic condition of the subject at respective points in time;

compressing each training data segment to obtain a corresponding set of compressed training data segments;

determining a set of training parameters parameterising the functional space, wherein each training parameter of the training set minimizes a prediction error function indicative of a deviation between a physiologic condition and a predicted physiologic condition, wherein the predicted physiologic condition is predicted based on the functional space parameterised by said training parameter; and constructing, from the set of training parameters, a non-linear mapping between compressed input data segments and a set of kernel parameters parameterising the respective kernels.

35. The method according to claim 34, wherein constructing the non-linear mapping comprises determining a mechanism for determining a Tikhonov regularization parameter.

36. The method according to claim 34, wherein the prediction error function penalises a delay or failure in the prediction of physiological events classified as dangerous more heavily than a delay or failure in the prediction of physiological events classified as normal.

37. The method according to claim 34, wherein the data pool is obtained from a predetermined data pool.

38. The method according to claim 34, wherein the data pool is obtained from a continuously updated data pool.

39. The method according to claim 33, further comprising receiving, by the processing device, information related to a therapeutic treatment.

40. The method according to claim 39, wherein the information related to the therapeutic treatment is past delivery of a glucose regulating agent.

41. The method according to claim 33, further comprising receiving, by the processing device, information related to a meal consumed or to be consumed by the subject.

* * * * *